United States Patent
Hyde et al.

(10) Patent No.: US 11,180,729 B2
(45) Date of Patent: *Nov. 23, 2021

(54) COMPOSITIONS AND METHODS INCLUDING CYTOTOXIC B LYMPHOCYTE CELL LINE EXPRESSING EXOGENOUS MEMBRANE IMMUNOGLOBULIN DIFFERENT FROM SECRETED IMMUNOGLOBULIN

(71) Applicant: THE INVENTION SCIENCE FUND II, LLC, Bellevue, WA (US)

(72) Inventors: Roderick A. Hyde, Redmond, WA (US); Wayne R. Kindsvogel, Seattle, WA (US); Gary L. McKnight, Bothell, WA (US)

(73) Assignee: THE INVENTION SCIENCE FUND II, LLC, Bellevue, WA (US)

( * ) Notice: Subject to any disclaimer, the term of this patent is extended or adjusted under 35 U.S.C. 154(b) by 189 days.

This patent is subject to a terminal disclaimer.

(21) Appl. No.: 16/256,222

(22) Filed: Jan. 24, 2019

(65) Prior Publication Data

US 2019/0153388 A1    May 23, 2019

Related U.S. Application Data

(60) Division of application No. 15/178,715, filed on Jun. 10, 2016, now Pat. No. 10,233,424, which is a continuation-in-part of application No. 14/549,685, filed on Nov. 21, 2014, now Pat. No. 9,512,213, which is a continuation of application No. 13/374,351, filed on Dec. 22, 2011, now Pat. No. 9,175,072.

(51) Int. Cl.
| | |
|---|---|
| A61K 35/12 | (2015.01) |
| C07K 16/40 | (2006.01) |
| C12N 5/0781 | (2010.01) |
| C12N 15/85 | (2006.01) |
| A61K 35/17 | (2015.01) |
| A61K 39/00 | (2006.01) |
| C07K 16/00 | (2006.01) |
| C07K 16/10 | (2006.01) |
| C07K 16/12 | (2006.01) |
| C07K 16/18 | (2006.01) |
| C07K 16/30 | (2006.01) |
| C07K 16/44 | (2006.01) |

(52) U.S. Cl.
CPC ............ *C12N 5/0635* (2013.01); *A61K 35/17* (2013.01); *A61K 39/00* (2013.01); *C07K 16/00* (2013.01); *C07K 16/109* (2013.01); *C07K 16/1018* (2013.01); *C07K 16/1271* (2013.01); *C07K 16/18* (2013.01); *C07K 16/3069* (2013.01); *C07K 16/44* (2013.01); *C12N 15/85* (2013.01); *A61K 2035/124* (2013.01); *A61K 2039/505* (2013.01); *A61K 2039/5156* (2013.01); *C07K 2317/14* (2013.01); *C07K 2317/76* (2013.01); *C12N 2510/00* (2013.01)

(58) Field of Classification Search
None
See application file for complete search history.

(56) References Cited

U.S. PATENT DOCUMENTS

| | | |
|---|---|---|
| 5,087,557 A | 2/1992 | McClure |
| 5,202,238 A | 4/1993 | Fell, Jr. |
| 5,997,859 A | 12/1999 | Barber |
| 6,570,061 B1 | 5/2003 | Rajewsky et al. |
| 6,576,464 B2 | 6/2003 | Gold |
| 6,841,383 B2 | 1/2005 | Reff |
| 7,015,034 B2 | 3/2006 | Lawman et al. |
| 7,166,704 B2 | 1/2007 | Batra et al. |
| 7,262,028 B2 | 8/2007 | Van Berkel |
| 7,378,276 B2 | 5/2008 | Ettinger |
| 7,429,486 B2 | 9/2008 | Van Berkel |
| 7,629,171 B2 | 12/2009 | Meagher et al. |
| 7,741,077 B2 | 6/2010 | Grawunder |
| 7,875,280 B2 | 1/2011 | Schneewind |
| 7,927,834 B2 | 4/2011 | Van Berkel |
| 7,939,059 B2 | 5/2011 | Yang |
| 7,993,864 B2 | 8/2011 | Brown et al. |
| 8,013,128 B2 | 9/2011 | Gudas |
| 8,101,181 B2 | 1/2012 | Ruben et al. |
| 9,175,072 B2 | 11/2015 | Hyde et al. |

(Continued)

FOREIGN PATENT DOCUMENTS

| | | |
|---|---|---|
| WO | 2006136008 A1 | 12/2006 |
| WO | WO-2010070263 A1 | 6/2010 |

(Continued)

OTHER PUBLICATIONS

PCT International Search Report; International App. No. PCT/US2019/022572; dated Jun. 26, 2019; pp. 1-8.

European Patent Office, Extended European Search Report, Pursuant to Rule 62 EPC; App. No. EP 17811004.5; dated Dec. 20, 2019; pp. 1-7.

(Continued)

*Primary Examiner* — Michail A Belyavskyi
(74) *Attorney, Agent, or Firm* — Adam L. K. Philipp; Shan Liao; AEON Law

(57) ABSTRACT

Compositions and methods are disclosed herein for producing one or more immunoglobulins in an isolated cytotoxic B lymphocyte cell line. An isolated cell line includes an isolated B lymphocyte cell line capable of expressing at least one exogenously incorporated membrane immunoglobulin reactive to a first antigen and at least one endogenous secreted immunoglobulin reactive to a second antigen, and further capable of expressing at least one exogenously incorporated recombinant B cell receptor that signals for expression of cytotoxic effector molecules.

32 Claims, 11 Drawing Sheets

(56) References Cited

U.S. PATENT DOCUMENTS

| | | |
|---|---|---|
| 2005/0170398 A1 | 8/2005 | Van Berkel et al. |
| 2005/0208120 A1 | 9/2005 | Albani |
| 2007/0071717 A1 | 3/2007 | Weiner et al. |
| 2007/0116690 A1 | 5/2007 | Yang |
| 2010/0261180 A1 | 10/2010 | Trapani et al. |
| 2011/0177073 A1 | 7/2011 | Van Berkel |
| 2013/0154277 A1 | 6/2013 | Willems |
| 2015/0203572 A1 | 7/2015 | Hyde et al. |
| 2015/0225470 A1 | 8/2015 | Zhang et al. |
| 2015/0283177 A1 | 10/2015 | Hyde et al. |
| 2016/0355783 A1 | 12/2016 | Hyde et al. |
| 2017/0173180 A1 | 6/2017 | Li |
| 2018/0215817 A1 | 8/2018 | Hyde et al. |

FOREIGN PATENT DOCUMENTS

| | | |
|---|---|---|
| WO | WO-2011050985 A1 | 5/2011 |
| WO | WO2013-096568 A1 | 6/2013 |

OTHER PUBLICATIONS

Zimmermann et al.; "Electromanipulation of Mammalian Cells: Fundamentals and Application"; IEEE Transactions on Plasma Science; Feb. 2000; pp. 72-82; vol. 28, No. 1; IEEE.

Yu et al.; "Human mb-1 Gene: Complete cDNA Sequence and Its Expression in B Cells Bearing Membrane Ig of Various Isotypes"; The Journal of Immunology; bearing a date of Jan. 15, 1992; pp. 633-637; vol. 148, No. 2; The American Association of Immunologists; Printed in U.S.A.

Wrammert et al.; "Rapid Cloning of High Affinity Human Monoclonal Antibodies Against Influenza Virus"; Nature; May 29, 2008; pp. 667-671; vol. 453, No. 7195.

GE Healthcare; Early kinetic screening of hybridomas for confident antibody selection using Biacore A100; May 2007; pp. 1-8.

Xu et al.; "Development and Characterization of Anti-Gal B Cell Receptor Transgenic Gal-1-Mice"; Transplantation; May 27, 2002; pp. 1549-1557; vol. 73, No. 10; Lippincott Williams & Wilkins, Inc.

European Patent Office, Supplementary European Search Report, Pursuant to Rule 62 EPC; App. No. EP 12859056; dated Apr. 10, 2015; pp. 1-6.

Abbas et al.; Cellular and Molecular. Immunology, 7th Edition; pp. 1-8 of book description printed from Amazon.com on Dec. 9, 2011.

Corti et al.; A Neutralizing Antibody Selected from Plasma Cells That Binds to Group 1 and Group 2 Influenza A Hemagglutinins; Science; Aug. 12, 2011; pp. 850-856; vol. 333; American Association for the Advancement of Science.

Bensinger et al.; Autologous transplantation with peripheral blood mononuclear cells collected after administration of recombinant granulocyte stimulating factor; Blood; Jun. 1, 1993; pp. 3158-3163; vol. 81, No. 11; The American Society of Hematology.

Early et al.; Immunoglobulin heavy chain gene organization in mice: Analysis of a myeloma genomic clone containing variable and a constant regions; Proc. Natl. Acad. Sci. USA; Feb. 1979; pp. 857-861; vol. 76, No. 2.

Biosearch Technologies; DNP-KLH (Keyhole Limpet Hemocyanin); Production Information; pp. 1-2; bearing a date of 2005.

Takacs et al., "The regulated long-term delivery of therapeutic proteins by using antigen-specific B lymphocytes", bearing a date of Nov. 16, 2004, pp. 16298-16303, vol. 101 No. 46, PNAS.

Ekiert et al.; Antibody Recognition of a Highly Conserved Influenza Virus Epitope; Science; Apr. 10, 2009; pp. 246-251; vol. 324; American Association for the Advancement of Science.

Tiller et al.; "Efficient generation of monoclonal antibodies from single human B cells by single cell RT-PCR and expression vector cloning"; Journal of Immunological Methods; Jan. 1, 2008; pp. 112-124; vol. 329, Issues 1-2; Elsevier B.V.

Kalos et al., Supplementary Materials for T Cells with Chimeric Antigen Receptors Have Potent Antitumor Effects and Can Establish Memory in Patients with Advanced Leukemia; Science Translational Medicine; 2011; 25 pages; vol. 3, 95ra73.

Kelly-Quintos et al.; Characterization of the Opsonic and Protective Activity against Staphylococcus aureus of Fully Human Monoclonal Antibodies Specific for the Bacterial Surface Polysaccharide Poly-N-Acetylglucosamine; Infection and Immunity; May 2006; pp. 2742-2750 vol. 74, No. 5; American Society for Microbiology.

Suk et al.; "A comprehensively molecular haplotype-resolved genome of a European individual"; Genome Research; Aug. 3, 2011; pp. 1-14, Lorenz et al.; Functional Antibodies Targeting IsaA of Staphylococcus aureus Augment Host Immune Response and Open New Perspectives for Antibacterial Therapy; Antimicrobial Agents and Chemotherapy; Jan. 2011; pp. 165-173; vol. 55, No. 1; American Society for Microbiology.

Khurana et al.; Antigenic Fingerprinting of H5N1 Avian Influenza Using Convalescent Sera and Monoclonal Antibodies Reveals Potential Vaccine and Diagnostic Targets; PLoS Medicine; Apr. 21, 2009; pp. 1-13; vol. 6, No. 4.

Price et al.; "Engineered cell surface expression of membrane immunoglobulin as a means to identify monoclonal antibody-secreting hybridomas"; Journal of Immunological Methods; 2009; pp. 28-41; vol. 343; Elsevier B.V.

PCT International Search Report; International App. No. PCT/US2012/070840; dated Apr. 29, 2013; pp. 1-3; and Search History (4 pages).

Sorenmo et al.; "CD40-Activated B Cell Cancer Vaccine Improves Second Clinical Remission and Survival in Privately Owned Dogs with Non-Hodgkin's Lymphoma"; PLoS ONE; Aug. 2011; pp. 1-8; vol. 6, Issue 8.

Schneider et al.; "A One-step Purification of Membrane Proteins Using a High Efficiency Immunomatrix"; The Journal of Biological Chemistry; Sep. 25, 1982; pp. 10766-10769; vol. 257, No. 18.

Rentenaar et al.; "Immune responsiveness in renal transplant recipients: Mycophenolic acid severely depresses humoral immunity in vivo"; Kidney International; 2002; pp. 319-328; vol. 62; International Society of Nephrology.

Zhang et al.; "Suppression of human prostate tumor growth by a unique prostate-specific monoclonal antibody F77 targeting a glycolipid marker"; PNAS; Jan. 12, 2010; pp. 732-737; vol. 107, No. 2.

Amaxa® Human B Cell Nucleofector® Kit; Product Information; pp. 1-4; printed on Jun. 6, 2016; Lonza Cologne AG.

Bueno et al.; "Reprogramming human B cells into induced pluripotent stem cells and its enhancement by C/EBPa"; Leukemia; Nov. 27, 2015; pp. 1-9; Macmillan Publishers Limited.

Casey et al.; "IL-21 Promotes Differentiation of Naive CD8 T Cells to a Unique Effector Phenotype"; The Journal of Immunology; Mar. 7, 2007; pp. 7640-7648; vol. 178; The American Association of Immunologists, Inc.

Corti et al.; "Heterosubtypic neutralizing antibodies are produced by individuals immunized with a seasonal influenza vaccine"; The Journal of Clinical Investigation; May 2010; pp. 1663-1673; vol. 120, No. 5.

Cruz-Guilloty et al.; "Runx3 and T-box proteins cooperate to establish the transcriptional program of effector CTLs"; The Journal of Experimental Medicine; Jan. 12, 2009; pp. 51-59; vol. 206, No. 1; The Rockefeller University Press.

Hagn et al.; "Human B cells differentiate into granzyme B-secreting cytotoxic B lymphocytes upon incomplete T-cell help"; Immunology and Cell Biology; Aug. 2, 2011; pp. 457-467; Australasian Society for Immunology Inc.

Hagn et al.; "Why do human B cells secrete granzyme B? Insights into a novel B-cell differentiation pathway"; OncoImmunology; Sep. 9, 2015; pp. 1368-1375; vol. 1, Issue 8.

Milone et al.; "Chimeric Receptors Containing CD137 Signal Transduction Domains Mediate Enhanced Survival of T Cells and Increased Antileukemic Efficacy In Vivo"; Molecular Therapy; Aug. 2009; pp. 1453-1464; vol. 17, No. 8; The American Society of Gene & Cell Therapy Pansri et al.; "A compact phage display human scFv library for selection of antibodies to a wide variety of antigens"; BMC Biotechnology; Jan. 29, 2009; pp. 1-16; vol. 9, No. 6; BioMed Central Ltd.

(56) References Cited

OTHER PUBLICATIONS

Parrish-Novak et al.; "Interleukin-21 and the IL-21 receptor: novel effectors of NK and T cell responses"; Journal of Leukocyte Biology; Nov. 2002; pp. 856-863; vol. 72.

Tyler et al.; "mRNA for surface immunoglobulin γ chains encodes a highly conserved transmembrane sequence and a 28-residue intracellular domain"; Proc. Natl. Acad. Sci. USA; Mar. 1982; pp. 2008-2012; vol. 79.

Visintin et al.; "Selection of antibodies for intracellular function using a two-hybrid in vivo system"; PNAS; Oct. 12, 1999; pp. 11723-11728; vol. 96, No. 21.

Xia et al.; "IL-2 augments the therapeutic efficacy of adoptively transferred B cells which directly kill tumor cells via the CXCR4/CXCL12 and perforin pathways"; Oncotarget; Aug. 9, 2016; 14 pgs.; vol. 7, No. 37; located at: www.impactjournals.com/oncotarget.

Li et al.; "Adoptive Transfer of Tumor Reactive B Cells Confers Host T-Cell Immunity and Tumor Regression"; Clinical Cancer Research Journal; 2011; 9 pgs.;vol. 17, No. 15; American Association for Cancer Research.

Li et al.; "In Vivo Sensitized and In Vitro Activated B Cells Mediate Tumor Regression in Cancer Adoptive Immunotherapy"; The Journal of Immunology; Aug. 10, 2009; pp. 3195-3203; vol. 183; The American Association of Immunologists, Inc.

Arimoto-Miyamoto et al.; "Optimal stimulation for CD70 induction on human monocyte-derived dendritic cells and the importance of CD70 in naive CD4+ T-cell differentiation"; Immunology; Nov. 18, 2009; pp. 137-149; vol. 130; Blackwell Publishing Ltd.

Balazs et al.; "Antibody-based protection against HIV infection by vectored immunoprophylaxis"; Nature; Nov. 30, 2011; pp. 81-84; vol. 481, No. 7379; Macmillan Publishers Limited.

Bhatt et al.; "The Role of the Microbiome in Cancer Development and Therapy"; CA Cancer J Clin; Jul./Aug. 2017; pp. 326-344; vol. 67, No. 4.

Bovia et al.; Efficient transduction of primary human B lymphocytes and nondividing myeloma B cells with HIV-1-derived lentiviral vectors; Blood; Mar. 1, 2003; pp. 1727-1733; vol. 101, No. 5; The American Society of Hematology.

Cabinian et al.; "Transfer of Maternal Immune Cells by Breastfeeding: Maternal Cytotoxic T Lymphocytes Present in Breast Milk Localize in the Peyer's Patches of the Nursed Infant"; PLOS One; Jun. 10, 2016; pp. 1-18; vol. 11; No. 6.

Casucci et al.; Suicide Gene Therapy to Increase the Safety of Chimeric Antigen Receptor-Redirected T Lymphocytes; Journal of Cancer, Jul. 1, 2011; pp. 378-382; vol. 2; Ivyspring International Publisher.

Croft et al.; "The Significance of OX40 and OX40L to T cell Biology and Immune Disease"; Immunol Rev.; May 2009; pp. 173-191; vol. 229, No. 1.

Durand et al.; "Regulatory B Cells with a Partial Defect in CD40 Signaling and Overexpressing Granzyme B Transfer Allograft Tolerance in Rodents"; The Journal of Immunology; Oct. 2, 2015; pp. 1-10; vol. 195; The American Association of Immunologists, Inc.

European Patent Office, Communication Pursuant to Article 94(3) EPC; App. No. EP 12 859 056.9-1402; dated Dec. 23, 2015; pp. 1-4.

Eyquem et al.; "Targeting a CAR to the TRAC locus with CRISPR/Cas9 enhances tumour rejection"; Nature; Mar. 2, 2017; pp. 113-117; vol. 543, No. 7643; Macmillan Publishers Limited, part of Springer Nature.

Farra et al.; "First-in-Human Testing of a Wirelessly Controlled Drug Delivery Microchip"; Science Translational Medicine; Feb. 22, 2012; pp. 1-12; vol. 4, Issue 122.

Kim et al.; "High Cleavage Efficiency of a 2A Peptide Derived from Porcine Teschovirus-1 in Human Cell Lines, Zebrafish and Mice"; PLoS ONE; Apr. 29, 2011; pp. 1-8; vol. 6, No. 4.

Kwakkenbos et al.; "Generation of stable monoclonal antibody-producing BCR+ human memory B cells by genetic programming"; Nat Med.; Jan. 2010; pp. 123-128; vol. 16, No. 1.

Le Cong et al.; "Multiplex Genome Engineering Using CRISPR/Cas Systems"; Science; Feb. 15, 2013; pp. 819-823; vol. 339, No. 6121.

Lund, Frances E.; "Cytokine-producing B lymphocytes—key regulators of immunity"; Curr Opin Immunol.; Jun. 2008; pp. 332-338; vol. 20, No. 3.

Okada et al.; "Chemokine Requirements for B Cell Entry to Lymph Nodes and Peyer's Patches"; J. Exp. Med.; Jul. 1, 2002; pp. 65-75; vol. 196, No. 1; The Rockefeller University Press.

Sackstein et al.; "T-lymphocyte homing: an underappreciated yet critical hurdle for successful cancer immunotherapy"; Laboratory Investigation; Mar. 27, 2017; pp. 669-697; vol. 97, USCAP, Inc.

Schmidt et al.; "Signalling of the BCR is regulated by a lipid rafts-localised transcription factor, Bright"; The EMBO Journal; Feb. 12, 2009; pp. 711-724; vol. 28; European Molecular Biology Organization.

Shi et al.; "Interaction between the gut microbiome and mucosal immune system"; Military Medical Research; 2017; pp. 1-7; vol. 4, No. 14.

Tangye et al.; "Human IgM+CD27+ B Cells: Memory B Cells or "Memory" B Cells?"; J Immunol; May 14, 2007; pp. 13-19; vol. 179; The American Association of Immunologists, Inc.

Vettermann, C. et al., "Allelic exclusion of immunoglobulin genes: models and mechanisms", Immunological Reviews, (2010), vol. 237, doi:doi:10.1111/j.1600-065X.2010.00935.x, pp. 22-42, XP055536935.

Xu et al., "Development and Characterization of Anti-Gal B Cell Receptor Transgenic Gal-/-Mice.", Transplantation, (May 27, 2002), vol. 73, No. 10, pp. 1549-1557, XP008174193.

Xu et al.; "No receptor stand alone: IgG B-cell receptor intrinsic and extrinsic mechanisms contribute to antibody memory"; Cell Research; May 20, 2014; pp. 651-664; vol. 24.

Xu, Hui et al., "Development and characterization of anti-Gal B cell receptor transgenic Gal-/-mice", Transplantation, (May 27, 2002), vol. 73, No. 10, doi:doi:10.1097/00007890-200205270-00006, ISSN 0041-1337, pp. 1549-1557, XP008174193.

Yu et al. (The J of Immunol., 1992, v.148pp. 633-637.

Zheng et al.; "Precise gene deletion and replacement using the CRISPR/Cas9 system in human cells"; BioTechniques; Sep. 2014; pp. 115-124; vol. 57, No. 3.

Magdalena Hagn, et al. "Why do human B cells secrete granzyme B Insights in a novel B-cell differentiation pathway" Oncoimmunology, vol. 1, No. 8, Nov. 1, 2012; pp. 1368-1375.

Figure 2
2A. Maternal Chromosome 14 Germline Configuration
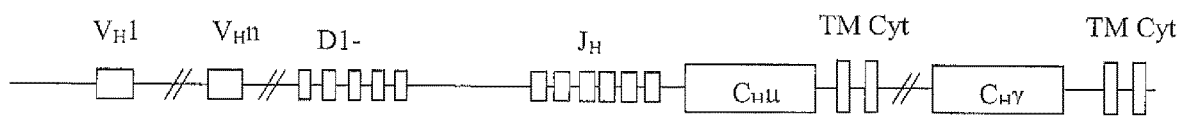
2B. Paternal Chromosome 14 Functionally Rearranged
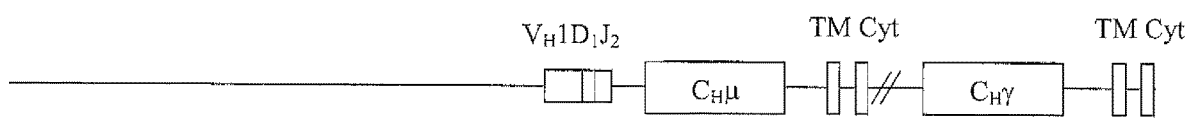
2C. Secreted and Membrane μ-H Chains Encoded
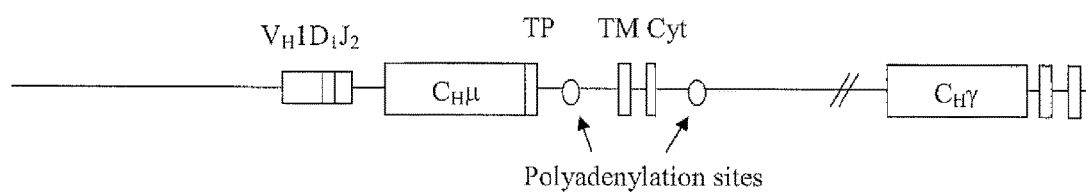
Polyadenylation sites Figure 3
3A. Secreted and Membrane γ-H Chain Gene with Alternate Polyadenylation Sites
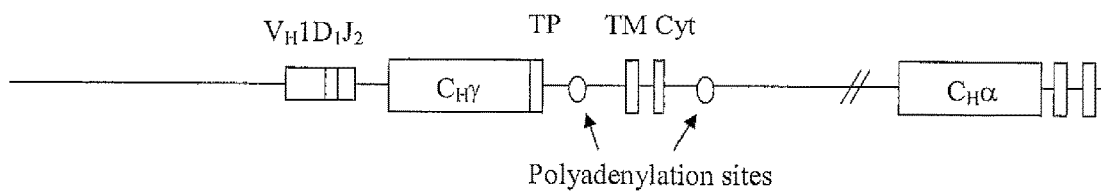
Polyadenylation sites
3B. Maternal Chromosome 14 with Membrane γ-H Chain Gene
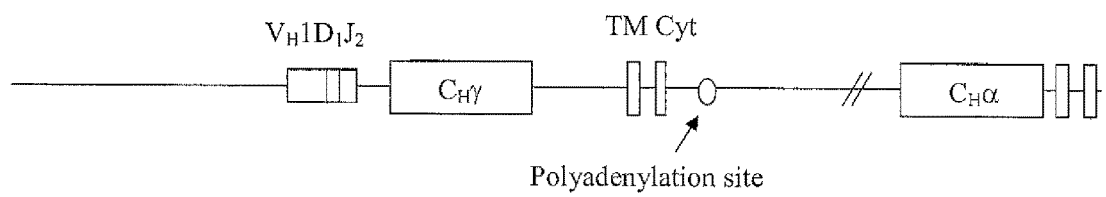
Polyadenylation site
3C. Paternal Chromosome 14 with Secreted γ-H Chain Gene
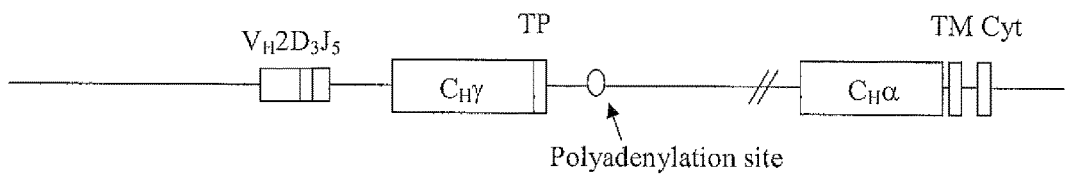
Polyadenylation site

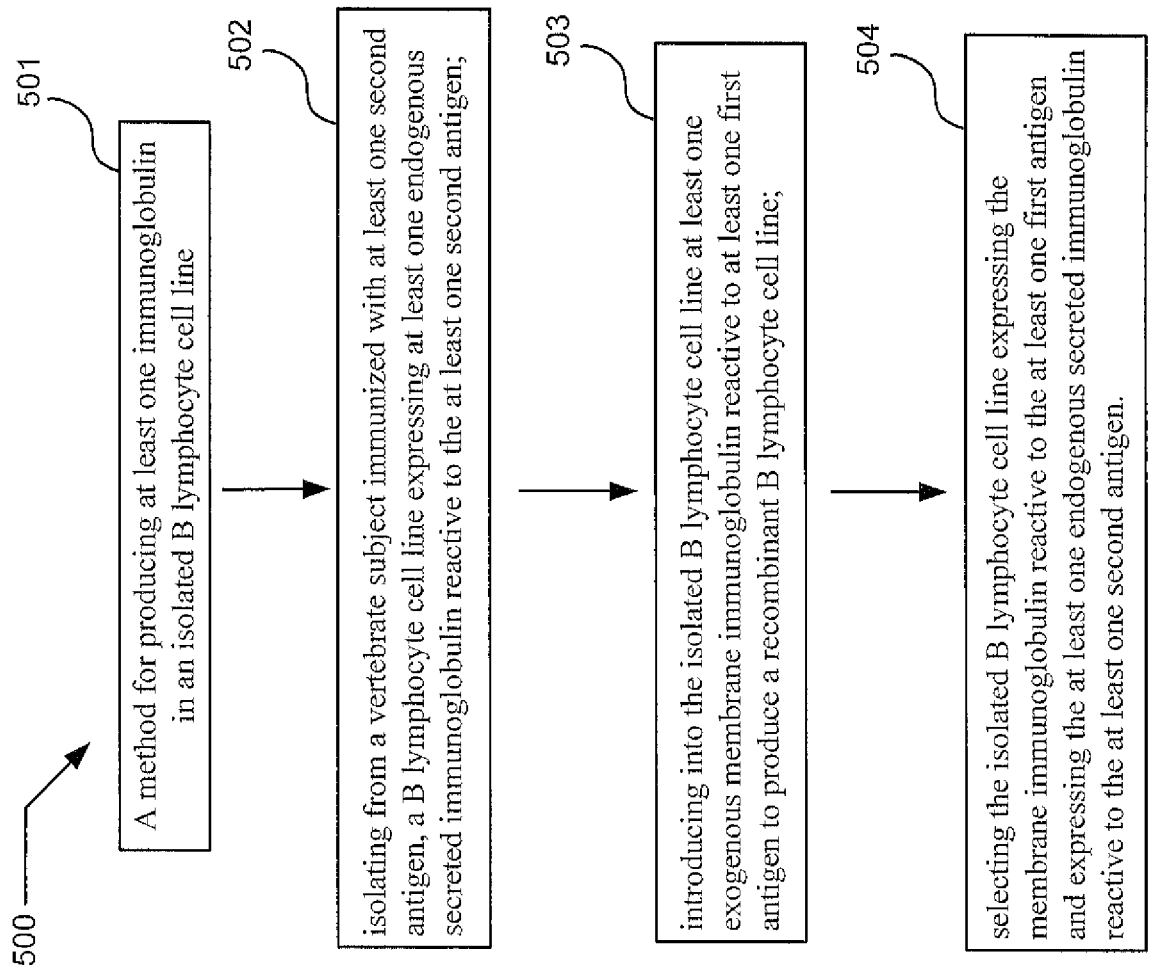

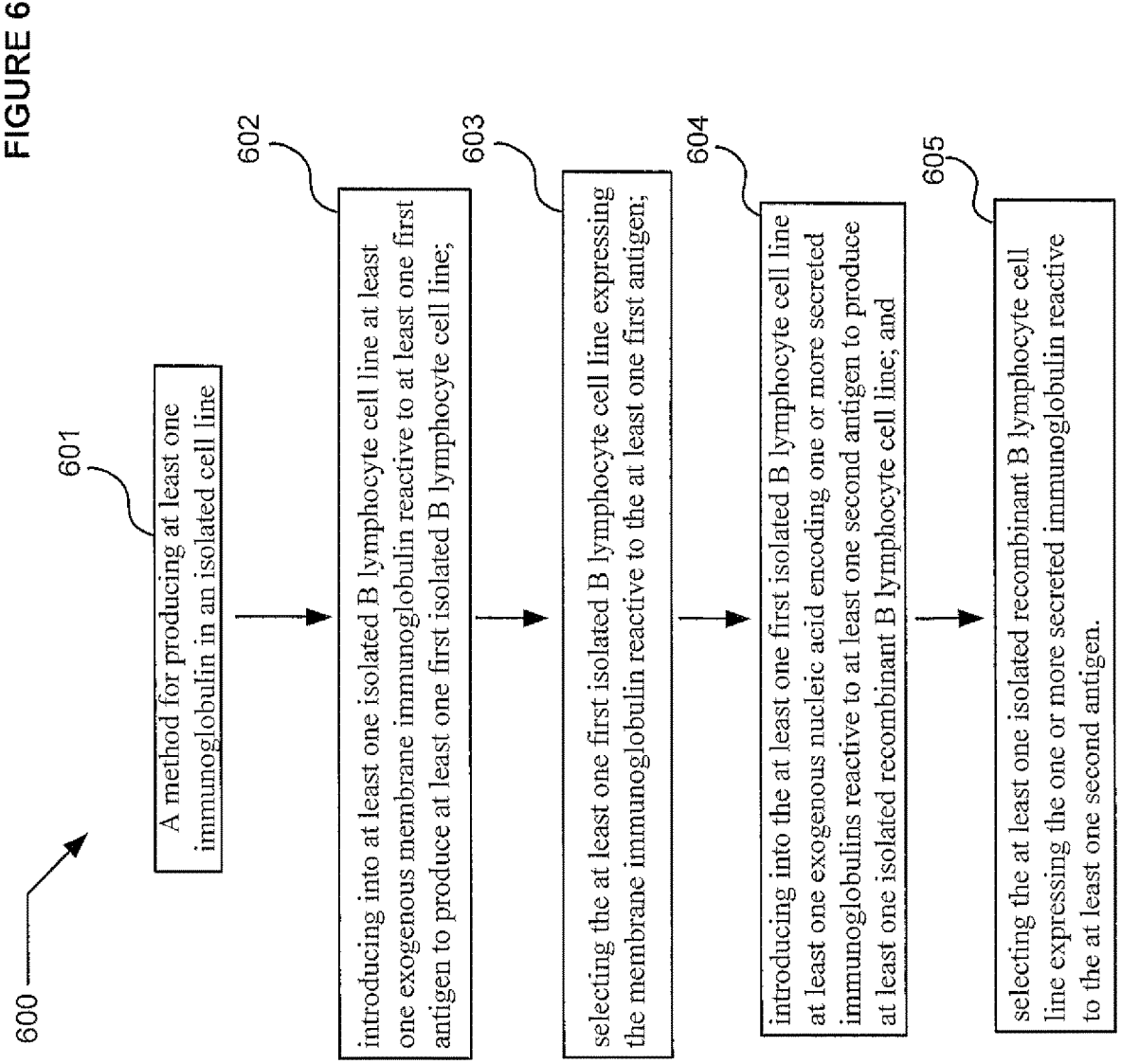

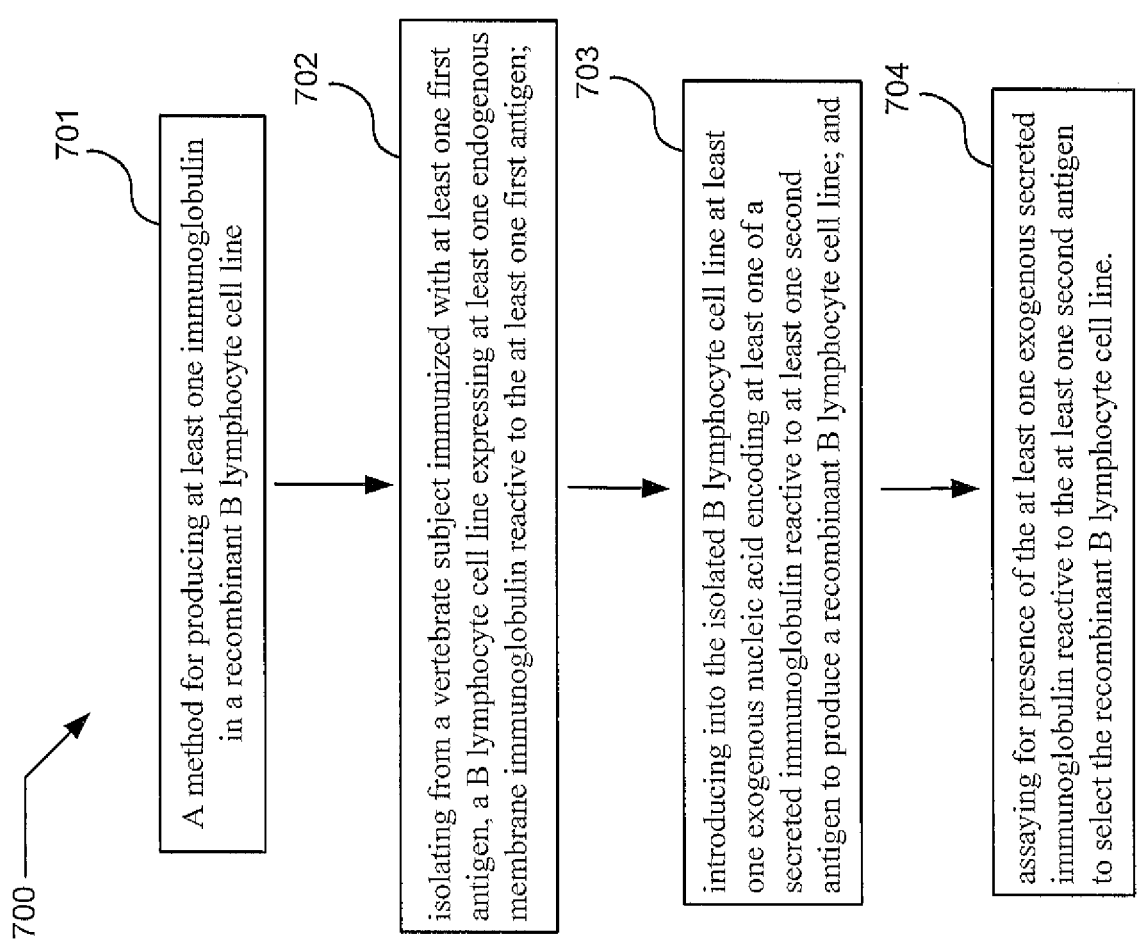

COMPOSITIONS AND METHODS INCLUDING CYTOTOXIC B LYMPHOCYTE CELL LINE EXPRESSING EXOGENOUS MEMBRANE IMMUNOGLOBULIN DIFFERENT FROM SECRETED IMMUNOGLOBULIN

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a divisional of U.S. patent application Ser. No. 15/178,715, now U.S. patent No. 10,233,424, entitled COMPOSITIONS AND METHODS INCLUDING CYTOTOXIC B LYMPHOCYTE CELL LINE EXPRESSING EXOGENOUS MEMBRANE IMMUNOGLOBULIN DIFFERENT FROM SECRETED IMMUNOGLOBULIN, which claims priority from U.S. patent application Ser. No. 14/549,685, now U.S. Pat. No. 9,512,213, which claims priority from U.S. patent application Ser. No. 13/374,351, now U.S. Pat. No. 9,175,072. The present application constitutes a continuation-in-part of U.S. Pat. application Ser. No. 13/374,351, now U.S. Pat. No. 9,175,072, entitled COMPOSITIONS AND METHODS INCLUDING RECOMBINANT B LYMPHOCYTE CELL LINE INCLUDING AN EXOGENOUSLY INCORPORATED NUCLEIC ACID EXPRESSING AN EXOGENOUS MEMBRANE IMMUNOGLOBULIN REACTIVE TO A FIRST ANTIGEN AND INCLUDING AN ENDOGENOUS GENE EXPRESSING AN ENDOGENOUS SECRETED IMMUNOGLOBULIN REACTIVE TO A SECOND ANTIGEN, naming Roderick A. Hyde and Wayne R. Kindsvogel as inventors, filed 2011 Dec. 22.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

Compositions and methods are disclosed herein for producing an immunoglobulin in a recombinant B lymphocyte cell line. Compositions and methods are disclosed herein for treating a disease in a vertebrate subject with an immunotherapeutic product. The immunotherapeutic product can include the recombinant B lymphocyte cell line that produces one or more antibodies. The immunotherapeutic product can include the recombinant B lymphocyte cell line that is an exceptional antigen presenting cell.

Compositions and methods are disclosed herein for producing one or more immunoglobulins in an isolated B lymphocyte cell line. Compositions and methods are disclosed herein for producing one or more immunoglobulins in the isolated B lymphocyte cell line that direct cell signaling by membrane immunoglobulin in the isolated B lymphocyte cell line. Immune cell therapy in a vertebrate subject can include administering to the vertebrate subject the isolated B lymphocyte cell line that synthesizes secreted immunoglobulins and membrane immunoglobulins each having different target antigens. Immune cell therapy in a vertebrate subject can include administering to the vertebrate subject antigen presenting cells comprised of the isolated B lymphocyte cell line that direct antigen internalization and processing to produce exceptional antigen presenting cells. The isolated B lymphocyte cell line can produce antigen presenting cells that are exceptional or superior at capturing, internalizing and presenting the antigen recognized by the endogenous or exogenously derived membrane immunoglobulin. Compositions and methods are disclosed herein for treating a disease in a vertebrate subject with an immunotherapeutic product. The immunotherapeutic product can include the isolated B lymphocyte cell line having an endogenously-derived or exogenously derived membrane immunoglobulin reactive to a first antigen wherein the isolated B lymphocyte cell line produces one or more secreted immunoglobulins reactive to a second antigen. The immunotherapeutic product can include the isolated B lymphocyte cell line that can be a monoclonal B lymphocyte cell line or polyclonal B lymphocyte cell line that produces one or more secreted immunoglobulins. The immunotherapeutic product can include the isolated B lymphocyte cell line that produces one or more secreted antibodies, e.g., antibodies that recognize different epitopes on the same antigen. The immunotherapeutic product can include the isolated B lymphocyte cell line as one or more antigen presenting cells.

The isolated B lymphocyte cell line can include an immunotherapeutic product administered to a vertebrate subject to develop long-lived isolated B lymphocytes in the vertebrate subject for immune surveillance of chronic disease. The immunotherapeutic product can include the isolated B lymphocyte cell line having an endogenously-derived or exogenously derived membrane immunoglobulin that can be administered to a vertebrate subject to provide an antigen presenting cell to the vertebrate subject.

An isolated cell line as described herein can include an isolated B lymphocyte cell line capable of expressing at least one exogenously incorporated membrane immunoglobulin reactive to a first antigen and at least one endogenous secreted immunoglobulin reactive to a second antigen. The isolated B lymphocyte cell line is capable of expressing at least one endogenous membrane immunoglobulin reactive to the second antigen. The at least one exogenously incorporated membrane immunoglobulin can include one or more exogenously incorporated membrane immunoglobulin polypeptides. The at least one exogenously incorporated membrane immunoglobulin can include at least one exogenously incorporated nucleic acid encoding the at least one membrane immunoglobulin, wherein the cell line is capable of expressing the at least one membrane immunoglobulin. The at least one exogenously incorporated membrane immunoglobulin comprises at least two exogenously incorporated nucleic acid encoding the at least one membrane immunoglobulin. The at least one exogenously incorporated membrane immunoglobulin can include nucleic acids encoding two heavy chain (H) immunoglobulins and two light chain (L) immunoglobulins. The at least one exogenously incorporated membrane immunoglobulin can include nucleic acids encoding one heavy chain (H) immunoglobulin and one light chain (L) immunoglobulin. The at least one exogenously incorporated membrane immunoglobulin can include nucleic acids encoding one single chain FIT immunoglobulin. The exogenously incorporated nucleic acid encoding the at least one membrane immunoglobulin can be present in one or more chromosomal loci in the isolated B lymphocyte cell line. The isolated B lymphocyte cell line is capable of disrupting expression of the endogenous membrane immunoglobulin reactive to the second antigen. The at least two exogenously incorporated nucleic acids encoding the at least one of the membrane immunoglobulin can be present in Ig H chain and Ig L chain chromosomal loci in the isolated B lymphocyte cell line. The at least one exogenously incorporated nucleic acid encoding the at least one membrane immunoglobulins can be present in one or more non-Ig L or non-Ig H chromosomal loci in the isolated B lymphocyte cell line. The at least one exogenously incorporated nucleic acid encoding the at least one membrane immunoglobulin can be present in an extrachromosomal replicating genetic element in the isolated B lymphocyte cell line. The at least one exogenously incorporated nucleic acid encoding the at least one membrane immunoglobulin can be derived from a B lymphocyte cell line. The at least one exogenously incorporated membrane immunoglobulin activated by the first antigen is capable of controlling expression of the at least one endogenous secreted immunoglobulin reactive to the second antigen. The isolated B lymphocyte cell line can include at least one of naïve B lymphocyte, immature B lymphocyte, transitional B lymphocyte, mature B lymphocyte, follicular B lymphocyte, memory B lymphocyte, plasmablast, or plasma cell. The isolated B lymphocyte cell line can include a polyclonal population of B lymphocytes. The isolated B lymphocyte cell line can include a monoclonal population of B lymphocytes. The membrane immunoglobulin can include at least one of a membrane anchor, a cytoplasmic domain, and an extracellular ligand-binding domain.

An isolated recombinant cell line as described herein can include an isolated B lymphocyte cell line capable of expressing at least one exogenously incorporated membrane immunoglobulin reactive to a first antigen and at least one exogenously incorporated nucleic acid encoding secreted immunoglobulin reactive to a second antigen. The isolated B lymphocyte cell line is capable of expressing at least one exogenously incorporated nucleic acid encoding membrane immunoglobulin reactive to the second antigen. The isolated B lymphocyte cell line is capable of expressing at least one exogenously incorporated nucleic acid encoding a secreted immunoglobulin reactive to a third antigen. The second antigen and the third antigen can be different epitopes of a single antigenic polypeptide. The at least one exogenously incorporated membrane immunoglobulin can include at least one exogenously incorporated membrane immunoglobulin polypeptide. The at least one exogenously incorporated membrane immunoglobulin can include at least one exogenously incorporated nucleic acid encoding at least one membrane immunoglobulin polypeptide, wherein the cell line is capable of expressing the at least one membrane immunoglobulin polypeptide. The at least one exogenously incorporated nucleic acid encoding the at least one membrane immunoglobulin can be present in one or more chromosomal loci in the isolated B lymphocyte cell line. The at least two exogenously incorporated nucleic acids encoding the at least one membrane immunoglobulins can be present in Ig H chain and Ig L chain chromosomal loci in the isolated B lymphocyte cell line. The at least one exogenously incorporated nucleic acid encoding the at least one membrane immunoglobulin can be present in one or more non-Ig L or non-Ig H chromosomal loci in the isolated B lymphocyte cell line. The at least one exogenously incorporated nucleic acids encoding the at least one membrane immunoglobulin can be present in an extrachromosomal replicating genetic element in the isolated B lymphocyte cell line. The nucleic acid encoding the at least one membrane immunoglobulin can be derived from a B lymphocyte cell line. The at least one exogenously incorporated membrane immunoglobulin activated by the first antigen is capable of controlling expression of the at least one exogenously incorporated secreted immunoglobulin reactive to the second antigen. The isolated B lymphocyte cell line can include at least one of naïve B lymphocyte, immature B lymphocyte, transitional B lymphocyte, mature B lymphocyte, follicular B lymphocyte, memory B lymphocyte, plasmablast, or plasma cell. The isolated B lymphocyte cell line can include a polyclonal population of B lymphocytes. The isolated B lymphocyte cell line can include a monoclonal population of B lymphocytes. The membrane immunoglobulin can include at least one of a membrane anchor, a cytoplasmic domain, and an extracellular ligand-binding domain.

In an embodiment, a modified B lymphocyte includes structural or functional features for exhibiting cellular cytotoxicity. For example, in an embodiment, a modified B lymphocyte cell or cell line produces one or more antibodies and has one or more B cell receptors (membrane immunoglobulins as described herein) that are specific to target antigens, such as tumor antigens (including but not limited to, antigens that are mutant forms of "normal" cellular antigens, as well as antigens that are modified by way of post-translational modifications, and antigens that are expressed in an abnormal way or in an abnormal level). In an embodiment, a modified B lymphocyte cell or cell line is capable of mounting a complete immune response with both humoral as well as cellular immune components. Thus, cytotoxicity expression can include secreted antibody or antibodies. Cytotoxicity expression can also include direct cell-to-cell contact that induces death (e.g., by lysis, necrosis, apoptosis, etc.). One of the goals of various embodiments is to provide highly specific, highly effective killing of target cells by the modified B lymphocytes described herein. In an embodiment, the target cells include cancer cells (e.g., tumor or other cancer cells). In an embodiment, the target cells include cells that are related to autoimmune disease or infection. In an embodiment, the target cells include donor or host cells that are reactive to donor cells from a cell, tissue, or organ transplant (e.g., graft-versus-host disease). In an embodiment, the target cells include cells related to pathological inflammation or infection.

A method for producing an immunoglobulin in an isolated B lymphocyte cell line as described herein can include isolating from a vertebrate subject exposed to, e.g., by infection, or immunized with at least one second antigen, a B lymphocyte cell line expressing at least one endogenous secreted immunoglobulin reactive to the at least one second antigen; introducing into the isolated B lymphocyte cell line at least one exogenous membrane immunoglobulin reactive to at least one first antigen to produce a recombinant B lymphocyte cell line; and selecting the isolated B lymphocyte cell line expressing the membrane immunoglobulin reactive to the at least one first antigen and expressing the at least one endogenous secreted immunoglobulin reactive to the at least one second antigen. The method of claim can include administering the at least one first antigen to stimulate the recombinant B lymphocyte cell line; and assessing production of the at least one endogenous secreted immunoglobulin reactive to the at least one second antigen in the recombinant B lymphocyte cell line. In the method, introducing into the at least one isolated recombinant B lymphocyte cell line at least one exogenous membrane immunoglobulin reactive to the at least one first antigen can include introducing at least one exogenous membrane immunoglobulin polypeptide reactive to the at least one first antigen. Introducing into the at least one isolated recombinant B lymphocyte cell line at least one exogenous membrane immunoglobulin reactive to the at least one first antigen can include introducing at least one exogenous nucleic acid encoding at least one membrane immunoglobulin reactive to the at least one first antigen. The method can include exposing the recombinant B lymphocyte cell line to the at least one first antigen to activate the recombinant B lymphocyte cell line to express the endogenous secreted immunoglobulin reactive to the at least one second antigen. The method can include isolating the endogenous secreted immunoglobulin reactive to the at least one second antigen from the recombinant B lymphocyte cell line or from a culture of the recombinant B lymphocyte cell line. In the method, activating the at least one exogenously incorporated membrane immunoglobulin with the first antigen is capable of controlling expression of the at least one exogenously incorporated nucleic acid encoding at least one secreted immunoglobulin reactive to the second antigen. The isolated B lymphocyte cell line can include at least one of naïve B lymphocytes, immature B lymphocytes, transitional B lymphocytes, mature B lymphocytes, follicular B lymphocytes, memory B lymphocytes, plasmablasts, or plasma cells. The isolated B lymphocyte cell line can include at least one memory B lymphocyte.

In an embodiment, the isolated B lymphocyte cell line that has been modified by way of a chimeric B cell receptor or recombinant B cell receptor includes utilizing scFv fragments in construction of the modified B cell receptor. In an embodiment, as described herein, transcription factors can also be constructed (e.g., on a separate vector) to be part of the modified B cell line(s).

A method for treating a subject that is afflicted with a disease or disorder (e.g., an autoimmune disease, cancer, or infection, etc.) includes administering a therapeutically effective amount of an isolated modified B lymphocyte cell line as disclosed herein. It is recognized that a therapeutically effective amount of cells to be given to a subject can be determined utilizing standard methods for immunotherapy and cell therapy programs.

A method for treating a disease in a vertebrate subject with an immunotherapeutic product as described herein can include isolating from a vertebrate subject exposed to, e.g., by infection, or immunized with at least one second antigen, a B lymphocyte cell line expressing at least one endogenous secreted immunoglobulin reactive to the at least one second antigen; introducing into the isolated B lymphocyte cell line at least one exogenous membrane immunoglobulin reactive to at least one first antigen to produce a recombinant B lymphocyte cell line; and selecting the recombinant B lymphocyte cell line expressing the membrane immunoglobulin reactive to the at least one first antigen and expressing the at least one endogenous secreted immunoglobulin reactive to the at least one second antigen for administration to one or more vertebrate subjects. The method can include administering the at least one first antigen to stimulate the recombinant B lymphocyte cell line; and testing for the presence of the at least one endogenous secreted immunoglobulin reactive to the at least one second antigen in the recombinant B lymphocyte cell line. The method can include administering to the vertebrate subject a pharmaceutical composition including the isolated B lymphocyte cell line; and administering to the vertebrate subject the at least one first antigen to stimulate the isolated B lymphocyte cell line to produce the at least one endogenous secreted immunoglobulin reactive to the at least one second antigen. The method can include confirming the presence of the at least one endogenous secreted immunoglobulin reactive to the at least one second antigen in a bloodstream of the vertebrate subject. The method can include administering the at least one first antigen to stimulate the recombinant B lymphocyte cell line; testing for the presence of the at least one endogenous secreted immunoglobulin reactive to the at least one second antigen; and administering to the vertebrate subject a pharmaceutical composition including the stimulated recombinant B lymphocyte cell line. The recombinant B lymphocyte cell line can be autologous to one of the one or more vertebrate subjects. The recombinant B lymphocyte cell line can be allogeneic to the one or more vertebrate subjects.

A method for producing at least one immunoglobulin in an isolated cell line as described herein can include introducing into at least one isolated B lymphocyte cell line at least one exogenous membrane immunoglobulin reactive to at least one first antigen to produce at least one first isolated B lymphocyte cell line; selecting the at least one first isolated B lymphocyte cell line expressing the membrane immunoglobulin reactive to the at least one first antigen; introducing into the at least one first isolated B lymphocyte cell line at least one exogenous nucleic acid encoding one or more secreted immunoglobulins reactive to at least one second antigen to produce at least one isolated recombinant B lymphocyte cell line; and selecting the at least one isolated recombinant B lymphocyte cell line expressing the one or more secreted immunoglobulin reactive to the at least one second antigen. The method can include selecting the at least one isolated recombinant B lymphocyte cell line expressing the at least one exogenous membrane immunoglobulin reactive to the at least one first antigen. The method can include administering the at least one first antigen to stimulate the at least one isolated recombinant B lymphocyte cell line; and testing for the presence of the one or more secreted immunoglobulins reactive to the at least one second antigen in the at least one isolated recombinant B lymphocyte cell line. The method can include introducing into the at least one first isolated B lymphocyte cell line at least one exogenous membrane immunoglobulin reactive to the at least one second antigen. The method can include introducing into the at least one isolated recombinant B lymphocyte cell line at least one exogenous nucleic acid sequence encoding one or more secreted immunoglobulins reactive to at least one third antigen to produce at least one isolated second recombinant B lymphocyte cell line; and selecting the at least one isolated second recombinant B lymphocyte cell line expressing the at least one secreted immunoglobulin reactive to the at least one second antigen and the at least one secreted immunoglobulin reactive to the at least one third antigen. The method can include administering the at least one first antigen to stimulate the at least one isolated second recombinant B lymphocyte cell line; and testing for the presence of the at least one exogenous secreted immunoglobulin reactive to the at least one third antigen in the recombinant B lymphocyte cell line. In the method, introducing into the at least one isolated B lymphocyte cell line the at least one exogenous membrane immunoglobulin reactive to the at least one first antigen can include introducing at least one exogenous membrane immunoglobulin reactive to the at least one first antigen. Introducing into the at least one isolated B lymphocyte cell line the at least one exogenous membrane immunoglobulin reactive to the at least one first antigen can include introducing an exogenous nucleic acid encoding at least one membrane immunoglobulin reactive to the at least one first antigen. Introducing into the at least one first isolated B lymphocyte cell line the at least one exogenous membrane immunoglobulin reactive to the at least one second antigen can include introducing at least one exogenous membrane immunoglobulin polypeptide reactive to the at least one second antigen. Introducing into the at least one first isolated B lymphocyte cell line the at least one exogenous membrane immunoglobulin reactive to the at least one second antigen can include introducing at least one exogenous nucleic acid encoding at least one membrane immunoglobulin reactive to the at least one second antigen. The method can include exposing the at least one isolated recombinant B lymphocyte cell line to the at least one first antigen, and testing for the activation of the at least one isolated recombinant B lymphocyte cell line to express the exogenous secreted immunoglobulin reactive to the at least one second antigen. The method can include isolating the exogenous secreted immunoglobulin reactive to the at least one second antigen from the at least one isolated recombinant B lymphocyte cell line or from a culture of the at least one isolated recombinant B lymphocyte cell line. In the method, activating the at least one exogenously incorporated membrane immunoglobulin with the first antigen is capable of controlling expression of the at least one exogenously incorporated nucleic acid encoding at least one secreted immunoglobulin reactive to the second antigen. The at least one isolated B lymphocyte cell line can include at least one of naïve B lymphocytes, immature B lymphocytes, transitional B lymphocytes, mature B lymphocytes, follicular B lymphocytes, memory B lymphocytes, plasmablasts, or plasma cells. The at least one isolated B lymphocyte cell line can include at least one memory B lymphocyte.

A method for treating a disease in a vertebrate subject with an immunotherapeutic product as described herein can include introducing into at least one isolated B lymphocyte cell line at least one exogenous membrane immunoglobulin reactive to at least one first antigen to produce at least one first isolated B lymphocyte cell line; selecting the at least one first isolated B lymphocyte cell line expressing the membrane immunoglobulin reactive to the at least one first antigen; introducing into the at least one first isolated B lymphocyte cell line at least one exogenous nucleic acid encoding one or more secreted immunoglobulins reactive to at least one second antigen to produce at least one isolated recombinant B lymphocyte cell line; selecting the at least one isolated recombinant B lymphocyte cell line expressing the secreted one or more immunoglobulin reactive to the at least one second antigens for administration to one or more vertebrate subjects. The method can include selecting the at least one isolated recombinant B lymphocyte cell line expressing the at least one exogenous membrane immunoglobulin reactive to the at least one first antigen. The method can include administering the at least one first antigen to stimulate the at least one isolated recombinant B lymphocyte cell line; and testing for the presence of the one or more secreted immunoglobulin reactive to the at least one second antigen in the at least one isolated recombinant B lymphocyte cell line. The method can include administering to the vertebrate subject a pharmaceutical composition including the at least one isolated recombinant B lymphocyte cell line; and administering to the vertebrate subject the at least one first antigen to stimulate the at least one isolated recombinant B lymphocyte cell line to produce the one or more exogenous secreted immunoglobulin reactive to the at least one second antigen. The method can include confirming the presence of the at least one exogenous secreted immunoglobulin reactive to the at least one second antigen in a bloodstream of the vertebrate subject. The method can include administering the at least one first antigen to stimulate the at least one isolated recombinant B lymphocyte cell line to produce the one or more exogenous secreted immunoglobulin reactive to the at least one second antigen; and administering to the vertebrate subject a pharmaceutical composition including the stimulated at least one isolated recombinant B lymphocyte cell line. The method can include introducing into the at least one first isolated B lymphocyte cell line at least one exogenous membrane immunoglobulin reactive to the at least one second antigen. The method can include introducing into the at least one isolated recombinant B lymphocyte cell line at least one exogenous nucleic acid encoding one or more secreted immunoglobulins reactive to at least one third antigen to produce at least one isolated second recombinant B lymphocyte cell line; and selecting the at least one isolated second recombinant B lymphocyte cell line expressing at least one of the secreted immunoglobulin reactive to the at least one second antigen and the secreted immunoglobulin reactive to the at least one third antigen. The method can include administering to the vertebrate subject a pharmaceutical composition including the at least one isolated second recombinant B lymphocyte cell line; and administering to the vertebrate subject the at least one first antigen to stimulate the at least one isolated second recombinant B lymphocyte cell line to produce the one or more exogenous secreted immunoglobulin reactive to the at least one second antigen and the one or more exogenous secreted immunoglobulin reactive to the at least one third antigen. The method can include confirming the presence of the at least one exogenous secreted immunoglobulin reactive to the at least one second antigen and the one or more exogenous secreted immunoglobulin reactive to the at least one third antigen in a bloodstream of the vertebrate subject. The method can include administering to the vertebrate subject the at least one first antigen to stimulate the at least one isolated second recombinant B lymphocyte cell line to produce the one or more exogenous secreted immunoglobulin reactive to the at least one second antigen and the one or more exogenous secreted immunoglobulin reactive to the at least one third antigen; and administering to the vertebrate subject a pharmaceutical composition including the stimulated at least one isolated second recombinant B lymphocyte cell line. The recombinant B lymphocyte cell line can be autologous to one of the one or more vertebrate subjects. The recombinant B lymphocyte cell line can be allogeneic to the one or more vertebrate subjects.

A method for producing at least one immunoglobulin in an isolated cell line as described herein can include introducing into at least one first isolated B lymphocyte cell line at least one exogenous nucleic acid encoding one or more secreted immunoglobulins reactive to at least one first antigen to produce at least one isolated recombinant B lymphocyte cell line; selecting the at least one isolated recombinant B lymphocyte cell line expressing the one or more secreted immunoglobulin reactive to the at least one first antigen; introducing into the at least one isolated B lymphocyte cell line at least one exogenous membrane immunoglobulin reactive to at least one second antigen to produce at least one first isolated B lymphocyte cell line; and selecting the at least one first isolated B lymphocyte cell line expressing the membrane immunoglobulin reactive to the at least one second antigen.

A method for treating a disease in a vertebrate subject with an immunotherapeutic product as described herein can include introducing into at least one first isolated B lymphocyte cell line at least one exogenous nucleic acid encoding one or more secreted immunoglobulins reactive to at least one first antigen to produce at least one isolated recombinant B lymphocyte cell line; selecting the at least one isolated recombinant B lymphocyte cell line expressing the secreted one or more immunoglobulin reactive to the at least one first antigens; introducing into the at least one isolated B lymphocyte cell line at least one exogenous membrane immunoglobulin reactive to at least one second antigen to produce at least one first isolated B lymphocyte cell line; and selecting the at least one first isolated B lymphocyte cell line expressing the membrane immunoglobulin reactive to the at least one second antigen for administration to the vertebrate subject.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 2A, 2B, 2C are a schematic of a diagrammatic view of nonfunctional and functional immunoglobulin heavy chain genes on chromosomes 14.

FIGS. 3A, 3B, 3C are a schematic of a diagrammatic view of replacement at immunoglobulin loci with heavy chain genes to express membrane IgG and secreted IgG.

FIG. 5 is a schematic of a diagrammatic view of a method for producing an immunoglobulin in an isolated B lymphocyte cell line.

FIG. 6 is a schematic of a diagrammatic view of a method for producing an immunoglobulin in an isolated B lymphocyte cell line.

FIG. 7 is a schematic of a diagrammatic view of a method for producing an immunoglobulin in an isolated B lymphocyte cell line.

DETAILED DESCRIPTION

Figure 1:
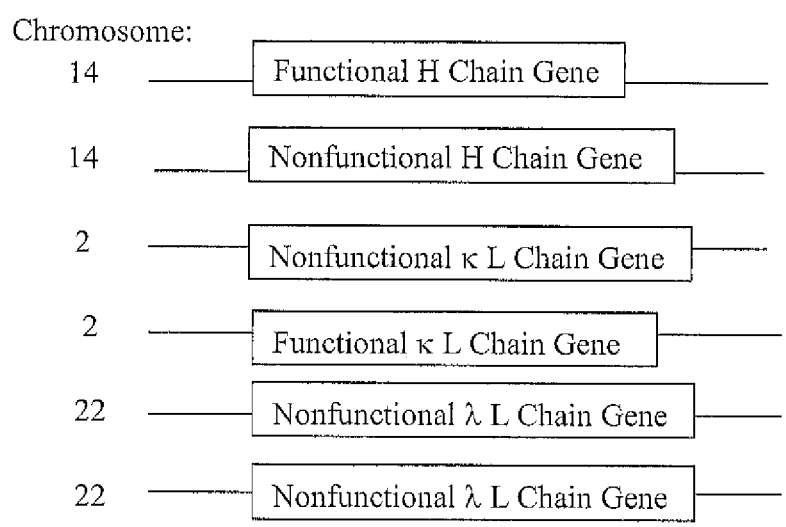
FIG. 1 is a schematic of a diagrammatic view of hypothetical immunoglobulin genes for memory B lymphocytes.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Compositions and methods are disclosed herein for producing one or more immunoglobulins in an isolated B lymphocyte cell line. Compositions and methods are disclosed herein for producing one or more immunoglobulins in the isolated B lymphocyte cell line that direct cell signaling by membrane immunoglobulin in the isolated B lymphocyte cell line. Immune cell therapy in a vertebrate subject can include administering to the vertebrate subject the isolated B lymphocyte cell line that synthesizes secreted immunoglobulins and membrane immunoglobulins each having different target antigens. Immune cell therapy in a vertebrate subject can include administering to the vertebrate subject antigen presenting cells comprised of the isolated B lymphocyte cell line that directs antigen internalization and processing to produce exceptional antigen presenting cells. The isolated B lymphocyte cell line can produce antigen presenting cells that are exceptional or superior at capturing, internalizing and presenting the antigen recognized by the endogenous or exogenously derived membrane immunoglobulin. Compositions and methods are disclosed herein for treating a disease in a vertebrate subject with an immunotherapeutic product. The immunotherapeutic product can include the isolated B lymphocyte cell line having an endogenously-derived or exogenously derived membrane immunoglobulin reactive to a first antigen wherein the isolated B lymphocyte cell line produces one or more secreted immunoglobulins reactive to a second antigen. The immunotherapeutic product can include the isolated B lymphocyte cell line that can be a monoclonal B lymphocyte cell line or polyclonal B lymphocyte cell line that produces one or more secreted antibodies. The immunotherapeutic product can include the isolated B lymphocyte cell line that produces one or more secreted antibodies, e.g., antibodies that recognize different epitopes on the same antigen. The immunotherapeutic product can include the isolated B lymphocyte cell line as one or more antigen presenting cells.

The isolated B lymphocyte cell line can include an immunotherapeutic product administered to a vertebrate subject to develop long-lived isolated B lymphocytes in the vertebrate subject for immune surveillance of chronic disease. The immunotherapeutic product can include the isolated B lymphocyte cell line having an endogenously-derived or exogenously derived membrane immunoglobulin that can be administered to a vertebrate subject to provide an antigen presenting cell to the vertebrate subject.

An isolated cell line as described herein can include an isolated B lymphocyte cell line capable of expressing at least one exogenously incorporated membrane immunoglobulin reactive to a first antigen and at least one endogenous secreted immunoglobulin reactive to a second antigen. The at least one exogenously incorporated membrane immunoglobulin can include an exogenously incorporated membrane immunoglobulin polypeptide. The at least one exogenously incorporated membrane immunoglobulin can include an exogenously incorporated nucleic acid encoding a membrane immunoglobulin polypeptide, wherein the cell line is capable of expressing the membrane immunoglobulin polypeptide.

An isolated recombinant cell line as described herein can include an isolated B lymphocyte cell line capable of expressing at least one exogenously incorporated membrane immunoglobulin reactive to a first antigen and at least one exogenously incorporated nucleic acid encoding secreted immunoglobulin reactive to a second antigen.

A method for producing an immunoglobulin in an isolated B lymphocyte cell line as described herein can include isolating from a vertebrate subject exposed to, e.g., by infection, or immunized with at least one second antigen, a B lymphocyte cell line expressing at least one endogenous secreted immunoglobulin reactive to the at least one second antigen; introducing into the isolated B lymphocyte cell line at least one exogenous membrane immunoglobulin reactive to at least one first antigen to produce a recombinant B lymphocyte cell line; and selecting the isolated B lymphocyte cell line expressing the membrane immunoglobulin reactive to the at least one first antigen and expressing the at least one endogenous secreted immunoglobulin reactive to the at least one second antigen.

A method for treating a disease in a vertebrate subject with an immunotherapeutic product as described herein can include isolating from a vertebrate subject exposed to, e.g., by infection, or immunized with at least one second antigen, a B lymphocyte cell line expressing at least one endogenous secreted immunoglobulin reactive to the at least one second antigen; introducing into the isolated B lymphocyte cell line at least one exogenous membrane immunoglobulin reactive to at least one first antigen to produce a recombinant B lymphocyte cell line; and selecting the recombinant B lymphocyte cell line expressing the membrane immunoglobulin reactive to the at least one first antigen and expressing the at least one endogenous secreted immunoglobulin reactive to the at least one second antigen for administration to one or more vertebrate subjects.

A method for producing at least one immunoglobulin in an isolated cell line as described herein can include introducing into at least one isolated B lymphocyte cell line at least one exogenous membrane immunoglobulin reactive to at least one first antigen to produce at least one first isolated B lymphocyte cell line; selecting the at least one first isolated B lymphocyte cell line expressing the membrane immunoglobulin reactive to the at least one first antigen; introducing into the at least one first isolated B lymphocyte cell line at least one exogenous nucleic acid encoding one or more secreted immunoglobulins reactive to at least one second antigen to produce at least one isolated recombinant B lymphocyte cell line; and selecting the at least one isolated recombinant B lymphocyte cell line expressing the one or more secreted immunoglobulin reactive to the at least one second antigen.

A method for treating a disease in a vertebrate subject with an immunotherapeutic product as described herein can include introducing into at least one isolated B lymphocyte cell line at least one exogenous membrane immunoglobulin reactive to at least one first antigen to produce at least one first isolated B lymphocyte cell line; selecting the at least one first isolated B lymphocyte cell line expressing the membrane immunoglobulin reactive to the at least one first antigen; introducing into the at least one first isolated B lymphocyte cell line at least one exogenous nucleic acid encoding one or more secreted immunoglobulins reactive to at least one second antigen to produce at least one isolated recombinant B lymphocyte cell line; selecting the at least one isolated recombinant B lymphocyte cell line expressing the secreted one or more immunoglobulin reactive to the at least one second antigens for administration to one or more vertebrate subjects.

A method for producing at least one immunoglobulin in an isolated cell line as described herein can include introducing into at least one first isolated B lymphocyte cell line at least one exogenous nucleic acid encoding one or more secreted immunoglobulins reactive to at least one first antigen to produce at least one isolated recombinant B lymphocyte cell line; selecting the at least one isolated recombinant B lymphocyte cell line expressing the one or more secreted immunoglobulin reactive to the at least one first antigen; introducing into the at least one isolated B lymphocyte cell line at least one exogenous membrane immunoglobulin reactive to at least one second antigen to produce at least one first isolated B lymphocyte cell line; and selecting the at least one first isolated B lymphocyte cell line expressing the membrane immunoglobulin reactive to the at least one second antigen.

A method for treating a disease in a vertebrate subject with an immunotherapeutic product as described herein can include introducing into at least one first isolated B lymphocyte cell line at least one exogenous nucleic acid encoding one or more secreted immunoglobulins reactive to at least one first antigen to produce at least one isolated recombinant B lymphocyte cell line; selecting the at least one isolated recombinant B lymphocyte cell line expressing the secreted one or more immunoglobulin reactive to the at least one first antigens; introducing into the at least one isolated B lymphocyte cell line at least one exogenous membrane immunoglobulin reactive to at least one second antigen to produce at least one first isolated B lymphocyte cell line; and selecting the at least one first isolated B lymphocyte cell line expressing the membrane immunoglobulin reactive to the at least one second antigen for administration to the vertebrate subject.

An isolated recombinant cell line includes an isolated B lymphocyte cell line capable of expressing at least one endogenous membrane immunoglobulin reactive to a first antigen and at least one exogenously incorporated nucleic acid encoding at least one secreted immunoglobulin reactive to a second antigen.

In an embodiment, a modified B lymphocyte includes structural or functional features for exhibiting cellular cytotoxicity. For example, in an embodiment, a modified B lymphocyte cell or cell line produces one or more antibodies and has one or more B cell receptors (membrane immunoglobulins as described herein) that are specific to target antigens, such as tumor antigens (including but not limited to, antigens that are mutant forms of "normal" cellular antigens, as well as antigens that are modified by way of post-translational modifications, and antigens that are expressed in an abnormal way or in an abnormal level). In an embodiment, a modified B lymphocyte cell or cell line is capable of mounting a complete immune response with both humoral as well as cellular immune components.

In an embodiment, a modified B lymphocyte that exhibits cytotoxicity is competent to express (directly or indirectly) at least one of perforin, granzymes, and other cytotoxic components. For example, in an embodiment, the B cell receptor (membrane bound immunoglobulin) signals to elicit cytotoxic effectors when engaged with a tumor cell (i.e. the B cell receptor engages with an antigen of a tumor cell). In an embodiment, the modified lymphocyte is competent to secrete an antibody that is cytotoxic (e.g., by way of fixing complement or engaging ADCC [antibody-dependent cell-mediated cytotoxicity]) for the same tumor cell(s).

In an embodiment, a modified B lymphocyte cell is derived from B cells following vaccination with tumor antigens, for example, or from donor peripheral blood lymphocytes by modification of expression of at least one of antibody or B cell receptor (e.g., chimeric B cell receptor or recombinant B cell receptor).

In an embodiment, a modified B lymphocyte cell is modified to express cytotoxicity by way of expression of a recombinant B cell receptor or a chimeric receptor with scFv and membrane immunoglobulin for extracellular transmembrane and cytoplasmic domains along with a cytoplasmic domain from IL21receptor and TLR or another signaling molecule to elicit expression of granzyme, perforin, etc. from the modified B lymphocyte cell.

In an embodiment, a modified B lymphocyte cell is modified to express a recombinant B cell receptor or chimeric B cell receptor specific for a first antigen and an antibody recognizing a second antigen, providing increased specificity as well as increased cellular cytotoxicity and antibody-mediated killing of the target cells (e.g. tumor cells, auto-immune cells, infected cells, inflammatory cells, necrotic cells, regulatory cells (e.g., regulatory T cells, regulatory B cells and myeloid-derived suppressor cells).

In an embodiment, a modified B lymphocyte cell with chimeric B cell receptor or recombinant B cell receptor has been modified to specifically react to one or more target cells, and exhibit cytotoxicity for the one or more target cells. In an embodiment, the modified B lymphocyte cell or cell line is engineered specifically for reaction with one or more tumor cells or tumor cell types. In an embodiment, the modified B lymphocyte cell or cell line is engineered through laboratory techniques and optionally through use of computer data and/or modeling of various components of the B lymphocytes.

In an embodiment, the modified B lymphocyte cell with a chimeric B cell receptor or recombinant B cell receptor includes a modified receptor that is competent to transduce signals that induce expression of cytotoxic effector molecules, when the receptor is engaged.

In an embodiment, the recombinant B cell receptor or chimeric B cell receptor includes a heterologous extracellular, trans-membrane and cytoplasmic signaling domain(s) that elicit expression of cytotoxic effector molecules.

In an embodiment, the recombinant B cell receptor or chimeric B cell receptor includes a cytoplasmic domain derived from at least one of the common gamma chain, IL-21R, a Toll-like receptor (TLR) or CD40. In an embodiment, the recombinant B cell receptor or chimeric B cell receptor is competent to elicit expression of cytotoxic effector molecules, such as perforin, granzyme B, Fas ligand, TRAIL, or others.

In an embodiment, the recombinant B cell receptor or chimeric B cell receptor includes at least one extracellular domain specific for one or more target antigens. In an embodiment, the recombinant B cell receptor or chimeric B cell receptor includes a modified receptor that recognizes a first antigen, and secretes an antibody that recognizes a second antigen. In an embodiment, the recombinant B cell receptor or chimeric B cell receptor includes a modified receptor that recognizes a first epitope of one antigen and secretes an antibody that recognizes a second epitope of the same antigen. Thus, the modified B cells (with recombinant B cell receptor or chimeric B cell receptor) can be designed and engineered by laboratory techniques to be responsive to tumor cells with greater specificity and greater cytotoxic activity.

In an embodiment, the modified B cells that exhibit cytotoxicity are further included in embodiments of B cells described herein that exhibit a chimeric B cell receptor or recombinant B cell receptor specific for one antigen and secrete antibodies specific for a different antigen than its B cell receptor. Such memory B cells can also include the targeted cytotoxicity characteristics as described herein.

In an embodiment, the target cells include cells that have been infected by virus, mycoplasma, bacteria, yeast, or other microorganism. In an embodiment, the target cells include tumor cells, such as primary tumor cells, circulating tumor cells, or metastatic tumor cells. In an embodiment, the target cells include auto-immune cells.

In an embodiment, a method of making the modified B lymphocyte cells includes engineering cells by way of laboratory techniques. In an embodiment, a method of using the modified B lymphocytes for treatment of disease includes administering a therapeutically effective amount of the modified B lymphocyte cells to a subject. Specific examples of methods of making the modified B lymphocyte cells are described in greater detail in the Prophetic Examples section herein.

In an embodiment, a modified B lymphocyte cell or cell line as described herein is engineered, and utilized for administration to a subject for treatment. As described herein, in an embodiment, the subject has active disease. In an embodiment, the subject has chronic disease. In an embodiment, the subject has been exposed to a disease-causing agent and may or may not yet have symptoms of disease. In an embodiment, the subject has latent disease.

A method for producing an immunoglobulin in a recombinant B lymphocyte cell line includes isolating from a vertebrate subject exposed to, e.g., by infection, or immunized with at least one first antigen, a B lymphocyte cell line expressing at least one endogenous membrane immunoglobulin reactive to the at least one first antigen; introducing into the isolated B lymphocyte cell line at least one exogenous nucleic acid encoding at least one of a secreted immunoglobulin reactive to at least one second antigen to produce a recombinant B lymphocyte cell line; and assaying for presence of the at least one exogenous secreted immunoglobulin reactive to the at least one second antigen to select the recombinant B lymphocyte cell line.

A method for treating a disease in a vertebrate subject with an immunotherapeutic product includes isolating from a vertebrate subject exposed to, e.g., by infection, or immunized with at least one first antigen, a B lymphocyte cell line expressing at least one endogenous membrane immunoglobulin reactive to the at least one first antigen; introducing into the isolated B lymphocyte cell line at least one of at least one exogenous nucleic acid encoding at least one secreted immunoglobulin reactive to at least one second antigen; assaying for presence of at least one exogenous secreted immunoglobulin reactive to the at least one second antigen to select the recombinant B lymphocyte cell line for administration to the vertebrate subject.

The isolated B lymphocytes can be used for immunotherapy:

Long-lived isolated B lymphocytes can be used for immune surveillance of chronic disease.

Isolated B lymphocytes having membrane immunoglobulin recognizing antigen can act as exceptional antigen presenting cells to present antigen to T lymphocytes.

Immunotherapy with polyclonal autologous isolated B lymphocytes is a valuable protocol. For example, influenza immune B lymphocytes can be transfected en masse with retroviral vectors. Alternatively, one may immunize with a vaccine and transfect multiple isolated B lymphocytes, e.g., polyclonal B lymphocytes, recognizing different epitopes of the same antigen.

A number of protocols, as presented herein, may be utilized to produce an isolated B lymphocyte cell line as stated in more detail in the detailed description and examples. An isolated B lymphocyte cell line capable of expressing at least one endogenous membrane immunoglobulin reactive to a first antigen or capable of expressing at least one endogenous secreted immunoglobulin reactive to a first antigen can be developed by immunizing an individual with a model antigen, e.g., dinitrophenol (DNP) or an influenza antigen, to elicit memory B cells with endogenous membrane immunoglobulin, e.g., B cell receptors (BCR), reactive to the DNP model antigen or the influenza antigen and/or endogenous soluble immunoglobulin, e.g., antibody reactive to the DNP antigen or the influenza antigen.

An isolated B lymphocyte cell line capable of expressing at least one exogenous secreted immunoglobulin reactive to a broadly neutralizing influenza antigen can be developed by isolating human B cells from an individual who is immune to influenza virus infection and immortalizing the human B cells by infecting the isolated B cells with Epstein Barr virus (EBV). Methods to clone immunoglobulin heavy (H) chain and light (L) chain genes from the EBV-immortalized B lymphocyte cell line may be used. See e.g., U.S. Pat. No. 7,741,077 issued to Grawunder et al. on Jun. 22, 2010 and Early et al., Proc. Natl. Acad. Sci. USA 76: 857-861,1979, which are incorporated herein by reference. To promote homologous recombination the immunoglobulin genes encoding the H chain and L chain for a secreted anti-influenza antibody are cloned in plasmid targeting vectors to obtain targeted integration in the corresponding nonfunctional, germline Ig loci on chromosomes 14 and 2 respectively. Alternatively memory B cells obtained from a patient with a chronic viral infection can be genetically engineered by replacing their functional, expressed Ig genes with exogenous Ig genes encoding a membrane immunoglobulin, e.g., anti-DNP antibody. The Ig H and Ig L chain genes encoding the anti-DNP antibody may be inserted in the functional, expressed Ig gene loci on chromosomes 14 and 2 by using methods of homologous recombination. See e.g., U.S. Pat. Nos. 5,202,238, 6,570,061, and 6,841,383.

Memory B cells expressing anti-DNP membrane IgG can be engineered to express Ig genes encoding a secreted IgG antibody specific for influenza. The anti-influenza $IgG_1$ H chain gene (i.e., $\gamma_1$-H chain gene) may be engineered to remove coding sequences for the membrane spanning domain (TM), the cytoplasmic amino acids (Cyt), and a polyA addition site to yield a $\gamma_1$-H chain gene encoding a secreted H chain only.

To obtain human immunoglobulin (Ig) genes encoding a specific antibody against cancer, e.g., PSA, or for infectious disease, a hybridoma cell line that produces the anti-PSA antibody is constructed. For example transgenic mice with human Ig genes (e.g., XenoMouse® available from Abgenix Inc., Fremont, Calif.) are immunized with PSA and their B cells are fused with a myeloma cell fusion partner, e.g. SP2/0 cells (available from American Type Culture Collection, Manassas, Va.) to create hybridoma cell clones expressing human antibodies (see e.g., U.S. Pat. No. 8,013,128 Ibid.). Supernatants from the hybrid clones are screened using an immunoassay to detect human IgG antibodies which bind PSA protein. Hybridoma clones producing antibodies that recognize PSA are expanded and antibodies from each clone are tested using a Biacore™ A100 instrument (available from GE Healthcare, Piscataway, N.J.) to measure antibody affinity and specificity for PSA (see e.g., GE Healthcare, Application Note 84, "Early kinetic screening of hybridomas . . . " which is incorporated herein by reference). Hybridomas expressing high affinity antibodies for PSA are selected for cloning of their human Ig genes, for example, by homologous recombination.

The engineered immunoglobulin genes encoding a membrane immunoglobulin are expressed in a mammalian cell line and the membrane IgG is purified from the cell line. For example, a kappa (κ) L chain gene and the modified $\gamma$-1 H chain gene are inserted in a lentiviral expression vector using standard recombinant DNA methods (see e.g., U.S. Patent Publication No. 2007/0116690 by Yang et al. published on May 24, 2007 which is incorporated herein by reference). The viral vector is used to transfect Chinese Hamster Ovary (CHO) cells (available from American Type Culture Collection, Manassas, Va.) which are engineered to express the membrane immunoglobulin.

To insure that the recombinant memory B cells are safe for use in patients a suicide gene may be introduced into the B cells. To stop uncontrolled proliferation (and other adverse events) by the recombinant memory B cells, a suicide gene, herpes simplex virus-thymidine kinase gene (HSV-TK) is introduced using a retroviral expression vector. Methods to insert and express the HSV-TK gene and to activate a cytotoxic prodrug such as ganciclovir are known (see e.g., U.S. Pat. No. 6,576,464 issued to Gold and Lebkowski on Jun. 10, 2003 and U.S. Pat. No. 5,997,859 issued to Barber et al. on Dec. 7, 1999 which are incorporated herein by reference). To stop the growth of recombinant B cells deemed unsafe or contributing to an adverse event the B cells expressing HSV-TK are provided with 20 μM ganciclovir (available as Cytovene IV from Roche Laboratories, Nutley, N.J.). Conversion of ganciclovir into a toxic metabolite by the B cells expressing HSV-TK results in their death. Cells not expressing HSV-TK are not harmed by ganciclovir.

The isolated cell line can include an isolated B lymphocyte cell line or an isolated recombinant B lymphocyte cell line that recognizes one or more antigens to an infectious bacterial or viral disease, e.g., influenza antigen. Table 1 includes examples of protocols for constructing the isolated B lymphocyte cell line or the isolated recombinant B lymphocyte cell lines including an exogenously-derived and/or endogenously-derived membrane immunoglobulin and exogenously-derived and/or endogenously-derived secreted immunoglobulin. The secreted immunoglobulin from the isolated recombinant B lymphocyte cell line can include one or more secreted anti-influenza broadly neutralizing antibodies (Flu BNAb). The anti-influenza broadly neutralizing antibodies can be directed to two or more epitopes on the same influenza antigen (Flu BNAb1 and Flu BNAb2). The secreted anti-influenza immunoglobulin from the isolated recombinant B lymphocyte cell line can include one or more secreted polyclonal antibodies (Flu $Ab_n$) to the influenza antigen.

| B lymphocyte cell line | Membrane Immunoglobulin 1 | | Secreted Immunoglobulin 1 | | Membrane Immunoglobulin 2 | | Secreted Immunoglobulin 2 | |
|---|---|---|---|---|---|---|---|---|
| 1 | DNP-KLH | endog | Flu BNAb | exog | Flu BNAb | exog | DNP-KLH | endog |
| 2 | DNP-KLH | exog | Flu BNAb1 | exog | Flu BNAb1 | exog | Flu BNAb2 | exog |
| 3 | DNP-KLH | exog | Flu $Ab_n$ | endog | Flu $Ab_n$ | endog | None | none |
| 4 | Flu $Ab_n$ | endog | Flu $Ab_n$ | endog | Flu BNAb | exog | Flu BNAb | exog |

B lymphocyte protocol 1 is a protocol to produce isolated recombinant B lymphocytes. The protocol 1 immunizes a vertebrate subject with DNP-KLH (dinitrophenyl-Keyhole Limpet Hemocyanin) and select memory B lymphocytes including membrane immunoglobulin recognizing DNP and secreted immunoglobulin recognizing DNP. Anti-DNP B lymphocytes can be transfected with nucleic acid vector including immunoglobulin genes encoding membrane and secreted anti-influenza broadly neutralizing antibody (BNAb).

The isolated recombinant anti-influenza B lymphocytes can be transferred to a vertebrate subject to protect the vertebrate subject from influenza infection. The long-lived anti-influenza B lymphocytes can be activated at will by injecting DNP-KLH into the vertebrate subject when flu symptoms arise or when a pandemic hits.

B lymphocyte protocol 2 is a protocol to produce isolated recombinant B lymphocytes. The protocol 2 isolates memory B lymphocytes from a vertebrate subject. The isolated memory B lymphocytes are transfected with a nucleic acid vector including immunoglobulin genes encoding anti-DNP membrane immunoglobulin only and not anti-DNP secreted immunoglobulin. B lymphocytes with anti-DNP membrane immunoglobulin can be selected and transfected with immunoglobulin genes encoding two anti-influenza BNAbs to two different epitopes of the influenza antigen. The immunoglobulin genes encoding each BNAb can encode membrane and secreted forms of the BNAbs.

The isolated recombinant anti-influenza B lymphocytes can be transferred to a vertebrate subject to protect the vertebrate subject from influenza infection. The long-lived anti-influenza B lymphocytes can be activated at will to produce two anti-influenza BNAbs by injecting DNP-KLH into the vertebrate subject when flu symptoms arise or when a pandemic hits. The long-lived anti-influenza B lymphocytes can also be activated at will to produce two anti-influenza BNAbs by injecting influenza antigen into the vertebrate subject. Unlike Protocol 1, no secreted immunoglobulin to DNP-KLH will be produced when the B lymphocytes are activated by DNP-KLH or by influenza antigen.

B lymphocyte protocol 3 is a protocol to produce polyclonal isolated recombinant B lymphocytes. The protocol 3 immunizes a vertebrate subject with influenza vaccine, e.g., tripartite seasonal influenza vaccine. Memory B lymphocytes that express membrane immunoglobulin recognizing the influenza vaccine antigens are selected in the vertebrate subject. The selected polyclonal anti-influenza memory B lymphocytes are transfected with immunoglobulin genes encoding an anti-DNP membrane immunoglobulin.

The polyclonal anti-influenza B lymphocytes can be transferred to a vertebrate subject to protect the vertebrate subject from influenza infection. The polyclonal, long-lived anti-flu B cells can be activated en mass by injecting DNP-KLH into the vertebrate subject when flu symptoms arise or when a pandemic hits. In addition individual B lymphocyte clones can be activated by their cognate influenza antigen.

B lymphocyte protocol 4 is a protocol to produce polyclonal isolated recombinant B lymphocytes. The protocol 4 immunizes a vertebrate subject with influenza vaccine, e.g., tripartite seasonal vaccine. Memory B lymphocytes that express membrane immunoglobulin recognizing the influenza vaccine antigens are selected in the vertebrate subject. Polyclonal anti-influenza B lymphocytes are transfected with immunoglobulin genes encoding anti-influenza BNAb in both membrane form and secreted form.

The isolated recombinant polyclonal anti-influenza B lymphocytes can be transferred to a vertebrate subject to protect the vertebrate subject from influenza infection. The polyclonal, long-lived anti-influenza B lymphocytes can be activated en mass by injecting a full spectrum of influenza vaccine antigens into the vertebrate subject when flu symptoms arise or when a pandemic hits. Each B lymphocyte produces a BNAb and a clone-specific immunoglobulin reactive with influenza.

In some aspects, the isolated B lymphocyte cell line including at least one exogenously incorporated membrane immunoglobulin activated by the first antigen is capable of controlling expression of the at least one endogenous secreted immunoglobulin reactive to the second antigen. The exogenously incorporated membrane immunoglobulin acts as a receptor to a specified ligand, e.g., the first antigen. Binding of the first antigen to the exogenously incorporated membrane immunoglobulin controls signal transduction through the exogenously incorporated membrane immunoglobulin to control expression from the at least one endogenous secreted immunoglobulin reactive to the second antigen. Binding of the first antigen to the exogenously incorporated membrane immunoglobulin controls signal transduction through the membrane immunoglobulin to control activation of the B lymphocyte or differentiation of the B lymphocyte.

FIG. 1 is a schematic of a diagrammatic view of hypothetical immunoglobulin genes for memory B lymphocytes. Heavy (H) chain gene is on chromosome 14. Kappa (κ) L chain gene is on chromosome 2. Lambda (λ) L chain gene is on chromosome 22. A functional allele and a nonfunctional allele are present on chromosomes 14 and 2. Both λ L chain alleles are depicted as nonfunctional. As shown in Example 3, the immunoglobulin genes encoding the H chain and L chain for an anti-PSA membrane antibody are cloned in targeting plasmid vectors to allow targeted integration in the corresponding nonfunctional Ig loci on chromosomes 14 and 2 respectively.

FIG. 2 is a schematic of a diagrammatic view of non-functional and functional immunoglobulin heavy chain genes on chromosomes 14. The genetic structure of maternal chromosome 14 germline configuration is shown in FIG. 2A. Exons for variable regions ($V_H$), D segments (D), J segments ($J_H$), IgM constant region ($C_H\mu$), secreted tailpiece (TP) and the μ membrane anchor (TM and Cyt) are shown in FIG. 2B. The genetic structure of paternal chromosome 14 functionally rearranged is shown with recombind V, D and J segments ($V_H$ $D_1J_2$) as shown in FIG. 2C. The genetic structure of secreted and membrane μ-H chains encoded and alternate polyadenylation sites are shown. Note that Ig gene structure is simplified with only one constant region ($C_H$) exon shown. Also promoter and enhancer sequences are omitted.

As shown in Example 3, the anti-PCLA immunoglobulin H and L chain genes are integrated into the Ig loci of the mature B cell which are functionally rearranged on chromosomes 14 and 2 respectively. See FIG. 2B for functionally rearranged H chain locus.

FIG. 3 is a schematic of a diagrammatic view of replacement of immunoglobulin genes with heavy chain genes engineered to express membrane IgG and secreted IgG. The genetic structure of secreted and membrane γ-H chain gene with alternate polyadenylation sites are shown in FIG. 3A. The genetic structure of maternal chromosome 14 with an engineered membrane γ-H chain gene is shown in FIG. 3B. The genetic structure of paternal chromosome 14 with an engineered secreted γ-H chain gene is shown in FIG. 3C. Note that Ig gene structure is simplified with only one constant region ($C_H$) exon shown. Also promoter and enhancer sequences are omitted.

As shown in Example 3, the anti-PCLA IgG H chain gene (i.e., γ-H chain gene) may be engineered to remove coding sequences for the membrane spanning domain (TM) and the cytoplasmic amino acids (Cyt) to yield a γ-H chain gene encoding a secreted H chain only (FIG. 3C).

Figure 4A:
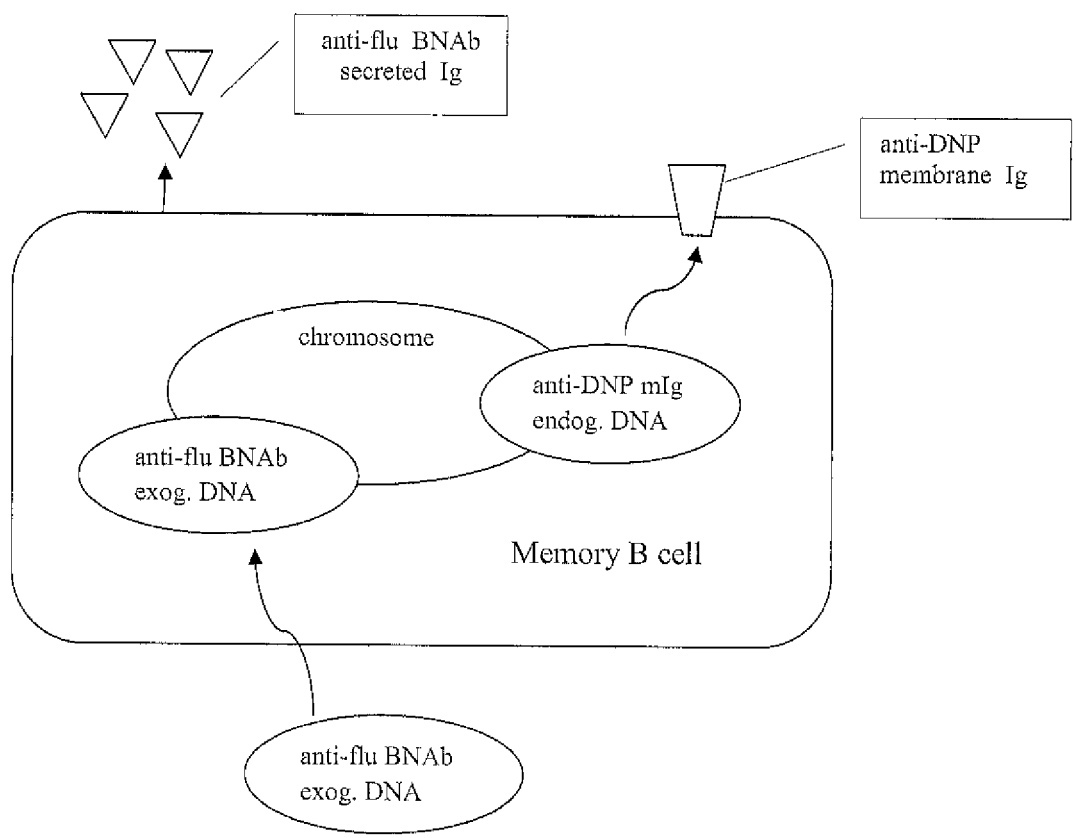
FIGS. 4A, 4B, 4C, 4D are a schematic of a diagrammatic view of protocols to produce recombinant B lymphocytes with membrane immunoglobulin to a first antigen and secreted immunoglobulin to a second antigen.
Figure 4B:
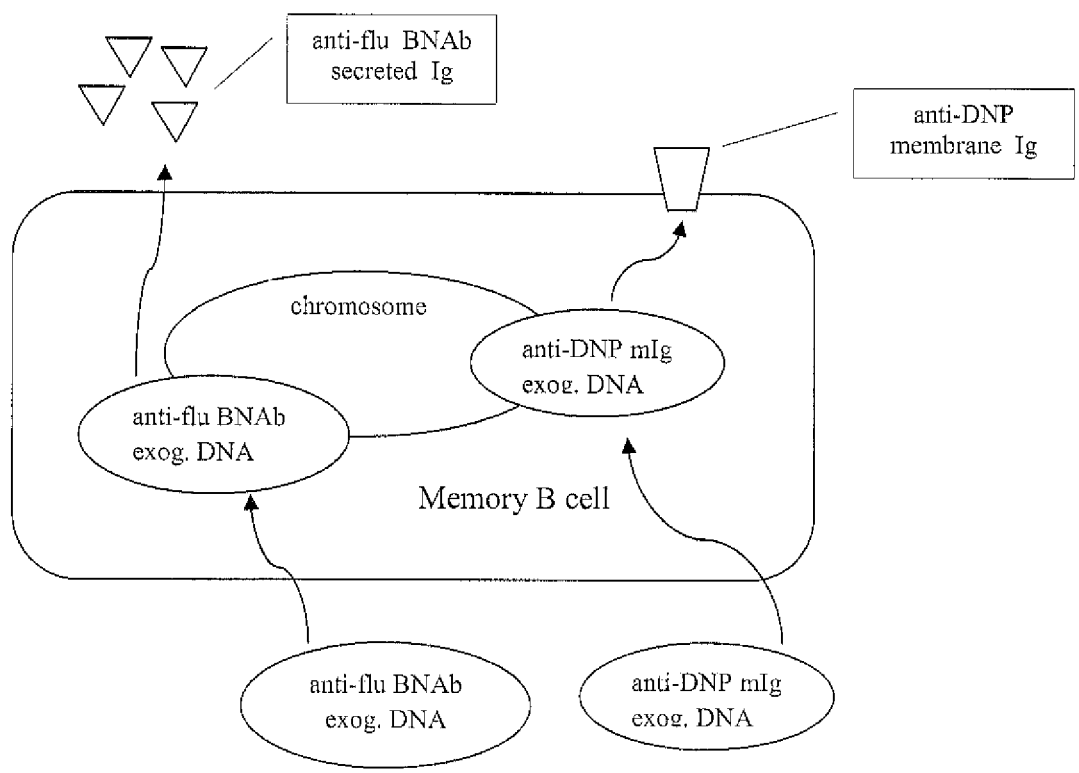
Figure 4C:
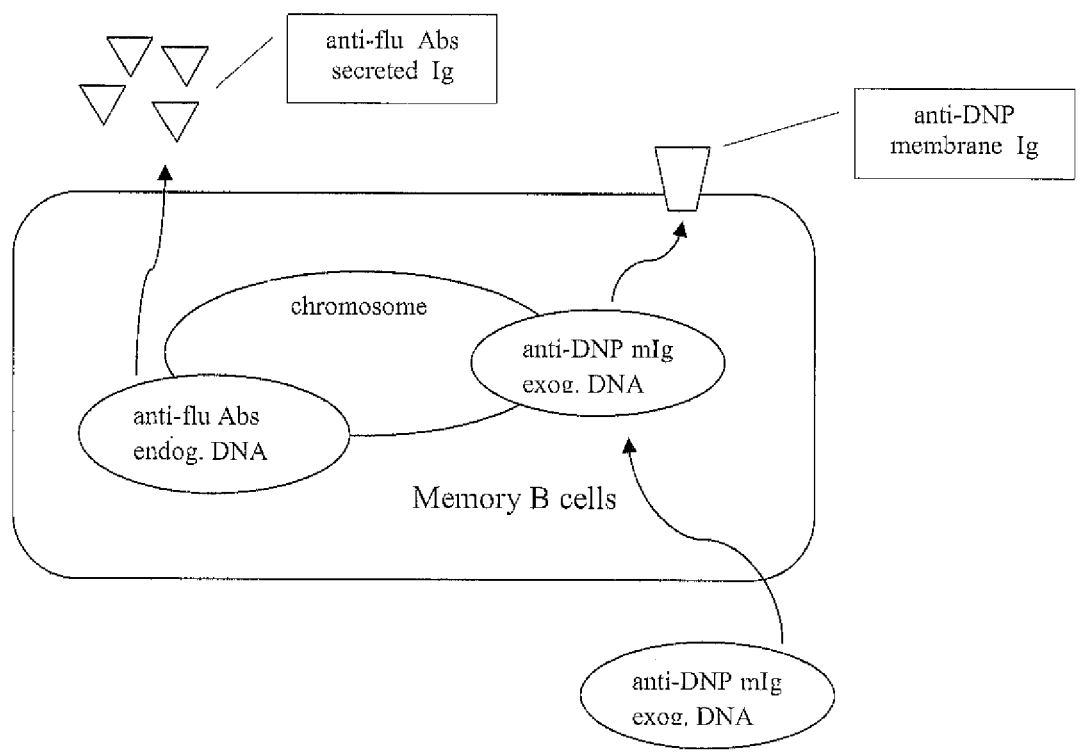
Figure 4D:
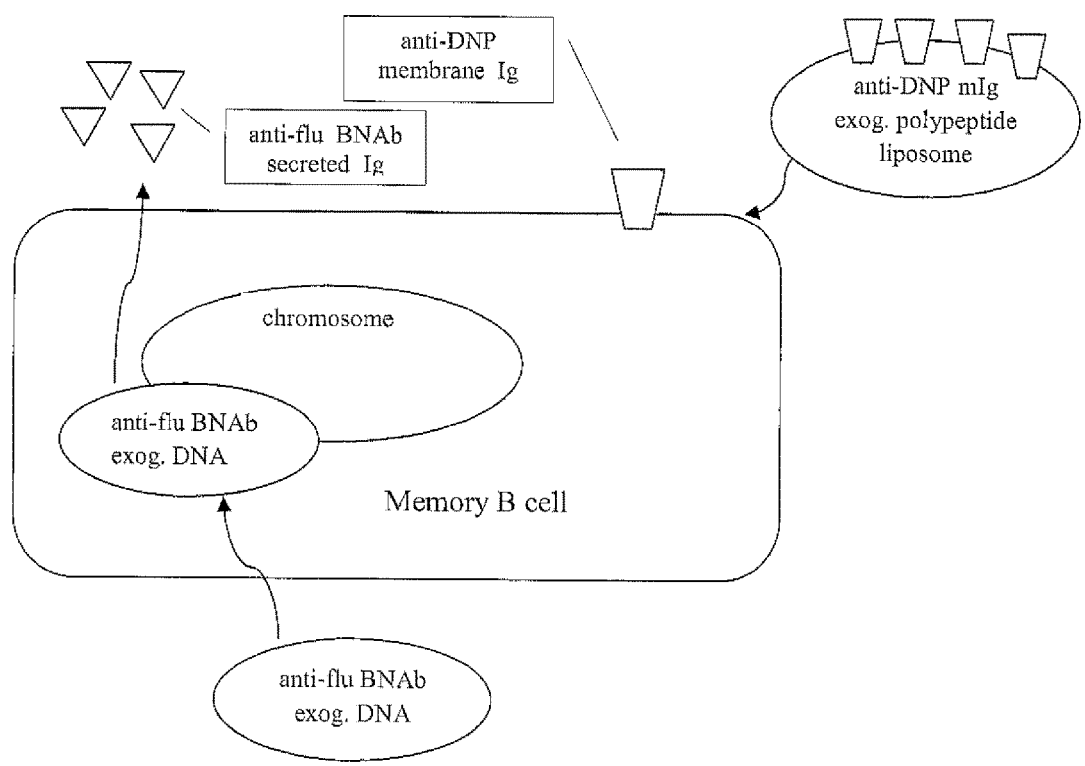

FIGS. 4A, 4B, 4C, 4D are a schematic of a diagrammatic view of protocols to produce recombinant B lymphocytes with membrane immunoglobulin to a first antigen and secreted immunoglobulin to a second antigen. FIG. 4A shows isolated memory B lymphocytes with endogenous DNA encoding anti-DNP membrane immunoglobulin and exogenous DNA encoding anti-Flu broadly neutralizing antibody (BNAb) secreted immunoglobulin. FIG. 4B shows isolated memory B lymphocytes with exogenous DNA encoding anti-DNP membrane immunoglobulin and exogenous DNA encoding anti-Flu broadly neutralizing antibody (BNAb) secreted immunoglobulin. FIG. 4C shows isolated memory B lymphocytes with endogenous DNA encoding anti-Flu Abs secreted immunoglobulin and exogenous DNA encoding anti-DNP membrane immunoglobulin. FIG. 4D shows isolated memory B lymphocytes with exogenous DNA encoding an anti-Flu BNAb secreted immunoglobulin and exogenous anti-DNP membrane immunoglobulin polypeptide delivered with liposomes.

FIG. 5 is a schematic of a diagrammatic view of a method 500 for producing at least one immunoglobulin in an isolated B lymphocyte cell line 501 that includes isolating 502 from a vertebrate subject immunized with at least one second antigen, a B lymphocyte cell line expressing at least one endogenous secreted immunoglobulin reactive to the at least one second antigen; introducing 503 into the isolated B lymphocyte cell line at least one exogenous membrane immunoglobulin reactive to at least one first antigen to produce a recombinant B lymphocyte cell line; selecting 504 the isolated B lymphocyte cell line expressing the membrane immunoglobulin reactive to the at least one first antigen and expressing the at least one endogenous secreted immunoglobulin reactive to the at least one second antigen.

FIG. 6 is a schematic of a diagrammatic view of a method 600 for producing at least one immunoglobulin in an isolated B lymphocyte cell line 601 that includes introducing 602 into at least one isolated B lymphocyte cell line at least one exogenous membrane immunoglobulin reactive to at least one first antigen to produce at least one first isolated B lymphocyte cell line; selecting 603 the at least one first isolated B lymphocyte cell line expressing the membrane immunoglobulin reactive to the at least one first antigen; introducing 604 into the at least one first isolated B lymphocyte cell line at least one exogenous nucleic acid encoding one or more secreted immunoglobulins reactive to at least one second antigen to produce at least one isolated recombinant B lymphocyte cell line; and selecting 605 the at least one isolated recombinant B lymphocyte cell line expressing the one or more secreted immunoglobulin reactive to the at least one second antigen.

FIG. 7 is a schematic of a diagrammatic view of a method 700 for producing at least one immunoglobulin in a recombinant B lymphocyte cell line 701 that includes isolating 702 from a vertebrate subject immunized with at least one first antigen, a B lymphocyte cell line expressing at least one endogenous membrane immunoglobulin reactive to the at least one first antigen; introducing 703 into the isolated B lymphocyte cell line at least one exogenous nucleic acid encoding at least one of a secreted immunoglobulin reactive to at least one second antigen to produce a recombinant B lymphocyte cell line; and assaying 704 for presence of the at least one exogenous secreted immunoglobulin reactive to the at least one second antigen to select the recombinant B lymphocyte cell line.

Figure 8A:
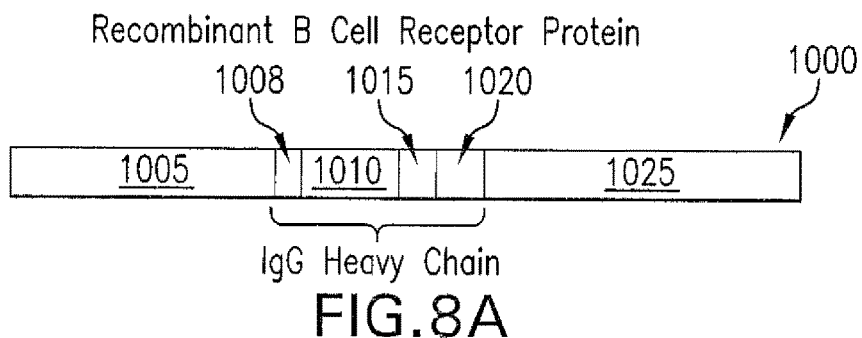
FIG. 8A is a schematic of a diagrammatic view of a recombinant B cell receptor protein.

FIG. 8A illustrates a recombinant B cell receptor protein 1000 with a single-chain variable fragment 1005 joined to IgG heavy chain domains that include a hinge segment 1008, joined to CH3 domain 1010, transmembrane 1015, and cytoplasmic 1020 domains attached to an IL-21 receptor cytoplasmic domain 1025.

Figure 8B:
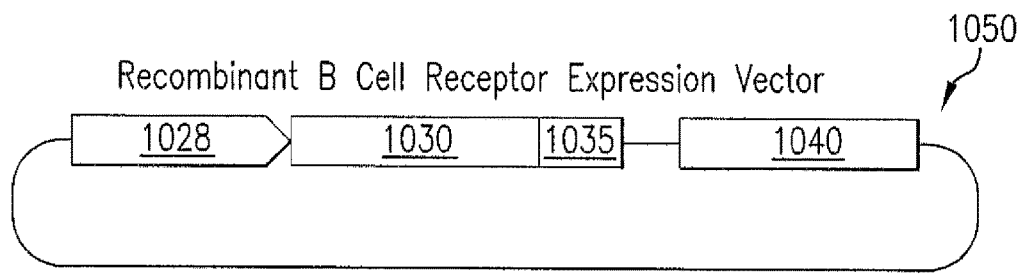
FIG. 8B is a schematic of a diagrammatic view of a recombinant B cell receptor expression vector.

FIG. 8B includes an illustration of a recombinant B cell receptor expression vector 1050 that includes a CMV promoter 1028 joined to a recombinant B cell receptor 1030 attached to a poly-A site 1035 and a neomycin resistance gene 1040.

Figure 8C:
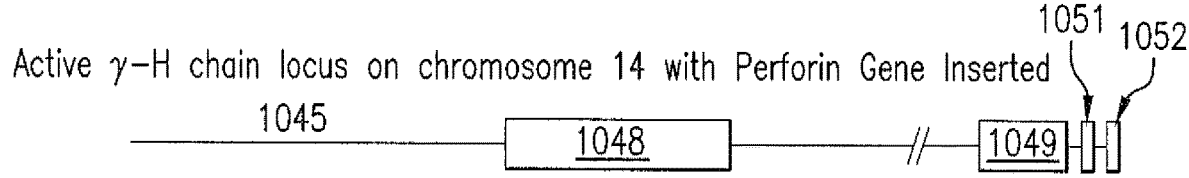
FIG. 8C is a schematic of a diagrammatic view of chromosome 14 with inserted gene.

FIG. 8C is an illustration of an active gamma heavy chain locus on chromosome 14 with perforin gene inserted 1100, including an Ig variable gene promoter 1045 joined to perforin cDNA 1048 and downstream an Ig alpha constant region 1049, with transmembrane domain 1051 and cytoplasmic domain 1052.

Figure 8D:
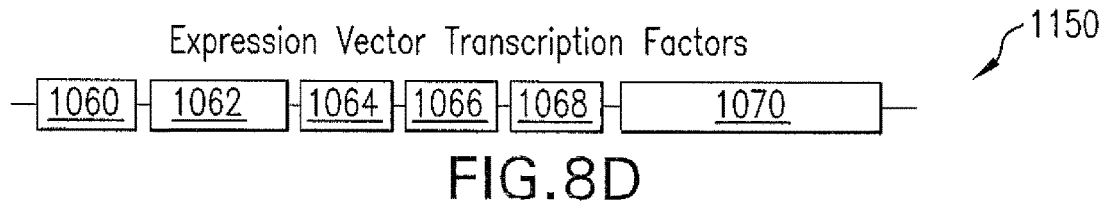
FIG. 8D is a schematic of a diagrammatic view of an expression vector with transcription factors.

FIG. 8D includes an illustration of a Sendai virus expression vector with transcription factor genes inserted 1150 including a viral NP gene 1060 joined to a viral P/V gene 1062, with three transcription factors T-bet 1064, RunX3 1066, and Eomes 1068 with the viral L gene 1070 at the 3-prime end.

In a method for treating a disease in a vertebrate subject with an immunotherapeutic product, the recombinant B lymphocyte cell line may be autologous to one of the one or more vertebrate subjects. Alternatively, in a method for treating a disease in a vertebrate subject with an immunotherapeutic product the recombinant B lymphocyte cell line may be allogeneic to one of the one or more vertebrate subjects. In the case where the recombinant B lymphocyte cell line is allogeneic to one of the one or more vertebrate subjects. In each case when necessary, the recombinant B lymphocyte cell line can be modified to reduce or eliminate expression of MHC Class I (MHC I) proteins or mismatched HLA antigens in the recombinant B lymphocyte cell line to avoid allograft rejection and to reduce or eliminate a graft versus host disease in the recipient of the allogeneic recombinant B lymphocyte cells. See, e.g., U.S. application Ser. No. 12/804,650, and U.S. application Ser. No. 12/804,647, which are incorporated herein by reference.

A vertebrate subject is treated with unmatched, allogeneic donor recombinant B lymphocyte cells engineered to block the presentation of Major Histocompatibility Class I (MHC I) proteins on their cell surface. Allogeneic donor recombinant B lymphocyte cells are transfected with a lentiviral expression vector that directs the expression of a microRNA (miRNA) that inhibits beta2-microglobulin ($\beta_2$M) protein translation and blocks MHC I assembly and presentation on the cell surface. The genetically engineered recombinant B lymphocyte cells are injected into the patient. The inhibition of MHC I production in engrafted recombinant B lymphocyte cells is controlled by a regulatory module and an effector molecule, doxycycline. In the event that the recombinant B lymphocyte cells must be eradicated, doxycycline is administered to repress expression of the miRNA, thereby allowing expression of $\beta_2$M and MHC I on the cell surface and evoking an alloreactive immune response.

A vertebrate subject is treated with recombinant B lymphocyte cells that have reduced expression of Major Histocompatibility Class I (MHC I) proteins on their cell surface, in order to avoid immune rejection of the transplanted cells. The engineered recombinant B lymphocyte cells also contain a suicide mechanism that can be activated by the administration of a prodrug, ganciclovir, in the event of uncontrolled proliferation or other adverse events associated with the recombinant B lymphocyte cells.

A vertebrate subject is treated with a recombinant B lymphocyte cells that are modified to reduce their expression of mismatched HLA antigens and thus avoid allograft rejection. Recombinant B lymphocyte cells are infected with a lentivirus vector encoding microRNA (miRNA) that inhibits the expression of specific donor HLA alleles not shared by the recipient. Production of mismatched HLA-A, -B, -C, -DRBl, and -DQB1 alleles is blocked by miRNAs, and the corresponding HLA proteins are not expressed by the modified donor recombinant B lymphocyte cells.

A vertebrate subject is treated by transplantation with recombinant B lymphocyte cells. Allogeneic recombinant B lymphocyte cells are modified to reduce expression of MHC Class I (MHC I) proteins by expression of a viral gene that targets MHC I proteins for destruction. Recombinant B lymphocyte cells are transduced with a lentiviral expression vector encoding cytomegalovirus (CMV) protein, unique sequence 11 (US11), to target MHC I proteins for destruction and avoid allograft rejection (see e.g., Lin et al., *Cellular and Molecular Immunology* 4: 91-98, (2007), which is incorporated herein by reference).

PROPHETIC EXAMPLES

Example 1

Recombinant Memory B Lymphocytes that Express Two Different Antibodies: 1) a B Cell Receptor (BCR) that Recognizes a Model Antigen, Dinitrophenol-Keyhole Limpet Hemocyanin (DNP-KLH), and 2) a Secreted Antibody that Neutralizes Multiple Strains of Influenza Virus.

An isolated recombinant B lymphocyte cell line that produces a secreted broadly neutralizing immunoglobulin to influenza virus and produces a membrane immunoglobulin to a model antigen can be utilized for cell therapy in a mammalian subject. The recombinant B lymphocyte cell line can be injected into the mammalian subject as cell therapy to provide immunological protection from infection by influenza virus. The recombinant B lymphocyte cell line can be activated in vivo or ex vivo to produce the broadly neutralizing influenza antibody by injecting the mammalian subject (or an in vitro cell culture) with model antigen, dinitrophenol-keyhole limpet hemocyanin (DNP-KLM). The timing to stimulate immunological protection from influenza virus infection in the mammalian subject can be chosen based upon the timing of an outbreak of influenza infection in the population at large.

An individual is immunized with a model antigen, dinitrophenol (DNP), to elicit memory B cells with B cell receptors (BCR) specific for the DNP model antigen. Memory B cells develop in response to immunization with DNP conjugated to a carrier protein, keyhole limpet hemocyanin (KLH). A primary immunization with 1 mg of DNP-KLH (see e.g., Biosearch Technologies DNP-KLH Product Info Sheet which is incorporated herein by reference) is injected subcutaneously in the right arm. See e.g., Rentenaar et al., *Kidney International* 62: 319-328, 2002 which is incorporated herein by reference. Approximately 12-14 days after immunization memory B cells expressing BCR specific for DNP are isolated using dinitrophenol-human serum albumin-biotin (DNP-HSA-biotin) and phycoerythrin-streptavidin (available from Biosearch Technologies, Novato, Calif.) and a fluorescein-anti-CD27 antibody to identify memory B cells. DNP-specific memory B cells are isolated by cell sorting with a fluorescence activated cell sorter (e.g., FACSAriaIII® available from Becton Dickinson, Franklin Lakes, N.J.). For example, see U.S. Pat. No. 7,378,276 issued to Ettinger et al. on May 27, 2008 and U.S. Pat. No. 7,993,864 issued to Brown et al. on Aug. 9, 2011 which are incorporated herein by reference.

Memory B cells expressing BCRs that binds DNP are genetically engineered to express a secreted antibody which is a broadly neutralizing antibody reactive with multiple strains of influenza. Memory B cells expressing anti-DNP BCRs, containing membrane IgG antibodies, have a productively rearranged and expressed membrane immunoglobulin heavy (H) chain gene which resides on chromosome 14 (one of two parental chromosome 14 copies). However, the other parental chromosome 14 has an immunoglobulin (Ig) H chain gene that is not productively rearranged and not expressed. See FIGS. 1, 2A and 2B. This phenomenon, termed "allelic exclusion", yields individual B cells which express only one Ig heavy chain (and one Ig light (L) chain) and thus only one antibody (see e.g., Abbas et al., *Cellular and Molecular Immunology*, 7$^{th}$ Ed., Elsevier Saunders, Philadelphia, Pa., 2012 which is incorporated herein by reference). To create B cells producing two different antibodies the memory B cells expressing anti-DNP BCRs are modified by replacing the non-functional, non-expressed immunoglobulin genes with functional, expressed immunoglobulin genes (for H and L chain). For example, the replacement immunoglobulin genes may encode a secreted antibody, which is a broadly neutralizing anti-influenza antibody.

The immunoglobulin genes encoding a broadly neutralizing antibody reactive with multiple strains of influenza virus may be isolated from the chromosomal DNA of a human B cell clone that produces the antibody. For example human B cells isolated from an individual who is immune to influenza virus infection are immortalized by infecting the isolated B cells with Epstein Barr virus (EBV). Supernatants derived from individual EBV-transformed B cell clones are tested in an immunoassay for antibodies that recognize influenza virus. Methods to immortalize B cells and to detect anti-viral antibodies are described (see e.g., Zhang et al., *Proc. Natl. Acad. Sci. USA* 107: 732-737, 2010 and Corti et al., *J. Clin*. Investigation 120: 1663-1673, 2010 which are incorporated herein by reference).

Methods to clone Ig heavy (H) chain and light (L) chain genes may be used. See e.g., U.S. Pat. No. 7,741,077 issued to Grawunder et al. on Jun. 22, 2010 and Early et al., *Proc. Natl. Acad. Sci. USA* 76: 857-861,1979 which are incorporated herein by reference. For example, an EBV-transformed B cell line expressing a human anti-influenza antibody, $IgG_1$(kappa), is grown in culture and used as a source to isolate messenger RNA (mRNA) and genomic DNA using standard methods employing phenol/chloroform. See e.g., Sambrook et al., In: *Molecular Cloning: A Laboratory Manual*, $2^{nd}$ Ed., Cold Spring Harbor Press, Cold Spring Harbor, N.Y., 1989. The mRNA encoding the $IgG_1$ H chain and the kappa L chain are molecularly cloned following amplification using the polymerase chain reaction (PCR) and reverse transcriptase (RT). Methods and Ig gene primers to amplify Ig H chain mRNA and Ig L chain mRNA are described in U.S. Pat. No. 7,741,077 Ibid. The H and L chain mRNA (amplified as complementary DNA) are cloned in a plasmid vector (e.g., pCR®2.1-TOPO plasmid available from Invitrogen Corp., Carlsbad, Calif.). The DNA sequence of the Ig H chain variable (V) region (including the Vh, D and J segments) and the kappa L chain V-region (including the Vk and Jk segments) are determined. The V-region DNA sequences may be determined by automated DNA sequencing (DNA sequencing services are available from Charles River Laboratories International, Inc., Wilmington, Mass.).

To isolate the corresponding genomic Ig genes, the genomic DNA isolated from the anti-influenza B cell line (see above) is used as a template for PCR amplification of the human H chain gene and kappa L chain gene. PCR primers (oligonucleotides) to amplify the V-region genes, (including their respective promoters and flanking regions upstream (i.e., 5' of the V genes) are determined by searching a human genome database with the V-region DNA sequences established from the cloned Ig mRNA. For example, a human genome nucleotide database available from the National Center for Biotechnology Information can be searched with a computer program, BLAST, for sequences matching the H- and L-chain V-regions. A Human RefSeq Genome database and BLAST software are available online (see e.g., the world wide web at blast.ncbi.nlm.nih.gov/Blast.cgi). Primers to amplify the Ig constant regions, enhancer sequences, the H-chain membrane anchors, poly A addition sites and downstream flanking regions (i.e., 3' of the Ig genes) are described (see e.g., U.S. Pat. No. 7,741,077 Ibid.). The PCR-amplified, genomic fragments can be cloned in a plasmid vector such as pCR®2.1-TOPO available from Invitrogen Corp., Carlsbad, Calif.).

Memory B cells expressing anti-DNP membrane IgG are engineered to express Ig genes encoding a secreted IgG antibody specific for influenza. The anti-influenza $IgG_1$ H chain gene (i.e., $\gamma_1$-H chain gene) may be engineered to remove coding sequences for the membrane spanning domain (TM), the cytoplasmic amino acids (Cyt), and a polyA addition site to yield a $\gamma_1$-H chain gene encoding a secreted H chain only. See FIG. 3C and Abbas et al., Ibid. Ig genes are engineered using standard methods in molecular biology (see e.g., Sambrook et al., In: *Molecular Cloning: A Laboratory Manual*, $2^{nd}$ Ed Cold Spring Harbor Press, Cold Spring Harbor, N.Y., 1989 which is incorporated herein by reference) to remove the membrane exons and to retain the promoter and enhancer sequences associated with the functional anti-influenza Ig genes (see e.g., Abbas et al., Ibid.). The Ig H chain and Ig L chain genes encoding the antiviral antibody may be inserted in the non-expressed Ig gene loci by using methods of homologous recombination (see e.g., U.S. Pat. No. 5,202,238 issued to Perry et al. on Apr. 13, 1993; U.S. Pat. No. 6,570,061 issued to Rajewsky and Zou on May 27, 2003 and U.S. Pat. No. 6,841,383 issued to Reff et al., on Jan. 11, 2005 which are incorporated herein by reference). Methods to identify and target DNA sequences of individual Ig gene loci in the memory B cells are known (see e.g., Suk et al., *Genome Research* published online Aug. 3, 2011. DOI/10.1101/gr.125047.111 which is incorporated herein by reference). DNA sequences determined from the nonexpressed immunoglobulin loci (i.e., nonfunctional immunoglobulin genes) are used to target recombination with the anti-influenza immunoglobulin genes.

To promote homologous recombination the Ig genes encoding the H chain and L chain for a secreted anti-influenza antibody are cloned in plasmid targeting vectors to obtain targeted integration in the corresponding nonfunctional, germline Ig loci on chromosomes 14 and 2 respectively. See FIG. 1 and FIG. 2A. For example, DNA sequences 5' of the $J_H$ segments (see FIG. 2A) are cloned upstream (5') of the anti-influenza $\gamma_1$-H chain gene in a targeting plasmid, and sequences downstream (3') of the µ-H chain membrane anchor exons are cloned downstream (3') of the $\gamma_1$-H chain gene to promote recombination at the germline H-chain locus on chromosome 14. Methods for construction of targeting vectors containing target sequences, replacement genes and selectable markers are described (see e.g., U.S. Pat. No. 5,202,238 Ibid., U.S. Pat. No. 6,570,061 Ibid., and U.S. Pat. No. 6,841,383 Ibid.).

Targeting vectors encoding a secreted anti-influenza antibody are used to replace the nonfunctional, germline µ-H chain gene and the nonfunctional kappa L chain gene in memory B cells expressing membrane anti-DNP IgG. The targeting vector plasmids are linearized by restriction enzyme digestion and transferred by electroporation into the memory B cells followed by selection for the targeting vector plasmids. Methods and reagents for electroporation of primary mammalian cells are described (see e.g., "Electroporation Guide" available from BioRad Inc., Hercules, Calif. which is incorporated herein by reference). Memory B cells, following electroporation, are cultured in tissue culture media containing selection drugs, such as G418 and methotrexate, to select for selectable marker genes, i.e., neomycin resistance gene and dihydrofolate reductase, respectively, present on the H and L chain targeting vectors. Selectable marker genes and their use are described (see e.g., U.S. Pat. No. 6,841,383 Ibid.). Electroporated memory B cells with resistance to both G418 and methotrexate are tested for expression of secreted IgG which binds influenza. Following transfection and selection of the memory B cells, those cells producing secreted IgG antibodies specific for influenza are identified using standard immunoassays to assess B cell supernatants (see e.g., Zhang et al., *Proc. Natl. Acad. Sci. USA* 107: 732-737, 2010 which is incorporated herein by reference).

To insure the recombinant memory B cells are safe for use in patients a suicide gene is introduced into the B cells. To stop uncontrolled proliferation (and other adverse events) by the recombinant memory B cells, a suicide gene, Herpes simplex virus-thymidine kinase gene (HSV-TK) is introduced using a retroviral expression vector. Methods to insert and express the HSV-TK gene and to activate a cytotoxic prodrug such as ganciclovir are known (see e.g., U.S. Pat. No. 6,576,464 issued to Gold and Lebkowski on Jun. 10, 2003 and U.S. Pat. No. 5,997,859 issued to Barber et al. on Dec. 7, 1999 which are incorporated herein by reference). To stop the growth of recombinant B cells deemed unsafe or contributing to an adverse event the B cells expressing HSV-TK are provided with 20 µM ganciclovir (available as Cytovene IV from Roche Laboratories, Nutley, N.J.). Conversion of ganciclovir into a toxic metabolite by the B cells expressing HSV-TK results in their death. Cells not expressing HSV-TK are not harmed by ganciclovir.

The recombinant memory B cells may be activated and expanded in vitro to assess their proliferation, activation and production of the secreted anti-influenza antibody. Engineered anti-DNP memory B cells isolated as described above are cultured with DNP-HSA in vitro to activate the cells. For example, memory B cells at about $10^5$ to $10^6$ cells/mL are cultured in tissue culture flasks in standard media (e.g., RPMI 1640 serum-free media available from Sigma-Aldrich Chem. Co., St. Louis, Mo.) which contain approximately 1 µg/ml of DNP-HSA. Methods to activate memory B cells are described (see e.g., U.S. Pat. No. 7,378,276 Ibid.). To assess activation the cells are tested in a proliferation assay after 3-5 days in culture. Aliquots of the culture are supplemented with $^3$H-thymidine and cultured an additional 16 hours. $^3$H-thymidine uptake is measured by using a liquid scintillation counter (see e.g., U.S. Pat. No. 7,378,276 Ibid.). Equivalent cultures of memory B cells without DNP-HSA serve as negative controls for the proliferation assay. To assess antibody production by the activated memory B cells culture supernatants derived from 3-5 day cultures are tested by enzyme-linked immunosorbent assay (ELISA) to detect and quantitate the anti-influenza antibody. Methods to detect and quantitate anti-influenza antibodies with ELISA are described (see e.g., Khurana et al., *PLoS Med*. published online Apr. 21, 2009; doi:10.1371/journal.pmed.1000049 and Corti et al., *Science* 333: 850-856, 2011 which are incorporated herein by reference). Purified anti-influenza antibody derived from recombinant cell lines (see e.g., Wrammert et al., *Nature* 453: 667-671, 2008 which is incorporated herein by reference) may be used to create standard curves correlating absorbance and antibody concentration in ELISA assays. Supernatants from non-activated, recombinant memory B cells (i.e. cultured without DNP-HA) serve as negative control samples for the anti-influenza antibody ELISA.

The recombinant B lymphocyte cell line can be activated in vivo or ex vivo to produce the secreted broadly neutralizing influenza antibody by injecting the mammalian subject (or an in vitro cell culture) with model antigen, DNP-KLH, to activate production of the secreted antibody from the recombinant B lymphocyte cell line. Timing to stimulate immunological protection from influenza virus infection in the mammalian subject can be chosen based upon the timing of an outbreak of influenza infection in the population at large.

Example 2

Memory B Lymphocytes Engineered to Express a B Cell Receptor (BCR) Recognizing Dinitrophenol (DNP) and a Secreted Antibody Recognizing Hepatitis C Virus.

An isolated recombinant B lymphocyte cell line that produces a secreted immunoglobulin against hepatitis C virus (HCV) and produces a membrane immunoglobulin to a model antigen can be utilized for cell therapy in a mammalian subject. The recombinant B lymphocyte cell line can be injected into the mammalian subject as adoptive cell therapy to provide immunological protection from infection by hepatitis C virus. The recombinant B lymphocyte cell line can be activated in vivo or ex vivo to produce secreted anti-HCV antibody by injecting the mammalian subject (or an in vitro cell culture) with model antigen, dinitrophenol-keyhole limpet hemocyanin (DNP-KLH). Timing to stimulate immunological protection from HCV infection in the mammalian subject can be chosen based upon the timing of exposure of the mammalian subject to HCV or based upon the appearance of symptoms in the subject.

Memory B cells expressing membrane IgG, also known as surface IgG or B cell receptor (BCR), are isolated from the peripheral blood of a patient with a chronic hepatitis C virus (HCV) infection. Polyclonal memory B cells are isolated from the patient's peripheral blood: 1) by isolating peripheral blood mononuclear cells using Ficoll Hypaque density gradients (available from Sigma Aldrich, St. Louis, Mo.); 2) by negative selection of total B cells using magnetic beads (available from Stem Cell Technology, Vancouver, BC), and 3) by labeling the cells with fluorescent monoclonal antibodies that recognize membrane IgG and CD27, a memory B cell marker, and performing fluorescence-activated cell sorting. See for example, U.S. Pat. No. 7,378,276 issued to Ettinger et al. on May 27, 2008 and U.S. Pat. No. 7,993,864 issued to Brown et al. on Aug. 9, 2011 which are incorporated herein by reference.

Immunoglobulin (Ig) genes encoding a membrane IgG antibody specific for DNP may be obtained from healthy volunteers who are immunized with DNP-KLH (see e.g., Biosearch Technologies: DNP-KLH Product Info Sheet which is incorporated herein by reference). Memory B cells with membrane IgG recognizing DNP are isolated by cell sorting with a fluorescence-activated cell sorter (e.g., FACSAriaIII® available from Becton Dickinson, Franklin Lakes, N.J.). For example, see U.S. Pat. No. 7,378,276 Ibid. and U.S. Pat. No. 7,993,864 Ibid. Ig genes encoding an anti-DNP antibody are isolated from individual B cells (see e.g., Tiller et al., *J. Immunol. Methods* 329: 112-124, 2008 which is incorporated herein by reference). For individual anti-DNP B cells the Ig heavy (H) and corresponding Ig light (L) chain gene transcripts are amplified by reverse transcriptase-polymerase chain reaction (RT-PCR) using Superscript®III reverse transcriptase (available from Invitrogen Corp., Carlsbad, Calif.) and Taq DNA polymerase (available from Qiagen, Valencia, Calif.). Reaction conditions and oligonucleotide primers to amplify Ig H chains and Ig L chains are known (see e.g. Tiller et al., Ibid.). The DNA fragments encoding the Ig H and L chain variable (V) region genes are isolated and cloned in mammalian expression vectors containing Ig H and L chain constant region genes (e.g., $C\gamma_1$ and Ck). DNA sequences of the cloned anti-DNP Ig genes ($\gamma_1$-H chain and κ-L chain) are determined using a DNA sequencer (e.g., using a 3130 Genetic Analyzer available from Applied Biosystems, Carlsbad, Calif.). The $IgG_1$ H chain gene (i.e., $\gamma_1$-H chain gene) is engineered to remove the "tail piece" and polyadenylation site encoding the secreted form of the H chain, thus only a membrane $\gamma_1$-H chain is encoded by the engineered gene (see e.g., FIG. 3B, and Abbas et al., *Cellular and Molecular Immunology*, 7$^{th}$ Ed., Elsevier Saunders, Philadelphia, Pa., 2012 which is incorporated herein by reference). For example, the cloned $\gamma_1$-H chain gene may be amplified by PCR with primers that amplify the $\gamma_1$-H chain constant region gene but omit the tail piece and polyadenlyation site encoding the secreted form of the $\gamma_1$-H chain (see FIG. 3B). The primer may also add a RNA splice donor site to the 3' end of the $\gamma_1$-H chain gene and a unique restriction enzyme site (e.g., a site for Not I; enzyme available from New England Biolabs, Ipswich, Mass.). A separate DNA fragment encoding a RNA splice acceptor site, the membrane anchor exons, and the remainder of the $\gamma_1$-H chain gene are PCR-amplified using PCR primers containing restriction enzyme sites which allow reassembly of the $\gamma_1$-H gene encoding a membrane form of the $\gamma_1$-H chain. See FIG. 3B. Methods to amplify and assemble Ig genes are described (see e.g., U.S. Pat. No. 7,741,077 Ibid.).

Memory B cells obtained from a patient with a chronic HCV infection are genetically engineered by replacing their functional, expressed Ig genes with Ig genes encoding a membrane IgG(κ) which recognizes DNP (see above). The Ig H and L chain genes encoding the anti-DNP antibody may be inserted in the functional, expressed Ig gene loci on chromosomes 14 and 2 by using methods of homologous recombination (see e.g., U.S. Pat. No. 5,202,238 issued to Perry et al. on Apr. 13, 1993; U.S. Pat. No. 6,570,061 issued to Rajewsky and Zou on May 27, 2003 and U.S. Pat. No. 6,841,383 issued to Reff et al., on Jan. 11, 2005 which are incorporated herein by reference). To target integration into the functional γ1-H chain locus, targeting sequences from the intron between the $J_H$ cluster and the μ constant region gene ($C_H\mu$; see FIG. 2A) are placed 5' of the anti-DNP γ-H chain gene and sequences downstream from the γ1 membrane anchor exons are placed 3' of the γ-H chain gene (see FIG. 3A). Analogous targeting sequences (i.e., from the Jk-Ck intron and 3' of the Ck gene) are used for targeting the anti-DNP kappa L chain gene into the functional Ck gene. The targeting vectors for anti-DNP H and L chain include selectable marker genes, e.g., hygromycin resistance and histidinol dehydrogenase, respectively. Media containing hygromycin and histidinol are used to select for engineered mature B cells expressing secreted IgG anti-DNP antibody. Essential transcriptional promoter sequences and enhancer sequences necessary for Ig gene expression are retained in the Ig gene integrants (see Abbas et al., Ibid.). Following transfection and selection of the memory B cells, those cells producing membrane IgG antibodies specific for DNP are isolated using DNP-KLH attached to magnetic beads (protocols and separation devices are available from Miltenyi Biotec, Auburn, Calif.).

To create B cells producing two different antibodies the engineered memory B cells expressing an anti-DNP membrane IgG are engineered to replace their non-functional, germline Ig genes with functional Ig genes (for H and L chain). For example, the replacement Ig genes may encode a secreted antibody, an anti-HCV antibody. The Ig genes encoding an anti-viral HCV antibody may be isolated from the chromosomal DNA of a human B cell clone that produces the antiviral antibody. For example, human B cells from an individual immune to HCV are immortalized by infection with Epstein Barr virus (EBV) and supernatants derived from individual B cell clones are tested in an immunoassay for antibodies that recognize HCV. Methods to immortalize B cells and to detect anti-viral antibodies are described (see e.g., Zhang et al., Ibid. and Corti et al., *J. Clin. Investigation* 120: 1663-1673, 2010 which is incorporated herein by reference).

Methods may be used to clone Ig heavy (H) chain and light (L) chain genes. (see e.g., U.S. Pat. No. 7,741,077 issued to Grawunder et al. on Jun. 22, 2010 and Early et al., *Proc. Natl. Acad. Sci. USA* 76: 857-861,1979 which are incorporated herein by reference). For example, an EBV-transformed B cell line expressing a human anti-HCV antibody, IgG$_1$(kappa), is grown in culture and used as a source to isolate messenger RNA (mRNA) and genomic DNA using standard methods employing phenol/chloroform (see e.g., Sambrook et al., In: *Molecular Cloning: A Laboratory Manual*, 2$^{nd}$ Ed., Cold Spring Harbor Press, Cold Spring Harbor, N.Y., 1989). The mRNA encoding the IgG$_1$H-chain and the kappa L-chain are molecularly cloned following amplification using the polymerase chain reaction (PCR) and reverse transcriptase (RT). Methods and Ig gene primers to amplify the H chain and L chain mRNA are described in U.S. Pat. No. 7,741,077 Ibid. The H and L chain mRNA (amplified as complementary DNA) are cloned in a plasmid vector (e.g., pCR®2.1-TOPO plasmid available from Invitrogen Corp., Carlsbad, Calif.) and the DNA sequence of the Ig H chain variable (V) region (including the Vh, D and J segments) and the kappa L chain V-region (including the Vk and Jk segments) are determined. The V-region DNA sequences may be determined by automated DNA sequencing (DNA sequencing services are available from Charles River Laboratories International, Inc., Wilmington, Mass.).

To isolate the corresponding genomic Ig genes, the genomic DNA isolated from the anti-HCV B cell line (see above) is used as a template for PCR amplification of the human H chain gene and kappa L chain gene. PCR primers (oligonucleotides) to amplify the V-region genes, (including their respective promoters and flanking regions upstream (i.e., 5' of the V genes) are determined by searching a human genome database with the V-region DNA sequences established from the cloned Ig mRNA. For example a human genome nucleotide database available from the National Center for Biotechnology Information can be searched with a computer program, BLAST, for sequences matching the H- and L-chain V-regions. A Human RefSeq Genome database and BLAST software are available online (see e.g., http://blast.ncbi.nlm.nih.gov/Blast.cgi). Primers to amplify the Ig constant regions, enhancer sequences, the H-chain membrane anchors, poly A addition sites and downstream flanking regions (i.e., 3' of the Ig gene) are described (see e.g., U.S. Pat. No. 7,741,077 Ibid.). The PCR-amplified, genomic fragments can be cloned in a plasmid vector such as pCR®2.1-TOPO available from Invitrogen Corp., Carlsbad, Calif.). Memory B cells expressing an anti-DNP membrane IgG antibody are engineered to express Ig genes encoding a secreted IgG antibody specific for HCV. The anti-HCV IgG H chain gene (i.e., γ-H chain gene) may be engineered to remove coding sequences for the membrane spanning domain (TM); the cytoplasmic amino acids (Cyt) and a polyA addition site to yield a γ-H chain gene encoding a secreted H chain only. See FIG. 3 and Abbas et al., Ibid. Ig genes are engineered using standard methods in molecular biology (see e.g., Sambrook et al., In: *Molecular Cloning: A Laboratory Manual*, 2$^{nd}$ Ed Cold Spring Harbor Press, Cold Spring Harbor, N.Y., 1989 which is incorporated herein by reference) to remove the membrane exons and to retain the promoter and enhancer sequences associated with the functional anti-HCV Ig genes (see e.g., Abbas et al., Ibid.). The Ig H and L chain genes encoding the antiviral antibody may be inserted in the non-expressed Ig gene loci by using methods of homologous recombination (see e.g., U.S. Pat. No. 5,202,238 Ibid., U.S. Pat. No. 6,570,061 Ibid. and U.S. Pat. No. 6,841,383 Ibid.).

To promote homologous recombination the Ig genes encoding the H chain and L chain for a secreted anti-HCV antibody are cloned in plasmid targeting vectors to obtain targeted integration in the corresponding germline Ig loci on chromosomes 14 and 2 respectively. See FIG. 1. For example, sequences 5' of the $J_H$ segments upstream from the germline μ-H chain gene (see FIG. 2: "Maternal Chromosome 14 Germline Configuration") are cloned upstream (5') of the anti-HCV γ-H chain gene in a targeting plasmid, and sequences downstream (3') of the μ-H chain membrane anchor exons are cloned downstream (3') of the γ-H chain gene to promote recombination at the germline H-chain locus on chromosome 14. Methods for construction of targeting vectors containing target sequences, replacement genes and selectable markers are described (see e.g., U.S. Pat. No. 5,202,238 Ibid., U.S. Pat. No. 6,570,061 Ibid., and U.S. Pat. No. 6,841,383 Ibid.).

Targeting vectors encoding a secreted anti-HCV antibody are used to replace the nonfunctional, germline μ-H chain gene and the nonfunctional kappa L chain gene in memory B cells expressing membrane anti-DNP. The targeting vector plasmids are linearized by restriction enzyme digestion and transferred by electroporation into the memory B cells followed by selection for the targeting vector plasmids. Methods and reagents for electroporation of primary mammalian cells are described (see e.g., "Electroporation Guide" available from BioRad Inc., Hercules, Calif. which is incorporated herein by reference). Memory B cells, following electroporation, are cultured in tissue culture media containing drugs such as G418 and methotrexate to select for selectable marker genes (i.e., neomycin resistance gene and dihydrofolate reductase, respectively) present on the H and L chain targeting vectors. Selectable marker genes and their use are described (see e.g., U.S. Pat. No. 6,841,383 Ibid.). Electroporated memory B cells with resistance to both G418 and methotrexate are tested for expression of secreted IgG which binds HCV. Following transfection and selection of the memory B cells, those cells producing secreted IgG antibodies specific for HCV are identified using standard immunoassays to assess B cell supernatants (see e.g., Zhang et al., *Proc. Natl. Acad. Sci. USA* 107: 732-737, 2010 which is incorporated herein by reference).

The engineered memory B cells expressing two different antibodies may be activated in vitro and assayed for proliferation and production of the secreted anti-HCV antibody. Engineered anti-DNP memory B cells are cultured in vitro with dinitrophenol-human serum albumin (DNP-HSA is available from Biosearch Technologies, Novato, Calif.) to activate the cells. For example, memory B cells at about $10^5$ to $10^6$ cells/mL are cultured at 37° C. in tissue culture flasks in standard media (e.g., RPMI 1640 serum-free media available from Sigma-Aldrich Chem. Co., St. Louis, Mo.) which contain approximately 1 μg/ml of DNP-HSA. In addition, memory B cell cultures may include 1 μg/ml of anti-CD40 antibody and 100 ng/ml of interleukin-21 (both are available from R&D Systems, Minneapolis, Minn.) to activate the cells and promote antibody production. Methods to activate memory B cells are described (see e.g., U.S. Pat. No. 7,378,276 Ibid.). To assess activation the cells are tested in a proliferation assay after 3-5 days in culture. Aliquots of the culture are supplemented with $^3$H-thymidine and cultured an additional 16 hours. $^3$H-thymidine uptake is measured by using a liquid scintillation counter (see e.g., U.S. Pat. No. 7,378,276 Ibid.). Equivalent cultures of memory B cells incubated without DNP-HSA serve as negative controls for the proliferation assay. To assess production of the anti-HCV antibody by the activated memory B cells, culture supernatants derived from approximately 3-5 day cultures are tested by enzyme-linked immunosorbent assay (ELISA) to detect and quantify the anti-HCV antibody. Methods to detect and quantify anti-viral antibodies with ELISA are described (see e.g., Corti et al., *Science* 333: 850-856, 2011 which is incorporated herein by reference). Virions or viral proteins are adsorbed to microtiter plates to capture anti-viral antibodies and a secondary antibody (e.g., anti-IgG) is used to detect the anti-viral antibodies. Anti-viral antibodies in the concentration range of approximately 1 ng/ml to 10,000 ng/ml may be detected using an ELISA. A purified anti-HCV antibody produced by a recombinant cell line (see e.g., Wrammert et al., *Nature* 453: 667-671, 2008 which is incorporated herein by reference) may be used to create standard curves for determining antibody concentration in the ELISA assay. Supernatants from engineered memory B cells that are not activated (i.e. cultured without DNP-HSA) serve as negative control samples for the anti-HCV antibody ELISA.

To insure the engineered memory B cells are safe for use in patients a suicide gene is introduced in the B cells. To stop uncontrolled proliferation (and/or other adverse events) a suicide gene, Herpes simplex virus-thymidine kinase gene (HSV-TK) is introduced into the engineered memory B cells using a retroviral expression vector. Methods to insert and express the HSV-TK gene and to activate a cytotoxic prodrug such as ganciclovir are known (see e.g., U.S. Pat. No. 6,576,464 issued to Gold and Lebkowski on Jun. 10, 2003 and U.S. Pat. No. 5,997,859 issued to Barber et al. on Dec. 7, 1999 which are incorporated herein by reference). If the engineered B cells are deemed unsafe or contributing to an adverse event the B cells expressing HSV-TK are treated with 20 μM ganciclovir (available as Cytovene IV from Roche Laboratories, Nutley, N.J.). Conversion of ganciclovir into a toxic metabolite by the B cells expressing HSV-TK results in their death. Cells not expressing HSV-TK are not harmed by ganciclovir.

Engineered memory B cells expressing an anti-DNP BCR and an anti-viral (anti-HCV) secreted antibody may be expanded and used for adoptive cell therapy of the patient with chronic HCV infection. The B cells may be activated in vitro (as described above) or in vivo by administration of DNP-HSA to the patient. Immunization with approximately 100 mg DNP-KLH administered subcutaneously may be done to activate the engineered memory B cells (see e.g., Rentenaar et al., Ibid.). Multiple activations may be stimulated to respond to HCV infections.

Example 3

Mature B Lymphocytes Engineered to Express a Membrane Antibody Specific for Prostate Specific Antigen and a Second, Secreted Antibody Specific for Prostate Cancer Lipid Antigen.

An isolated recombinant B lymphocyte cell line that produces a secreted immunoglobulin against prostate cancer lipid antigen (PCLA) and produces a membrane immunoglobulin to prostate specific antigen (PSA) can be utilized for cell therapy to treat prostate cancer in a mammalian subject. The recombinant B lymphocyte cell line can be injected into the mammalian subject as adoptive cell therapy to provide immunological reactivity to PSA on prostate cancer cells and to process and present PSA to T lymphocytes. The recombinant B lymphocyte cell line can be activated by endogenous PSA arising in the subject to produce secreted anti-PCLA antibody. The recombinant B lymphocyte cell line can also be activated in vivo or ex vivo by injecting the mammalian subject (or an in vitro cell culture) with exogenous prostate specific antigen (PSA) to produce secreted anti-PCLA antibody. Determination of timing to stimulate immunological reactivity to prostate cancer cells in the mammalian subject can be chosen based upon the detection of prostate cancer cells in the mammalian subject.

Polyclonal mature B cells expressing B cell receptors (BCR) comprised of membrane IgM and IgD are isolated from a prostate cancer patient. Mature B cells may be obtained from peripheral blood leukocytes of the patient. For example approximately $10^9$ leukocytes may be harvested using a leukapheresis procedure (see e.g., Bensinger et al., Blood 81: 3158-3163, 1993 which is incorporated herein by reference) and approximately 5% (i.e., $5 \times 10^7$ cells) are B cells. Mature B cells are isolated from the patient's leukocytes by using antibodies specific for B cell markers CD19, IgD, CD38, and CD21 (available from Becton Dickinson/Pharmingen, San Diego, Calif.). Methods to purify mature B cells using magnetic beads (available from Miltenyi Biotech, Auburn, Calif.) and a fluorescence-activated cell sorter (FACS) are described (see e.g., U.S. Pat. No. 7,378,276 Ibid.). Mature B cells expressing membrane IgM and IgD are cultured in vitro and genetically engineered to express two different antibodies.

Mature B cells are genetically engineered to express a membrane IgG antibody specific for prostate specific antigen (PSA). PSA is a protein antigen associated with prostate cancer that may be produced using recombinant DNA methods and purified for use as an antigen (see e.g., U.S. Pat. No. 8,013,128 issued to Gudas et al. on Sep. 6, 2011 which is incorporated herein by reference). To obtain human immunoglobulin (Ig) genes encoding an antibody specific for PSA a hybridoma cell line that produces the anti-PSA antibody is constructed. For example transgenic mice with human Ig genes (e.g., XenoMouse® available from Abgenix Inc., Fremont, Calif.) are immunized with PSA and their B cells are fused with a myeloma cell fusion partner, e.g. SP2/0 cells (available from American Type Culture Collection, Manassas, Va.) to create hybridoma cell clones expressing human antibodies (see e.g., U.S. Pat. No. 8,013,128 Ibid.). Supernatants from the hybrid clones are screened using an immunoassay to detect human IgG antibodies which bind PSA protein. Hybridoma clones producing antibodies that recognize PSA are expanded and antibodies from each clone are tested using a Biacore™ A100 instrument (available from GE Healthcare, Piscataway, N.J.) to measure antibody affinity and specificity for PSA (see e.g., GE Healthcare, Application Note 84, "Early kinetic screening of hybridomas . . . ", which is incorporated herein by reference). Hybridomas expressing high affinity antibodies for PSA are selected for cloning of their human Ig genes. Methods to clone Ig heavy (H) chain and light (L) chain genes may be used. See e.g., U.S. Pat. No. 7,741,077 issued to Grawunder et al. on Jun. 22, 2010 and Early et al., *Proc. Natl. Acad. Sci. USA* 76: 857-861,1979 which are incorporated herein by reference. For example, a hybridoma cell line expressing a human anti-PSA antibody, $IgG_1$(kappa), is grown in culture and used as a source to isolate messenger RNA (mRNA) and genomic DNA using standard methods employing phenol/chloroform (see e.g., Sambrook et al., In: *Molecular Cloning: A Laboratory Manual*, $2^{nd}$ Ed., Cold Spring Harbor Press, Cold Spring Harbor, N.Y., 1989). The mRNA encoding the $IgG_1$ H-chain and the kappa L-chain are molecularly cloned following amplification using the polymerase chain reaction (PCR) and reverse transcriptase (RT). Methods and Ig gene primers to amplify the H chain and L chain mRNA are described in U.S. Pat. No. 7,741,077 Ibid. The H and L chain mRNA (amplified as complementary DNA) are cloned in a plasmid vector (e.g., pCR®2.1-TOPO plasmid available from Invitrogen Corp., Carlsbad, Calif.) and the DNA sequence of the Ig H chain variable (V) region (including the Vh, D and J segments) and the kappa L chain V-region (including the Vk and Jk segments) are determined. The V-region DNA sequences may be determined by automated DNA sequencing (DNA sequencing services are available from Charles River Laboratories International, Inc., Wilmington, Mass.). To isolate the corresponding genomic Ig genes, the genomic DNA isolated from the anti-PSA hybridoma (see above) is used as a template for PCR amplification of the human H chain gene and kappa L chain gene. PCR primers (oligonucleotides) to amplify the V-region genes, (including their respective promoters and flanking regions upstream (i.e., 5' of the V genes) are determined by searching a human genome database with the V-region DNA sequences established from the cloned Ig mRNA. For example a human genome nucleotide database available from the National Center for Biotechnology Information can be searched with a computer program, BLAST, for sequences matching the H- and L-chain V-regions. A Human RefSeq Genome database and BLAST software are available online (see e.g., the world wide web at blast.ncbi.nlm.nih.gov/Blast.cgi). Primers to amplify the Ig constant regions, enhancer sequences, the H-chain membrane anchors, poly A addition sites and downstream flanking regions (i.e., 3' of the Ig gene) are described (see e.g., U.S. Pat. No. 7,741,077 Ibid.). The PCR-amplified, genomic fragments can be cloned in a plasmid vector such as pCR®2.1-TOPO available from Invitrogen Corp., Carlsbad, Calif.). The $IgG_1$ H chain gene (i.e., $\gamma_1$-H chain gene) may be engineered to remove the "tail piece" and polyadenylation site encoding the secreted form of the H chain, thus only a membrane $\gamma_1$-H chain is encoded by the engineered gene (see e.g., FIG. 3, and Abbas et al., *Cellular and Molecular Immunology*, $7^{th}$ Ed., Elsevier Saunders, Philadelphia, Pa., 2011 which is incorporated herein by reference). For example, the cloned $\gamma_1$-H chain gene may be amplified by PCR with primers that amplify the $\gamma_1$-H chain constant region gene but omit the tail piece and polyadenlyation site encoding the secreted form of the $\gamma_1$-H chain. The primer may also add a RNA splice donor site to the 3' end of the $\gamma_1$-H chain gene and a unique restriction enzyme site (e.g., a site for Not I; enzyme available from New England Biolabs, Ipswich, Mass.). Separate DNA fragments encoding the membrane anchor exons and the remainder of the $\gamma_1$-H chain gene are PCR-amplified using PCR primers containing restriction enzyme sites which allow reassembly of the $\gamma_1$-H gene encoding a membrane form of the $\gamma_1$-H chain. See FIG. 3. Methods to amplify and assemble Ig genes are described (see e.g., U.S. Pat. No. 7,741,077 Ibid.).

The Ig genes encoding the H chain and L chain for an anti-PSA membrane antibody are cloned in plasmid targeting vectors to obtain targeted integration in the corresponding nonfunctional germline Ig loci on chromosomes 14 and 2 respectively. See FIG. 1. For example, sequences 5' of the $J_H$ genes (see FIG. 2A) are cloned upstream (5') of the anti-PSA $\gamma_1$-H chain gene in a targeting plasmid, and sequences downstream (3') of the µ-H chain membrane anchor exons (TM and Cyt) are cloned downstream (3') of the $\gamma_1$-H chain gene to promote recombination at the germline H-chain locus on chromosome 14. Methods for construction of targeting vectors containing target sequences, replacement genes and selectable markers are described (see e.g., U.S. Pat. No. 5,202,238 issued to Perry et al. on Apr. 13, 1993; U.S. Pat. No. 6,570,061 issued to Rajewsky and Zou on May 27, 2003, and U.S. Pat. No. 6,841,383 issued to Reff et al. on Jan. 11, 2005 which are incorporated herein by reference). Targeting vectors constructed to replace the nonfunctional germline chain gene and the nonfunctional kappa L chain gene in mature B cells are transferred into mature B cells in vitro. The targeting vector plasmids are linearized by restriction enzyme injection and transferred by electroporation into the mature B cells followed by selection for the targeting vector plasmids. Methods and reagents for electroporation of primary mammalian cells are described (see e.g., "Electroporation Guide" available from BioRad Inc., Hercules, Calif. which is incorporated herein by reference). Mature B cells, following electroporation are cultured in tissue culture media containing drugs such as G418 and methotrexate to select for selectable marker genes (i.e., neomycin resistance gene and dihydrofolate reductase, respectively) present on the H and L chain targeting vectors. Selectable marker genes and their use are described (see e.g., U.S. Pat. No. 6,841,383 Ibid.) Electroporated mature B cells with resistance to both G418 and methotrexate are tested for expression of membrane IgG which binds PSA. For example, engineered mature B cells expressing membrane IgG specific for PSA are isolated using magnetic beads with PSA attached, and the cells are propagated in vitro prior to transfection with Ig genes for a second antibody specific for a different prostate tumor associated antigen.

Mature B cells expressing an anti-PSA membrane IgG antibody are engineered to express Ig genes encoding a secreted IgG antibody specific for prostate cancer lipid antigen (PCLA). Methods to extract PCLA and to obtain a monoclonal antibody specific for PCLA are known (see e.g., Zhang et al., *Proc. Natl. Acad. Sci. USA* 107: 732-737, 2010 which is incorporated herein by reference). A human IgG antibody specific for PCLA and the corresponding Ig genes may be obtained as described above (see e.g., U.S. Pat. No. 7,741,077 Ibid. and Early et al., Ibid.). The anti-PCLA IgG H chain gene (i.e., γ-H chain gene) may be engineered to remove coding sequences for the membrane spanning domain and the cytoplasmic amino acids to yield a γ-H chain gene encoding a secreted H chain only. See FIG. 3 and Abbas et al., Ibid. The anti-PCLA Ig genes are integrated into the functionally rearranged Ig gene loci of the mature B cell which include the μ-H chain gene on chromosome 14 and the kappa L chain gene on chromosome 2 (e.g., see FIG. 2; only the H chain gene is shown). Targeted integration of the anti-PCLA γ-H chain gene and L chain gene into the corresponding functional H and L chain gene loci (i.e. chromosomes 14 and 2 respectively) is done using methods of homologous recombination as described above (see U.S. Pat. No. 6,570,061 Ibid., and U.S. Pat. No. 6,841,383 Ibid.). To target integration into the functional μ-H chain locus, targeting sequences from the intron between the $J_H$ cluster and the μ constant region gene ($C_H\mu$) are placed 5' of the anti-PCLA γ-H chain gene and sequences downstream from the μ membrane anchor exons are placed 3' of the γ-H chain gene (see FIG. 2). Analogous targeting sequences (i.e., from the Jk-Ck intron and 3' of the Ck gene) are used for targeting the anti-PCLA kappa light chain gene to the functional Ck gene. The targeting vectors for anti-PCLA H and L chain include different selectable marker genes, hygromycin resistance and histidinol dehydrogenase, respectively. Media containing hygromycin and histidinol is used to select for engineered mature B cells expressing secreted IgG anti-PCLA antibody. Essential transcriptional promoter sequences and enhancer sequences necessary for Ig gene expression are retained in the Ig gene integrants (see Abbas et al., Ibid.). Following transfection and selection of the mature B cells, those cells producing secreted IgG antibodies specific for PCLA are identified using standard immunoassays to assess B cell supernatants (see e.g., Zhang et al., Ibid.). The engineered mature B cells are cultured in vitro and stimulated with PSA to activate the cells and to stimulate secretion of anti-PCLA IgG antibodies.

To insure the engineered mature B cells are safe for use in patients a suicide gene is introduced in the B cells. To stop uncontrolled proliferation (and/or other adverse events) a suicide gene, Herpes simplex virus-thymidine kinase gene (HSV-TK) is introduced into the engineered memory B cells using a retroviral expression vector. Methods to insert and express the HSV-TK gene and to activate a cytotoxic prodrug such as ganciclovir are known (see e.g., U.S. Pat. No. 6,576,464 issued to Gold and Lebkowski on Jun. 10, 2003 and U.S. Pat. No. 5,997,859 issued to Barber et al. on Dec. 7, 1999 which are incorporated herein by reference). If the engineered B cells are deemed unsafe or contributing to an adverse event the B cells expressing HSV-TK are treated with 20 μM ganciclovir (available as Cytovene IV from Roche Laboratories, Nutley, N.J.). Conversion of ganciclovir into a toxic metabolite by the B cells expressing HSV-TK results in their death. Cells not expressing HSV-TK are not harmed by ganciclovir.

The isolated recombinant B lymphocytes are administered to prostate cancer patients to provide antibodies to PCLA and to process and present PSA to T cells. Autologous B cells engineered to express anti-PSA membrane IgG and anti-PCLA secreted IgG are cultured in vitro with approximately 1 μg/mL PSA for approximately 3 to 5 days and then washed in serum-free media prior to injection. Approximately $5-10 \times 10^8$ B cells are injected intravenously and the concentration of anti-PCLA antibodies and the number of engineered B cells in the peripheral blood of the patient are monitored with immunoassays and flow cytometry respectively.

Example 4

Memory B Lymphocytes from Patients Vaccinated with Influenza Vaccine are Provided with Membrane Antibodies Specific for DNP and Activated by Administration of DNP-HSA.

An isolated recombinant B lymphocyte cell line that produces a secreted broadly neutralizing immunoglobulin to influenza virus and produces a membrane immunoglobulin to a model antigen can be utilized for cell therapy in a mammalian subject. The recombinant B lymphocyte cell line can be injected into the mammalian subject as cell therapy to provide immunological protection from infection by influenza virus. The recombinant B lymphocyte cell line can be activated in vivo or ex vivo to produce the broadly neutralizing influenza antibody by injecting the mammalian subject (or an in vitro cell culture) with model antigen, dinitrophenol-keyhole limpet hemocyanin (DNP-KLH). The timing to stimulate immunological protection from influenza virus infection in the mammalian subject can be chosen based upon the timing of an outbreak of influenza infection in the population at large.

An individual is immunized with an influenza vaccine to obtain memory B cells with B cell receptors (BCR) specific for influenza virus. Memory B cells develop in response to immunization with a subunit vaccine for influenza virus which may elicit broadly neutralizing antibodies (see e.g., Ekiert et al., *Science* 324: 246-251, 2009 which is incorporated herein by reference). A primary immunization with 1 mg of influenza virus vaccine, for example, a conserved epitope from the viral hemagglutinin (HA) protein is injected subcutaneously in the right arm. Approximately 12-14 days after immunization memory B cells expressing BCR specific for influenza are isolated using influenza HA protein-biotin and phycoerythrin (PE)-streptavidin and a fluorescein-anti-CD27 antibody to identify memory B cells (biotin, streptavidin and antibodies are available from Becton Dickinson/Pharmingen, San Diego, Calif.). Influenza-specific memory B cells are isolated by cell sorting with a fluorescence activated cell sorter (e.g., FACSAriaIII® available from Becton Dickinson, Franklin Lakes, N.J.). For example, see U.S. Pat. No. 7,378,276 issued to Ettinger et al. on May 27, 2008 and U.S. Pat. No. 7,993,864 issued to Brown et al. on Aug. 9, 2011 which are incorporated herein by reference. Memory B cells expressing membrane IgG specific for an influenza HA epitope are cultured in vitro and expanded prior to transfection with a membrane immunoglobulin specific for dinitrophenol (DNP). For example, memory B cells at about $10^5$ to $10^6$ cells/mL are cultured at 37° C. in tissue culture flasks in standard media (e.g., RPMI 1640 serum-free media available from Sigma-Aldrich Chem. Co., St. Louis, Mo.) which contain approximately 1 μg/ml of influenza HA peptide (see e.g., Ekiert et al., Ibid.) In addition, memory B cell cultures may include 1 μg/ml of anti-CD40 antibody and 100 ng/ml of interleukin-21 (both are available from R&D Systems, Minneapolis, Minn.) to activate the cells (see e.g., U.S. Pat. No. 7,378,276 Ibid.). A membrane immunoglobulin specific for DNP is produced using recombinant DNA methods and inserted in the membrane of memory B cells producing anti-influenza antibodies. Immunoglobulin (Ig) genes encoding a membrane IgG antibody specific for DNP may be obtained from healthy volunteers who are immunized with DNP-KLH (see e.g., Biosearch Technologies DNP-KLH Product Info Sheet which is incorporated herein by reference). Memory B cells with membrane IgG recognizing DNP are isolated by cell sorting with a fluorescence-activated cell sorter (e.g., FACSAriaIII® available from Becton Dickinson, Franklin Lakes, N.J.). For example, see U.S. Pat. No. 7,378,276 Ibid. and U.S. Pat. No. 7,993,864 Ibid.

Immunoglobulin genes encoding an anti-DNP antibody are isolated from individual B cells (see e.g., Tiller et al., *J. Immunol. Methods* 329: 112-124, 2008 which is incorporated herein by reference). For each individual anti-DNP B cell the Ig heavy (H) and corresponding Ig light (L) chain gene transcripts are amplified by reverse transcriptase-polymerase chain reaction (RT-PCR) using Superscript®III reverse transcriptase (available from Invitrogen Corp., Carlsbad, Calif.) and Taq DNA polymerase (available from Qiagen, Valencia, Calif.). Reaction conditions and oligonucleotide primers to amplify Ig H chains and Ig L chains are known (see e.g. Tiller et al., Ibid.). The DNA fragments encoding the Ig H and Ig L chain variable (V) region genes are isolated and cloned in mammalian expression vectors containing Ig H and Ig L chain constant region genes (e.g., Cγ1 and Ck). DNA sequences of the cloned anti-DNP Ig genes (γ1-H chain and κ-L chain) are determined using a DNA sequencer (e.g., using a 3130 Genetic Analyzer available from Applied Biosystems, Carlsbad, Calif.). The $IgG_1$ H chain gene (i.e., $\gamma_1$-H chain gene) is engineered to remove the "tail piece" and polyadenylation site encoding the secreted form of the H chain, thus only a membrane $\gamma_1$-H chain is encoded by the engineered gene (see e.g., FIG. 3B, and Abbas et al., *Cellular and Molecular Immunology,* $7^{th}$ Ed Elsevier Saunders, Philadelphia, Pa., 2012 which is incorporated herein by reference). For example, the cloned $\gamma_1$-H chain gene may be amplified by PCR with primers that amplify the $\gamma_1$-H chain constant region gene but omit the tail piece and polyadenlyation site encoding the secreted form of the $\gamma_1$-H chain. A separate DNA fragment encoding the $\gamma_1$ membrane anchor exons, and the remainder of the $\gamma_1$-H chain gene are PCR-amplified using PCR primers containing restriction enzyme sites which allow reassembly of the $\gamma_1$-H gene encoding a membrane form of the $\gamma_1$-H chain. See FIG. 3B. Methods to amplify and assemble Ig genes are described (see e.g., U.S. Pat. No. 7,741,077 Ibid.).

The genetically engineered immunoglobulin genes encoding the anti-DNP membrane antibody are expressed in a mammalian cell line and the membrane IgG is purified from the cell line. For example, a kappa (κ) L chain gene and the modified γ-1 H chain gene are inserted in a lentiviral expression vector using standard recombinant DNA methods (see e.g., U.S. Patent Publication No. 2007/0116690 by Yang et al. published on May 24, 2007 which is incorporated herein by reference). The viral vector is used to transfect Chinese Hamster Ovary (CHO) cells (available from American Type Culture Collection, Manassas, Va.) which are engineered to express membrane immunoglobulin. Methods to express membrane immunoglobulins may be used. See e.g., Price et al., *J. Immunol. Methods* 343: 28-41, 2009 which is incorporated herein by reference. To identify and isolate CHO clones expressing the anti-DNP membrane IgG a phycoerythrin-conjugated anti-human IgG antibody was used to label CHO cells and sort them using FACS (see e.g., Price et al., Ibid.). A CHO cell line producing anti-DNP membrane IgG is isolated and expanded and membrane IgG is purified from CHO cell lysates using an immunoaffinity column. An affinity column constructed from protein A-Sepharose (available from Sigma-Aldrich Co., St. Louis, Mo.) is used to purify membrane IgG from lysates of the engineered CHO cells. For example cells may be lysed in a buffer containing: 0.15 M NaCl, 0.01 M TrisHCl, pH 8.2, 1 mM EDTA, 2 mM phenylmethylsulfonyl fluoride, 0.5% Nonidet P-40 and 1 mg/mL HSA (see e.g., Schneider et al., *J. Biol. Chem.* 257: 10766-10769, 1982 which is incorporated herein by reference). The purified anti-DNP membrane IgG is used to construct liposomes which are fused to memory B cells specific for influenza antigen (see above).

Liposomes containing anti-DNP membrane IgG are constructed from phospholipids and purified anti-DNP membrane IgG antibodies. The liposomes with incorporated anti-DNP membrane IgG antibodies may be fused with memory B cells specific for influenza virus to obtain memory B cells with anti-DNP membrane immunoglobulin incorporated into the B cell membrane. Liposomes may be prepared from cholesterol and L-α-phosphatidylcholine. See e.g., U.S. Patent Publication No. 2005/0208120, which is incorporated herein by reference. Cholesterol and L-α-phosphatidyl choline are combined at a molar ratio of 2:7 in chloroform and the chloroform is evaporated away using an argon stream. The liposomes are resuspended in a 140 mM NaCl, 10 mM Tris HCl, 0.5% deoxycholate at pH 8 and sonicated for three minutes. Purified anti-DNP membrane antibodies (see above) are inserted into the liposomes by combining the membrane IgG with liposomes at a 1:10 molar ratio and dialyzing for 72 hours at 4° C. versus phosphate buffered saline. The liposomes are characterized to assess liposome size and the amount of anti-DNP membrane IgG protein incorporated into the liposomes. Liposome size is determined using dynamic light scattering and flow cytometry (see e.g., U.S. Patent Application No. 2005/0208120 by Albani which is incorporated herein by reference). For example, liposomes containing anti-DNP antibodies may have a mean diameter of approximately 50 nanometers. To measure anti-DNP IgG protein on the liposomes the liposomes are analyzed on a flow cytometer after staining with FITC-labeled anti-IgG antibody. Liposomes are sorted based on FITC fluorescence, forward scatter and side scatter to isolate and count liposomes with IgG. Anti-DNP IgG protein on the liposomes is measured using an enzyme-linked immunosorbent assay (ELISA). Methods to analyze liposomes by flow cytometry and to measure IgG and other proteins by ELISA are known (see e.g., U.S. Patent Application No. 2005/0208120, Ibid).

Liposomes containing anti-DNP membrane IgG are fused with memory B cells specific for influenza virus (see above) to obtain memory B cells with anti-DNP B cell receptor. Purified liposomes with anti-DNP BCR on their surface are electrofused with the memory B cells (see e.g., Zimmermann et al., *IEEE Transactions On Plasma Science* 28: 72-82, 2000 which is incorporated herein by reference). For example a 1:1 ratio of liposomes to memory B cells are suspended in a hypo-osmolar buffer containing 0.1 mM Ca-acetate, 0.5 mM Mg-acetate and 1 mg/ml bovine serum albumin. The osmolarity is adjusted to approximately 75 mOsm and approximately 200 µL of the cell suspension containing approximately $2\times10^4$ to $2\times10^5$ cells is placed in an electrofusion chamber (electrofusion generators and chambers are available from BTX Instrument Division, Harvard Apparatus, Inc. Holliston, Mass.). The cells are aligned by applying an alternating field of 5 V amplitude and 2 MHz frequency for approximately 30 seconds. Then fusion is initiated by applying a rectangular fusion pulse of 20V to 40V amplitude and of 15 µsec duration. The alternating field is applied again for 30 seconds to maintain cells and liposomes in position while fusion occurs. The cells are transferred to culture flasks and grown for 2 to 5 weeks.

The fused memory B cells are characterized to assess their anti-DNP BCRs and their production of anti-influenza antibodies. The fused memory B cells are tested for membrane anti-DNP antibodies using fluorescent DNP-HSA and FACS analysis. Methods to assess membrane anti-DNP IgG antibodies using flow cytometry are described above (see Example 2). The fused memory B cells may be activated in vitro to produce anti-influenza antibodies when stimulated with DNP-HSA, and the production of secreted anti-influenza virus antibodies may be measured using an ELISA based upon influenza viral hemagglutinin protein or influenza virions. Methods to measure anti-influenza antibodies and memory B cell activation are known (see e.g., U.S. Pat. No. 7,378,276 Ibid. and Example 1).

The human patient at risk of influenza viral infection is given recombinant fused memory B cells as a therapeutic and prophylactic cell therapy which can be activated in vivo. The recombinant memory B cells are activated in vivo by administration of DNP-HSA to the patient when an anti-influenza antibody response is needed. For example, approximately $10^8$-$10^9$ fused B cells may be injected as a prophylactic when the patient is healthy prior to "flu season." The fused memory B cells may be activated when needed by intracutaneous injection of 100 µg of DNP-HSA to the patient. For example, the fused memory B cells may be activated after the patient is exposed to influenza virus or at the first signs of infection. The production of anti-influenza antibodies may be monitored by sampling the patient's peripheral blood and performing ELISA with influenza virions as the antigen. Moreover, the presence of broadly neutralizing antibodies for multiple strains of influenza virus can be determined by ELISA based on conserved epitopes from influenza virus (see e.g., Ekiert et al., Ibid.)

Example 5

Construction of Autologous Memory B Lymphocytes Engineered to Produce Two Different Anti-*Staphylococcus aureus* Antibodies.

An isolated recombinant B lymphocyte cell line that produces two different secreted immunoglobulins to methicillin-resistant *Staphylococcus aureus* (MRSA) and produces a membrane immunoglobulin to a third *S. aureus* antigen can be utilized for cell therapy in a mammalian subject. The recombinant B lymphocyte cell line can be injected into the mammalian subject as cell therapy to provide immunological protection from infection by MRSA. The recombinant B lymphocyte cell line can be activated in vivo or ex vivo to produce antibody to MRSA by injecting the mammalian subject (or an in vitro cell culture) with *S. aureus* antigen. The timing to stimulate immunological protection from MRSA infection in the mammalian subject can be chosen based upon the exposure of the subject to MRSA or the appearance of symptoms of MRSA infection.

A patient infected with methicillin-resistant *Staphylococcus aureus* (MRSA) who has suffered recurring episodes of infection is treated with his own long-lived, memory B cells which have been genetically engineered to express two different anti-*S. Aureus* monoclonal antibodies (MAb). Memory B cells expressing membrane IgG (also known as surface IgG or B cell receptor (BCR)) are isolated from the peripheral blood of the patient with a recurrent MRSA infection. Polyclonal memory B cells with unknown antigen specificities are isolated from the patient's peripheral blood: 1) by isolating peripheral blood mononuclear cells using Ficoll Hypaque density gradients (available from Sigma Aldrich, St. Louis, Mo.); 2) by negative selection of total B cells using magnetic beads (available from Stem Cell Technology, Vancouver, BC), and 3) by labeling the cells with fluorescent monoclonal antibodies that recognize IgG and CD27, a memory B cell marker, and performing fluorescence-activated cell sorting. See for example, U.S. Pat. No. 7,378,276 issued to Ettinger et al. on May 27, 2008 and U.S. Pat. No. 7,993,864 issued to Brown et al. on Aug. 9, 2011 which are incorporated herein by reference. The purified memory B cells are modified using genetic engineering methods to introduce immunoglobulin (Ig) genes encoding two different anti-*S. aureus* antibodies.

Ig genes encoding a first anti-*S. aureus* IgG antibody are isolated from a hybridoma cell line which produces the antibody. Methods to construct a hybridoma cell line producing an IgG antibody specific for poly-N-acetylglucosamine (PNAG) which is protective against *S. aureus* are described (see e.g., Kelly-Quintos et al., *Infection and Immunity* 74: 2742-2750, 2006 which is incorporated herein by reference). For example transgenic mice with human Ig genes (e.g., XenoMouse® available from Abgenix Inc., Fremont, Calif.) are immunized with PNAG and their B cells are fused with a myeloma cell fusion partner, e.g. SP2/0 cells (available from American Type Culture Collection, Manassas, Va.) to create hybridoma cell clones expressing human antibodies (see e.g., U.S. Pat. No. 8,013,128 Ibid.) Hybridomas expressing high affinity antibodies for PNAG are selected for cloning of their Ig genes. Methods to clone Ig heavy (H) chain and light (L) chain genes are known (see e.g., U.S. Pat. No. 7,741,077 issued to Grawunder et al. on Jun. 22, 2010 and Early et al., *Proc. Natl. Acad. Sci. USA* 76: 857-861,1979 which are incorporated herein by reference). For example, a hybridoma cell line expressing an anti-PNAG antibody, $IgG_1$(kappa), is grown in culture and used as a source to isolate messenger RNA (mRNA) and genomic DNA using standard methods employing phenol/chloroform (see e.g., Sambrook et al., In: *Molecular Cloning: A Laboratory Manual*, $2^{nd}$ Ed., Cold Spring Harbor Press, Cold Spring Harbor, N.Y., 1989). The mRNA encoding the IgG$_1$H-chain and the kappa L-chain are molecularly cloned following amplification using the polymerase chain reaction (PCR) and reverse transcriptase (RT). Methods and Ig gene primers to amplify the H chain and L chain mRNA are described in U.S. Pat. No. 7,741,077 Ibid. The H and L chain mRNA (amplified as complementary DNA) are cloned in a plasmid vector (e.g., pCR®2.1-TOPO plasmid available from Invitrogen Corp., Carlsbad, Calif.) and the DNA sequence of the Ig H chain variable (V) region (including the Vh, D and J segments) and the kappa L chain V-region (including the Vk and Jk segments) are determined. The V-region DNA sequences may be determined by automated DNA sequencing (DNA sequencing services are available from Charles River Laboratories International, Inc., Wilmington, Mass.).

To isolate the corresponding genomic Ig genes, the genomic DNA isolated from the anti-PNAG hybridoma, as isolated above, is used as a template for PCR amplification of the H chain gene and kappa L chain gene. PCR primers (oligonucleotides) to amplify the V-region genes, (including their respective promoters and flanking regions upstream (i.e., 5' of the V genes) are determined by searching a human genome database with the V-region DNA sequences established from the cloned Ig mRNA. For example a human genome nucleotide database available from the National Center for Biotechnology Information can be searched with a computer program, BLAST, for sequences matching the H- and L-chain V-regions. A Human RefSeq Genome database and BLAST software are available online (see e.g., the world wide web at blast.ncbi.nlm.nih/gov/blast.cgi). Primers to amplify the Ig constant regions, enhancer sequences, the H-chain membrane anchors, poly A addition sites and downstream flanking regions (i.e., 3' of the Ig gene) are described (see e.g., U.S. Pat. No. 7,741,077 Ibid.). The PCR-amplified, genomic fragments can be cloned in a plasmid vector such as pCR®2.1-TOPO available from Invitrogen Corp., Carlsbad, Calif.). The IgG$_1$ H chain gene (i.e., $\gamma_1$-H chain gene) may be engineered to remove the "tail piece" and polyadenylation site encoding the secreted form of the H chain, thus only a membrane $\gamma_1$-H chain is encoded by the engineered gene (see e.g., FIG. 3B, and Abbas et al., *Cellular and Molecular Immunology*, $7^{th}$ Ed., Elsevier Saunders, Philadelphia, Pa., 2011 which is incorporated herein by reference). For example, the cloned $\gamma_1$-H chain gene may be amplified by PCR with primers that amplify the $\gamma_1$-H chain constant region gene but omit the tail piece and polyadenlyation site encoding the secreted form of the $\gamma_1$-H chain. Separate DNA fragments encoding the membrane anchor exons and the remainder of the $\gamma_1$-H chain gene are PCR-amplified using PCR primers containing restriction enzyme sites which allow reassembly of the $\gamma_1$-H gene encoding a membrane form of the $\gamma_1$-H chain. See FIG. 3B. Methods to amplify and assemble Ig H and L chain genes are described (see e.g., U.S. Pat. No. 7,741,077 Ibid.).

The Ig genes encoding the heavy (H) chain and light (L) chain of the anti-PNAG antibody are cloned in targeting plasmid vectors to allow targeted integration at and replacement of the corresponding functionally rearranged Ig H and Ig L chain genes on chromosomes 14 and 2 respectively (e.g., See FIG. 1). Methods to target genes to Ig loci using homologous recombination are known (see e.g., U.S. Pat. No. 5,202,238 issued to Perry et al. on Apr. 13, 1993; U.S. Pat. No. 6,570,061 issued to Rajewsky and Zou on May 27, 2003 and U.S. Pat. No. 6,841,383 issued to Reff et al. on Jan. 11, 2005 which are incorporated herein by reference). To target integration into the functional $\gamma_1$-H chain locus, targeting sequences from the intron between the $J_H$ cluster and the μ constant region gene ($C_H\mu$; see FIG. 2A) are placed 5' of the anti-PNAG γ-H chain gene and sequences downstream from the γ1 membrane anchor exons are placed 3' of the γ-H chain gene (see FIG. 3A). Analogous targeting sequences (i.e., from the $J_K$-$C_K$ intron and 3' of the $C_K$ gene) are used for targeting the anti-PNAG kappa light chain gene into the functional $C_K$ gene. The targeting vectors for anti-PNAG H and L chain include selectable marker genes, e.g., hygromycin resistance and Zeocin™ bleomycin resistance, respectively. Media containing hygromycin B and Zeocin™ bleomycin are used to select for engineered memory B cells expressing membrane IgG anti-PNAG antibody (Protocols, selection agents and selectable markers are available from Invitrogen, Carlsbad, Calif.). Essential transcriptional promoter sequences and enhancer sequences necessary for Ig gene expression are retained in the Ig replacement genes (see Abbas et al., Ibid.). Following transfection, homologous recombination and selection, recombinant memory B cells expressing membrane IgG specific for *S. aureus* PNAG are isolated using magnetic beads with PNAG attached (magnetic beads and protocols are available from Miltenyi Biotech Inc., Auburn, Calif.). Memory B cells expressing the anti-PNAG membrane antibody are cultured in vitro prior to transfection with Ig genes encoding a second antibody specific for a different *S. aureus* antigen.

Memory B cells are produced using recombinant DNA methods to express a membrane antibody specific for PNAG and are further genetically engineered to express a second anti-*S. aureus* MAb. A monoclonal antibody (MAb) specific for the immunodominant staphylococcal antigen A (IsaA) is expressed in the memory B cells. To obtain an anti-IsaA MAb with prophylactic and therapeutic activity for *S. aureus* infections a hybridoma cell line is constructed using purified recombinant IsaA protein to immunize mice and select hybridoma clones (see e.g., Lorenz et al., *Antimicrob. Agents Chemoth.* 55: 165-173, 2011 which is incorporated herein by reference). To clone anti-IsaA antibody variable region genes messenger RNA is extracted from a selected hybridoma cell line and used as a template for complementary DNA synthesis with reverse transcriptase (RT) and amplification using polymerase chain reaction (PCR) (i.e., RT-PCR). Methods to amplify and clone the variable regions for heavy and light chain in an antibody expression vector are described (see e.g., Kelly-Quintos et al., Ibid.) For example, a plasmid expression vector encoding a complete gamma (γ)-1 H chain and a lambda (λ) L chain may be constructed using restriction enzymes and standard molecular biology methods (see e.g., Sambrook et al., Ibid.). To facilitate transfection and expression of the anti-IsaA antibody in memory B cells the γ1-H chain gene and the λ-L chain gene may be transferred to a lentiviral vector (see e.g., U.S. Pat. No. 7,939,059 issued to Yang et al. on May 10, 2011 which is incorporated herein by reference). Infection of memory B cells with the recombinant lentivirus results in integration of the vector sequences at random sites (i.e., not targeted) in the genomic DNA of the memory B cells and production of the secreted IgG1 (λ) anti-IsaA antibody. Protocols and lentiviral expression vectors are available from Invitrogen Corp., Carlsbad, Calif.; see e.g., User Manual: "ViraPower™ HiPerfom™ Lentiviral Expression System" which is incorporated herein by reference. For example a flask of memory B cells is infected with titered recombinant lentivirus stock so as to yield a multiplicity of infection of approximately 1.0 transducing units per cell.

The cells and lentivirus are incubated overnight at 37° C. in 5% $CO_2$; then, the lentivirus containing media is replaced by fresh media and incubated overnight. On the third day the cells are placed in selective media (e.g., media containing blasticidin is available from Invitrogen Corp., Carlsbad, Calif.) to select for stably transduced cells containing the lentiviral vector. Clones of memory B cells resistant to blasticidin are also placed under selection for hygromycin B and Zeocin™ to select clones expressing both anti-MRSA antibodies. To identify and purify memory B cells expressing both anti-*S. aureus* antibodies memory B cells with surface IgG specific for PNAG are purified using magnetic beads (available from Miltenyi Biotec Inc., Auburn, Calif.) and cultured in vitro with PNAG. Methods to obtain PNAG and culture conditions for human memory B cells are described (see e.g., Kelly-Quintos et al., Ibid. and U.S. Pat. No. 7,378,276, Ibid.). Supernatants from the cultures are tested for anti-IsaA IgG antibody with an ELISA (see e.g., Lorenz et al., Ibid.) and memory B cells producing anti-IsaA antibody are selected and expanded for adoptive immunotherapy.

The human patient at risk of MRSA infection is given recombinant memory B cells as a therapeutic and prophylactic cell therapy which can be activated in vivo. The recombinant memory B cells are activated in vivo by administration of *S. aureus* antigen to the patient when an anti-MRSA antibody response is needed. For example, approximately $10^8$-$10^9$ recombinant B cells may be injected as a prophylactic when the patient is healthy or has been recently infected with MRSA. The recombinant memory B cells may be activated when needed by intracutaneous injection of 100 μg of *S. aureus* antigen to the patient. For example, the memory B cells may be activated after the patient is exposed to MRSA or at the first signs of infection. The production of anti-MRSA antibodies may be monitored by sampling the patient's peripheral blood and performing ELISA with MRSA antigens as the target antigens.

Example 6

Adoptive Immunotherapy of a Drug-Resistant Bacterial Infection with Autologous Memory B Lymphocytes Engineered to Produce Two Different Anti-*Staphylococcus aureus* Antibodies.

An isolated recombinant B lymphocyte cell line that produces two different secreted immunoglobulins to methicillin-resistant *Staphylococcus aureus* (MRSA) and produces a membrane immunoglobulin to a *S. aureus* antigen can be utilized for cell therapy in a mammalian subject. The recombinant B lymphocyte cell line can be injected into the mammalian subject as cell therapy to provide immunological protection from infection by MRSA. The recombinant B lymphocyte cell line can be activated in vivo or ex vivo to produce antibody to MRSA by injecting the mammalian subject (or an in vitro cell culture) with *S. aureus* antigen. The timing to stimulate immunological protection from MRSA infection in the mammalian subject can be chosen based upon the timing of an outbreak of MRSA infection in the population at large.

To protect and treat a patient with recurrent MRSA infections the patient is given autologous recombinant B cells. The patient's memory B cells are genetically engineered to express two antibodies recognizing two *S. aureus* antigens: poly-N-acetyl glucosamine (PNAG) and immunodominant *S. aureus* antigen (IsaA). The recombinant memory B cells are activated and expanded in vitro in culture media (e.g., RPMI 1640, Sigma-Aldrich, St. Louis, Mo.) containing: cognate antigen, PNAG, at approximately 100 ng/mL and activating cytokines, e.g., interleukin-2 (Roche, Indianapolis, Ind.), interleukin-4, interleukin-21 and an anti-CD40 antibody (R&D Systems, Minneapolis, Minn.). After approximately 5 days of culture the memory B cells are harvested, washed and concentrated prior to infusion in the patient. Approximately $5 \times 10^8$ recombinant B cells are infused in the patient and the expansion and persistence of the recombinant B cells are followed by sampling the patient's peripheral blood. Methods to infuse and track genetically engineered lymphocytes are described (see e.g., Kalos et al., *Sci. Transl. Med.* 3, 95ra73, 2011; DOI: 10.1126/scitranslmed.3002842 which is incorporated herein by reference). For example, quantitative PCR analysis on genomic DNA obtained from the patient's whole blood may be used to determine the copy number of the anti-PNAG Ig genes and the anti-IsaA Ig genes per microgram of genomic DNA. Approximately 100-200 ng of genomic DNA is analyzed with ABI Taqman technology (available from Life Technologies Corp., Carlsbad, Calif.). PCR primers specific for the transfected Ig genes are validated by analysis of control genomic DNA spiked with known copy numbers of the anti-*S. aureus* Ig genes. The number of genetically engineered B cells persisting in the peripheral blood may also be assessed using flow cytometry and fluorescently labeled PNAG in combination with an anti-IgG antibody. For example, phycoerythrin (PE)-conjugated PNAG and fluorescein isothiocyanate (FITC)-conjugated anti IgG are used to stain the recombinant B cells and count them. Protocols, reagents and instrumentation for flow cytometry are available from Becton Dickinson, Franklin Lakes, N.J. In addition, the level of anti-IsaA IgG ($\lambda$) antibody in the patient's peripheral blood may be analyzed using an ELISA. The ELISA may be constructed with recombinant purified IsaA protein and anti-IgG or anti-$\lambda$ L-chain antibodies. Methods to construct and perform an ELISA are known (see e.g., Kelly-Quintos et al., Ibid.).

The recombinant memory B cells may be activated in vivo as well as in vitro to produce anti-*S. aureus* antibodies. The memory B cells may be activated in vivo by PNAG released from *S. aureus* infecting the patient or by injection of purified PNAG. Methods to purify PNAG from *S. aureus* are known (see e.g., Lorenz et al., Ibid.). The memory B cells are activated in vivo by binding of PNAG to their B cell receptors (BCR) and by interaction with T cells and cytokines (see e.g., Abbas et al., Ibid.). To enhance the activation of the recombinant memory B cells the PNAG may be administered with an immunologic adjuvant (e.g., aluminum hydroxide). Repeated activations of the memory B cells may be performed in response to recurrent MRSA infections.

The human patient at risk of MRSA infection is administered recombinant memory B cells as a therapeutic and prophylactic cell therapy which can be activated in vivo. The recombinant memory B cells are activated in vivo by administration of PNAG antigen to the patient when an anti-MRSA antibody response is needed. For example, approximately $10^8$-$10^9$ recombinant B cells may be injected as a prophylactic when the patient is healthy or has been recently infected with MRSA. The recombinant memory B cells may be activated when needed by intracutaneous injection of 100 μg of PNAG to the patient. For example, the memory B cells may be activated after the patient is exposed to MRSA or at the first signs of infection. The production of anti-MRSA antibodies may be monitored by sampling the patient's peripheral blood and performing ELISA with MRSA antigens as the target antigens. Moreover, the presence of antibodies for MRSA can be determined by ELISA based on conserved epitopes from MRSA (see e.g., Ekiert et al., Ibid.).

Example 7

Construction of Cytotoxic B Cells with a Recombinant B Cell Receptor.

B lymphocytes produce antibodies in response to binding antigens from infectious disease microorganisms, or cancer cells, but when co-stimulated with antigens and selected cytokines they may also produce cytotoxic molecules. For example, stimulation of B cells with the cytokine, interleukin-21 (IL-21) and antigen can result in the production of cytotoxic molecules (e.g., granzyme B) which may cause cell death. Cytotoxic B cells that are useful for adoptive cell therapy are constructed by engineering a recombinant B cell receptor (BCR) which recognizes a disease associated antigen and signals to elicit expression of cytotoxic effector functions.

A recombinant B cell receptor is constructed with a single chain antibody, membrane immunoglobulin (Ig) domains, and the cytoplasmic domain of the IL-21 receptor. In this case, the single chain antibody, a single chain variable fragment (SCFv), is specific for a tumor associated antigen, prostate cancer lipid antigen (PCLA). The SCFv is linked to membrane Ig heavy chain domains including: Hinge (H), constant region 3 ($C_H3$), transmembrane (TM) and cytoplasmic (Cyto) domains which participate in signaling for B cell activation, and lastly, to the IL-21 receptor cytoplasmic domain which signals to elicit cytotoxicity functions from the B cell. See FIG. 8A. Thus, the gene transfer and expression of the recombinant B cell receptor in these engineered B cells produces modified B cells that are responsive to the antigen PCLA. Upon exposure to PCLA on cancer cells, the modified B cells produce cytotoxic effector molecules, such as granzyme B, and kill prostate cancer cells expressing PCLA.

The immunoglobulin (Ig) genes encoding an antibody that binds PCLA are isolated and engineered to construct a recombinant BCR gene for transfer and expression in a diseased subject's own B cells. PCLA, a glycolipid antigen associated with prostate cancer is obtained from prostate cancer cell lines and used as an antigen. The glycolipid antigen is used to select a single chain antibody variable fragment (SCFv) which binds PCLA. SCFv containing Ig variable region genes connected by a linker peptide have been described and can be adapted to this embodiment and methods to select antibodies from phage display single chain variable fragment (SCFv) libraries can be utilized. A SCFv protein (and the corresponding SCFv gene) which avidly binds PCLA on prostate cancer cells is selected for construction of a recombinant BCR.

The anti-PCLA SCFv gene is attached to segments encoding domains of membrane IgG1 heavy (H)-chain to create a recombinant B cell receptor. The hinge segment 1008, the carboxy-terminal heavy chain constant region domain ($C_H3$) 1010, the transmembrane domain (TM) 1015, and the cytoplasmic domain 1020 of membrane IgG1 heavy chain are encoded at the 3' end of the SCFv 1005 gene. See FIG. 8A. Detailed methods to construct membrane IgG H-chains can be adapted to this embodiment. The IgG1 transmembrane and cytoplasmic domains are a 52 amino acid segment that interacts with the associated transmembrane B cell signaling proteins, Igα and Igβ, that comprise the B cell receptor [(see e.g., Abbas et al., *Cellular and Molecular Immunology*, 7th Edition, pp. 159-161, 2012, Elsevier, Philadelphia, Pa.)].

The last segment of the recombinant B cell receptor contains the cytoplasmic domain of the interleukin-21 (IL-21) receptor 1025. The IL-21 receptor can signal to elicit cytotoxic effector functions in B cells. For example, co-stimulation of human B cells with an anti-Ig antibody (i.e., stimulation of membrane IgG) and IL-21 elicits expression of cytotoxic effectors such as granzyme B and perforin. The cytoplasmic domain of the IL-21 receptor protein has been identified, and the structure and signaling of the IL-21 receptor have been described. See FIG. 8A for a model of the recombinant B cell receptor protein.

DNA segments encoding the SCFv, IgG constant domains and the IL-21 receptor cytoplasmic domain are amplified from DNA clones using the polymerase chain reaction or synthesized (e.g., Custom DNA synthesis is available from Life Technologies Corp., Grand Island, N.Y. 14072). The segment encoding the anti-PCLA SCFv may be amplified from the phage clone selected above. Immunoglobulin constant region, transmembrane domain and cytoplasmic domain sequences can be synthesized by automated DNA synthesis based on publicly available sequences, and the IL-21 receptor sequence and subdomains are available. The gene encoding the recombinant B cell receptor may be assembled from the DNA segments using the splice overlap extension method.

The recombinant B cell receptor gene is inserted in a mammalian cell expression vector for transfer into human B cells. An expression vector with cytomegalovirus (CMV) promoter elements, a selectable marker gene and poly A addition signals is described. See FIG. 8B. The plasmid vector directs expression of the recombinant B cell receptor under the control of the CMV promoter and carries a selectable marker gene to allow selection of B cells expressing the vector with a drug (e.g., Neo expression confers resistance to G418; both resistance gene, Neo, and drug, G418, are available from InVivoGen, San Diego, Calif.). The plasmid vector encoding the recombinant B cell receptor is transfected into primary human B cells (isolated from peripheral blood) using a device, kit and protocol available from Lonza Inc., Allendale, N.J. 07401 (see e.g., Human B Cell Protocol Nucleofector® Kit, which is incorporated herein by reference). Transfected, G418-resistant B cells expressing the recombinant B cell receptor are identified by flow cytometry using antibodies specific for the SCFv present in the recombinant B cell receptor. Alternatively PCLA antigen may be used to identify B cells expressing the recombinant B cell receptor, for example, by identifying and sorting cells by flow cytometry.

B cells expressing the recombinant B cell receptor are tested in vitro for cytotoxic effector function following stimulation. Cytotoxic B cells expressing the anti-PCLA recombinant BCR are stimulated with antibodies specific for the SCFv or Ig H-chain constant region components (e.g., anti-human IgG) of the recombinant BCR, and cell culture supernatants are analyzed for the presence of Granzyme B by using an immunoassay. A Granzyme B ELIspot assay kit (available from Cell Sciences, Canton, Mass.) may be used to determine the number of Granzyme B producing cells in a culture. An Immunospot Analyzer and Immunospot 3 software (CTL Cellular Technology Ltd., Cleveland, Ohio) can be used to detect and count the Granzyme B producing modified B cells.

To determine target cell killing by the recombinant cytotoxic B cells, a flow cytometry-based assay is used to determine the percentage of target cells which are apoptotic after exposure to recombinant cytotoxic B cells. For example, approximately 250,000 recombinant cytotoxic B cells are added to 10,000 prostate cancer cells (e.g., PC3 cell line which expresses PCLA). After co-culture for approximately 3 days, target cell (i.e., PC3) apoptosis is determined by staining with annexin V and propidium iodide; the percentage of apoptotic cells is determined by flow cytometry. A matched negative control culture with a target cell line not expressing PCLA (e.g., HeLa) is compared to the PC3 culture. Also, cultures with different ratios of effector cells (recombinant cytotoxic B cells) to target cells (PC3 cells) are analyzed. For example, cultures with Effector: Target ratios of 5:1, 10:1, 25:1 and 50:1 are analyzed for target cell apoptosis and viability. A plot of target cell viability versus Effector:Target cell ratio can indicate cytotoxic effector function by the recombinant cytotoxic B cells.

Example 8

Construction of Cytotoxic B Cells with a Recombinant B Cell Receptor and Coordinate Perforin Expression.

Modified B cells that exhibit cytotoxicity responsive to a prostate cancer tumor antigen are engineered with a recombinant B cell receptor and an inducible gene for perforin which promote cytotoxicity for the target cells. Stimulation of B cells with the cytokine, interleukin-21 (IL-21) and antigen can result in the production of cytotoxic molecules (e.g., granzyme B) which may cause cell death. However, expression of perforin, an important cytotoxic effector molecule may be lacking in B cells. Therefore, in order to provide coordinated production of perforin, an expression cassette for perforin is placed under the control of Ig heavy chain variable region ($V_H$) promoter/enhancer sequences. Engineered cytotoxic B cells with coordinate expression of granzyme B and perforin are cytotoxic for target cells, i.e., prostate cancer cells.

A recombinant B cell receptor is constructed with a single chain antibody, membrane immunoglobulin (Ig) domains, and the cytoplasmic domain of the IL-21 receptor. The single chain antibody, a single chain variable fragment (SCFv), is specific for a tumor associated antigen, prostate cancer lipid antigen (PCLA). The SCFv is linked to membrane Ig heavy chain domains including: Hinge (H), constant region 3 ($C_H3$), transmembrane (TM) and cytoplasmic domains, which participate in signaling B cell activation, and lastly, to the IL-21 receptor cytoplasmic domain which signals to elicit cytotoxicity functions from the B cell. See FIG. 8A. Gene transfer and expression of the recombinant B cell receptor expression vector (see FIG. 8B) generates B cells that express the recombinant receptor, respond to PCLA, and produce cytotoxic effector molecules such as granzyme B. A detailed description of the recombinant B cell receptor is given in Prophetic Example 1 above.

Moreover the expression vector and transfection methods to obtain B cells expressing the recombinant B cell receptor are given (see Prophetic Example 1). Recombinant B cells respond to antigen (i.e., PCLA or tumor cells bearing PCLA on their surface) by signaling via the recombinant BCR to activate transcription at the active Ig H and L loci. For example, signaling by the recombinant BCR via interaction with Igα and Igβ may result in B cell activation and differentiation, and signaling via the IL-21 cytoplasmic domain may lead to granzyme B production. In addition, to further promote the cytotoxicity of the recombinant B cell, the human perforin gene is introduced at the active functional Ig H chain locus under the control of the Ig $V_H$ promoter and Ig enhancer elements.

Cytotoxic B cells are engineered to express the human perforin gene from the active functional Ig heavy chain locus and under the control of Ig $V_H$ promoter sequences and an Ig enhancer element. The gene encoding human perforin is publicly available. The approximately 1668 nucleotide complementary DNA (cDNA) encoding human perforin is amplified using the polymerase chain reaction (PCR) and oligonucleotide primers to add terminal sequences homologous to 5' and 3' flanking sequences of the active, rearranged Ig gamma H-chain gene in the recombinant B cell line. See FIG. 3A. For example, the perforin cDNA is amplified with a 5' primer containing approximately 30 nucleotides homologous to upstream sequence flanking the active $V_H$ gene (see e.g., $V_H1D_1J_2$ in FIG. 3A), and a 3' primer containing approximately 30 nucleotides homologous to sequence downstream from the active constant region gene (see e.g., $C_H\gamma$ in FIG. 3A). The amplified perforin gene with ends homologous to the active Ig H-chain gene on chromosome 14 is integrated by homologous recombination to replace the γH chain gene (see FIG. 8C). Engineering and site-specific integration of genes at the active Ig heavy chain locus in an isolated recombinant cell line are described [(see e.g., U.S. Pat. No. 9,175,072, Ibid.)]. Perforin expression by transfected B cells may be determined using an Elispot assay which enumerates perforin producing cells in vitro following stimulation of the cells. Materials and protocols for a human perforin Elispot assay are available from Cell Sciences, Inc., Canton, Mass. (see Data sheet: Human Perforin Elispot Kit, available online at www.cellsciences.com which is incorporated herein by reference).

To determine target cell killing by recombinant cytotoxic B cells expressing perforin, a flow cytometry-based assay is used to determine the percentage of target cells which are apoptotic after exposure to recombinant cytotoxic B cells. For example, approximately 250,000 recombinant cytotoxic B cells are added to 10,000 prostate cancer cells (e.g., PC3 cell line which expresses PCLA). After co-culture for approximately 3 days, target cell (i.e., PC3) apoptosis is determined by staining with annexin V and propidium iodide; the percentage of apoptotic cells is determined by flow cytometry. A matched negative control culture with a target cell line not expressing PCLA (e.g., HeLa) is compared to the PC3 culture. Also, cytotoxic B cells not transfected with the perforin gene are compared in the cytotoxicity assay. Cultures with different ratios of effector cells (recombinant cytotoxic B cells) to target cells (PC3 cells) are analyzed. For example, cultures with Effector:Target ratios of 5:1, 10:1, 25:1 and 50:1 are analyzed for target cell apoptosis and viability. A plot of target cell viability versus Effector:Target cell ratio can indicate cytotoxic effector function by the recombinant cytotoxic B cells.

Example 9

Engineered B Lymphocytes Express a Recombinant B-Cell Receptor Specific for Prostate Cancer Lipid Antigen and a Secreted Antibody Specific for Prostate Specific Stem Cell Antigen.

An isolated recombinant B lymphocyte cell line that expresses a recombinant B cell receptor (BCR) specific for prostate cancer lipid antigen (PCLA) and secretes an antibody recognizing prostate stem cell antigen (PSCA) is constructed for therapy of prostate cancer. The recombinant B lymphocyte cell line is infused in a subject to provide B cells that are not only cytotoxic for tumor cells but also produce a therapeutic antibody that recognizes prostate cancer cells. Recombinant B lymphocyte cells bind PCLA on prostate cancer cells via an engineered recombinant BCR and are activated to produce cytotoxic effectors (e.g., Granzyme B) and to secrete anti-PSCA antibody.

The recombinant B cells provide cellular and humoral immunity targeted to prostate cancer cells. The recombinant B lymphocyte cell line can also be stimulated in vivo or ex vivo by injecting the mammalian subject (or an in vitro cell culture) with exogenous PCLA to elicit cytotoxic effectors and to produce secreted anti-PSCA antibody. Determination of timing to stimulate immunological reactivity to prostate cancer cells in the mammalian subject can be chosen based upon the detection of prostate cancer cells in the mammalian subject.

Polyclonal memory B cells expressing B cell receptors (BCR) of membrane IgG are isolated from a prostate cancer patient. Polyclonal memory B cells are isolated from the patient's peripheral blood: 1) by isolating peripheral blood mononuclear cells using Ficoll Hypaque density gradients (available from Sigma Aldrich. St. Louis. Mo.); 2) by negative selection of total B cells using magnetic beads (available from Stem Cell Technology Vancouver, BC), and 3) by labeling the cells with fluorescent monoclonal antibodies that recognize membrane IgG and CD27, a memory B cell marker, and performing fluorescence-activated cell sorting. Memory B cells expressing membrane IgG are cultured in vitro and genetically engineered to express a recombinant B cell receptor and a secreted anti-PCSA antibody.

Memory B cells are genetically engineered to express a recombinant BCR specific for PCLA and a secreted IgG antibody specific for prostate stem cell antigen (PSCA). An isolated recombinant cell line is constructed that includes a recombinant BCR. The recombinant BCR binds PCLA on prostate cancer cells and signals intracellularly to the B cell to elicit expression and release of cytotoxic effector molecules such as Granzyme B as described above in Prophetic Example 6. The recombinant cell line may be selected using drug selection, e.g., G418, and flow cytometry to identify clones expressing the recombinant BCR (see e.g., Prophetic Example 6 above).

Immunoglobulin genes encoding an anti-PSCA antibody (i.e., Ig heavy chain and light chain genes) are integrated at the active, rearranged Ig heavy chain locus on chromosome 14 (see FIG. 3A), and the active, rearranged kappa light chain locus on chromosome 2, respectively. Methods and materials to obtain anti-PSCA antibodies are available. For example, to target integration of anti-PSCA antibody genes into the functional γ1-H chain locus, targeting sequences from the intron between the $J_H$ exons and the γ constant region gene ($C_H\gamma$; see FIG. 3A) are placed 5' of the anti-PSCA γ1-H chain gene and targeting sequences selected downstream (3') from the γ1-H chain cytoplasmic exon are placed 3' of the γ1-H chain gene (see FIG. 3A). Analogous targeting sequences (i.e., from the Jk-Ck intron and 3' of the Ck gene) are used for targeting the anti-PSCA kappa L chain gene into the functional Ck gene. The targeting vectors for anti-PSCA H and L chain include selectable marker genes, e.g., hygromycin resistance and histidinol dehydrogenase, respectively. Media containing hygromycin and histidinol are used to select for engineered memory B cells expressing the targeting vectors encoding a secreted IgG anti-PSCA antibody.

Following transfection and selection of the recombinant memory B cells, those cells producing secreted IgG antibodies specific for PSCA are identified using standard immunoassays to assess B cell supernatants. The engineered memory B cells are cultured in vitro and stimulated with PCLA to activate the cell cytotoxicity and to stimulate secretion of anti-PSCA IgG antibodies. Laboratory methods to purify PCLA, the lipid antigen, can be adapted for this embodiment. Also, isolated recombinant cell lines expressing the recombinant B cell receptor and anti-PSCA antibodies are tested in a cytotoxicity assay with target cells expressing PCLA and PSCA. For example, PC3, a prostate tumor cell line bearing PCLA can be transduced with a vector encoding PSCA and tested in vitro in cytotoxicity assays with engineered cytotoxic B cell lines. Methods and materials for transducing PC3 cells are described, and details of the cytotoxicity assay are described above. See Prophetic Example 6.

Example 10

Construction of Cytotoxic B Cells for Prostate Cancer by Transfection of B Cells with Transcription Factors.

Cytotoxic B cells are produced by engineering memory B cells expressing B cell receptors (BCR) specific for prostate cancer lipid antigen (PCLA). The B cells are transfected with a viral vector encoding transcription factors which control the expression of cytotoxic effector molecules including granzyme B and perforin. Engineered cytotoxic B cells that recognize and kill prostate cancer cells can be used for adoptive cell therapy in prostate cancer patients.

Memory B cells expressing B cell receptors recognizing PCLA are constructed with immunoglobulin (Ig) genes encoding an anti-PCLA antibody. The engineered Ig genes are inserted at the actively transcribed heavy (H) and light (L) chain loci on human chromosomes 14 and 2. Polyclonal memory B cells expressing B cell receptors (BCR) of membrane IgG are isolated from a prostate cancer patient. Polyclonal memory B cells are isolated from the patient's peripheral blood: 1) by isolating peripheral blood mononuclear cells using Ficoll Hypaque density gradients (available from Sigma Aldrich. St. Louis. Mo.); 2) by negative selection of total B cells using magnetic beads (available from Stem Cell Technology Vancouver, BC), and 3) by labeling the cells with fluorescent monoclonal antibodies that recognize membrane IgG and CD27, a memory B cell marker, and performing fluorescence-activated cell sorting. Memory B cells expressing membrane IgG are cultured in vitro and genetically engineered to express a B cell receptor specific for PCLA.

Immunoglobulin genes encoding an anti-PCLA antibody (i.e., Ig heavy chain and light chain genes) are integrated at the active, rearranged Ig heavy chain locus on chromosome 14 (see FIG. 3A), and the active, rearranged kappa light chain locus on chromosome 2, respectively. Anti-PCLA antibodies are obtained, and the corresponding Ig genes are isolated, engineered and site-specifically integrated at the active Ig heavy chain and light chain loci in an isolated recombinant cell line. For example, to target integration of anti-PCLA membrane Ig H-chain gene into the functional, rearranged γ-H chain locus: Targeting sequences upstream (5') from the variable region exon (VH1D1J2; see FIG. 3A) and downstream (3') from the gamma-H chain constant region exon (CHγ; see FIG. 3A) are placed 5' and 3' respectively, of the engineered, membrane γ-H chain gene (see FIG. 3B). Analogous targeting sequences (i.e., from 5' of VkJk exon and 3' of the Ck gene) are used for targeting the anti-PCLA kappa L chain gene into the functional Ck gene on Chromosome 2.

Engineered B cells expressing membrane IgG specific for PCLA are transduced with a viral vector encoding three transcription factors essential for cytotoxic B cell function. Three transcription factors regulate the expression of cytotoxic effector molecules such as granzyme B. Transcription factors: T-bet, Runx3 and Eomes are essential for the expression of granzyme B and perforin in the context of cytotoxic T cell differentiation. A tricistronic vector encoding T-bet, Runx3 and Eomes is constructed using a Sendai virus vector which transduces human B cells. See FIG. 8D. Transfection and expression of the vector in the engineered B cells can be monitored by immunostaining with antibody-enzyme conjugates specific for T-bet, Runx3 and Eomes (e.g., anti-Eomes, anti-T-bet and anti-Runx3 antibodies are available from Abcam, Cambridge, Mass.), and expression of Granzyme B and perforin can be detected by reverse transcriptase-polymerase chain reaction (RT-PCR) of RNA from the transfected cells.

Engineered cytotoxic B cells expressing membrane IgG specific for PCLA are tested for cytotoxic effector function versus prostate cancer cell lines. For example, PC3, a prostate tumor cell line bearing PCLA can be used as a target cell in a flow cytometric assay that detects apoptotic cells following exposure to the engineered cytotoxic B cells (see Prophetic Example 2 above).

Engineered cytotoxic B cells expressing membrane IgG recognizing PCLA can also be tested in vivo in a xenogeneic mouse model of human prostate cancer. For example, PC3, human prostate tumor cells are implanted subcutaneously in immunodeficient mice (e.g., NSG mice available from Jackson Labs, Bar Harbor, Me.) and the mice are treated with the engineered cytotoxic B cells. The mice are evaluated with respect to tumor size, body weight and survival. Control tumor cell lines can include tumors not expressing PCLA. Moreover, the survival or expansion of cytotoxic B cells in the mice following infusion or injection in control mice or PC3 tumor-bearing mice is evaluated and recorded.

Each recited range includes all combinations and subcombinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will recognize that there are various vehicles by which processes and/or systems and/or other technologies disclosed herein can be effected (e.g., hardware, software, and/or firmware), and that the preferred vehicle will vary with the context in which the processes and/or systems and/or other technologies are deployed. For example, if a surgeon determines that speed and accuracy are paramount, the surgeon may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies disclosed herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those having ordinary skill in the art will recognize that optical aspects of implementations will typically employ optically-oriented hardware, software, and or firmware.

In a general sense the various aspects disclosed herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices disclosed herein, or a microdigital processing unit configured by a computer program which at least partially carries out processes and/or devices disclosed herein), electrical circuitry forming a memory device (e.g., forms of random access memory), and/or electrical circuitry forming a communications device (e.g., a modem, communications switch, or optical-electrical equipment). The subject matter disclosed herein may be implemented in an analog or digital fashion or some combination thereof.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for treating a disease in a vertebrate subject with an immunotherapeutic product comprising:
  isolating from a vertebrate subject exposed to at least one second antigen, a B lymphocyte cell line expressing at least one endogenous secreted immunoglobulin reactive to the at least one second antigen;
  introducing into the isolated B lymphocyte cell line at least one exogenous membrane immunoglobulin or recombinant B cell receptor that is reactive to at least one first antigen to produce a recombinant B lymphocyte cell line;

introducing into the isolated B lymphocyte cell line at least one exogenous membrane receptor eliciting at least one effector molecule to produce a recombinant B lymphocyte cell line; and selecting the recombinant B lymphocyte cell line expressing the membrane immunoglobulin reactive to the at least one first antigen, expressing the at least one endogenous secreted immunoglobulin reactive to the at least one second antigen for administration to one or more vertebrate subjects, and expressing the at least one exogenous recombinant B cell receptor eliciting at least one effector molecule.

2. The method of claim 1 further comprising:
administering the at least one first antigen to stimulate the recombinant B lymphocyte cell line; and
testing for the presence of the at least one endogenous secreted immunoglobulin reactive to the at least one second antigen in the recombinant B lymphocyte cell line.

3. The method of claim 1 further comprising:
administering to the vertebrate subject a pharmaceutical composition including the isolated B lymphocyte cell line; and
administering to the vertebrate subject the at least one first antigen to stimulate the isolated B lymphocyte cell line to produce the at least one endogenous secreted immunoglobulin reactive to the at least one second antigen.

4. The method of claim 3 further comprising:
confirming the presence of the at least one endogenous secreted immunoglobulin reactive to the at least one second antigen in a bloodstream of the vertebrate subject.

5. The method of claim 1 further comprising:
administering the at least one first antigen to stimulate the recombinant B lymphocyte cell line;
testing for the presence of the at least one endogenous secreted immunoglobulin reactive to the at least one second antigen; and
administering to the vertebrate subject a pharmaceutical composition including the stimulated recombinant B lymphocyte cell line.

6. The method of claim 1, wherein the recombinant B lymphocyte cell line is autologous to one of the one or more vertebrate subjects.

7. The method of claim 1, wherein the recombinant B lymphocyte cell line is allogeneic to the one or more vertebrate subjects.

8. The method of claim 7, wherein assessing cytotoxicity effects includes assessing effector molecule expression.

9. The method of claim 7, wherein assessing cytotoxicity effects includes assessing effector molecule function.

10. The method of claim 7, wherein assessing cytotoxicity effects includes assessing at least one of perforin, granzyme B, Fas Ligand, or TRAIL.

11. The method of claim 7, comprising:
exposing the at least one isolated recombinant B lymphocyte cell line to the at least one first antigen, and
testing for the activation of the at least one isolated recombinant B lymphocyte cell line to express the exogenous secreted immunoglobulin reactive to the at least one second antigen.

12. The method of claim 11, comprising:
isolating the exogenous secreted immunoglobulin reactive to the at least one second antigen from the at least one isolated recombinant B lymphocyte cell line or from a culture of the at least one isolated recombinant B lymphocyte cell line.

13. The method of claim 12, wherein activating the at least one exogenously incorporated membrane immunoglobulin with the first antigen is capable of controlling expression of the at least one exogenously incorporated nucleic acid encoding at least one secreted immunoglobulin reactive to the second antigen.

14. The method of claim 12, wherein the at least one isolated B lymphocyte cell line includes at least one of naive B lymphocytes, immature B lymphocytes, transitional B lymphocytes, mature B lymphocytes, follicular B lymphocytes, memory B lymphocytes, plasmablasts, or plasma cells.

15. The method of claim 12, wherein the at least one isolated B lymphocyte cell line includes at least one memory B lymphocyte.

16. A method for treating a disease in a vertebrate subject with an immunotherapeutic product comprising:
introducing into at least one B lymphocyte cell line at least one exogenous membrane immunoglobulin reactive to at least one first antigen to produce at least one first B lymphocyte cell line;
selecting the at least one first B lymphocyte cell line expressing the membrane immunoglobulin reactive to the at least one first antigen;
introducing into the at least one first B lymphocyte cell line at least one exogenous nucleic acid encoding one or more secreted immunoglobulins reactive to at least one second antigen to produce at least one recombinant B lymphocyte cell line;
selecting the at least one recombinant B lymphocyte cell line expressing the secreted one or more immunoglobulin reactive to the at least one second antigens for administration to one or more vertebrate subjects;
introducing into the B lymphocyte cell line at least one exogenous recombinant B cell receptor eliciting at least one effector molecule; and
selecting the at least one recombinant B lymphocyte cell line expressing the one or more recombinant B cell receptors eliciting at least one cytotoxic effector molecule.

17. The method of claim 16, further comprising:
selecting the at least one recombinant B lymphocyte cell line expressing the at least one exogenous membrane immunoglobulin reactive to the at least one first antigen.

18. The method of claim 16, further comprising:
administering the at least one first antigen to stimulate the at least one recombinant B lymphocyte cell line; and
testing for the presence of the one or more secreted immunoglobulin reactive to the at least one second antigen in the at least one recombinant B lymphocyte cell line.

19. The method of claim 16, further comprising:
administering to the vertebrate subject a pharmaceutical composition including the at least one recombinant B lymphocyte cell line; and
administering to the vertebrate subject the at least one first antigen to stimulate the at least one recombinant B lymphocyte cell line to produce the one or more exogenous secreted immunoglobulin reactive to the at least one second antigen.

20. The method of claim 19, further comprising:
confirming the presence of the at least one exogenous secreted immunoglobulin reactive to the at least one second antigen in a bloodstream of the vertebrate subject.

21. The method of claim 16, further comprising:
administering the at least one first antigen to stimulate the at least one recombinant B lymphocyte cell line to produce the one or more exogenous secreted immunoglobulin reactive to the at least one second antigen; and
administering to the vertebrate subject a pharmaceutical composition including the stimulated at least one recombinant B lymphocyte cell line.

22. The method of claim 16, further comprising:
introducing into the at least one first B lymphocyte cell line at least one exogenous membrane immunoglobulin reactive to the at least one second antigen.

23. The method of claim 16, further comprising:
introducing into the at least one recombinant B lymphocyte cell line at least one exogenous nucleic acid encoding one or more secreted immunoglobulins reactive to at least one third antigen to produce at least one second recombinant B lymphocyte cell line; and
selecting the at least one second recombinant B lymphocyte cell line expressing at least one of the secreted immunoglobulin reactive to the at least one second antigen and the secreted immunoglobulin reactive to the at least one third antigen.

24. The method of claim 23, further comprising:
administering to the vertebrate subject a pharmaceutical composition including the at least one second recombinant B lymphocyte cell line; and
administering to the vertebrate subject the at least one first antigen to stimulate the at least one second recombinant B lymphocyte cell line to produce the one or more exogenous secreted immunoglobulin reactive to the at least one second antigen and the one or more exogenous secreted immunoglobulin reactive to the at least one third antigen.

25. The method of claim 24, further comprising:
confirming the presence of the at least one exogenous secreted immunoglobulin reactive to the at least one second antigen and the one or more exogenous secreted immunoglobulin reactive to the at least one third antigen in a bloodstream of the vertebrate subject.

26. The method of claim 24, further comprising:
administering to the vertebrate subject the at least one first antigen to stimulate the at least one isolated second recombinant B lymphocyte cell line to produce the one or more exogenous secreted immunoglobulin reactive to the at least one second antigen and the one or more exogenous secreted immunoglobulin reactive to the at least one third antigen; and
administering to the vertebrate subject a pharmaceutical composition including the stimulated at least one second recombinant B lymphocyte cell line.

27. The method of claim 19, wherein the recombinant B lymphocyte cell line is autologous to one of the one or more vertebrate subjects.

28. The method of claim 19, wherein the recombinant B lymphocyte cell line is allogeneic to the one or more vertebrate subjects.

29. The method of claim 19, wherein introducing into the B lymphocyte cell line at least one exogenous recombinant B cell receptor to eliciting at least one cytotoxic effector includes introducing at least one exogenous nucleic acid encoding at least one recombinant B cell receptor eliciting at least one cytotoxic effector.

30. The method of claim 29, wherein the at least one exogenous nucleic acid encoding at least one recombinant B cell receptor includes at least one exogenous nucleic acid encoding at least one receptor cytoplasmic domain.

31. The method of claim 29, wherein the at least one exogenous nucleic acid encoding at least one recombinant B cell receptor eliciting at least one effector molecule includes at least one exogenous nucleic acid encoding at least one recombinant B cell receptor eliciting at least one nucleic acid encoding one or more of perforin, granzyme B, Fas ligand or TRAIL.

32. A method comprising:
administering to a subject afflicted with a disease or disorder, a therapeutically effective amount of a cell line including an B lymphocyte cell line capable of expressing at least one exogenously incorporated membrane immunoglobulin or a recombinant B cell receptor that is reactive to a first antigen and at least one endogenous secreted immunoglobulin reactive to a second antigen;
wherein the B lymphocyte cell line is capable of expressing cytotoxicity for at least one target cell.

\* \* \* \* \*